(12) United States Patent
Ozawa

(10) Patent No.: US 12,163,074 B2
(45) Date of Patent: Dec. 10, 2024

(54) HOST MATERIAL, COMPOSITION, AND ORGANIC ELECTROLUMINESCENT ELEMENT

(71) Applicant: KYULUX, INC., Fukuoka (JP)

(72) Inventor: Hiroaki Ozawa, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 139 days.

(21) Appl. No.: 17/760,128

(22) PCT Filed: Feb. 4, 2021

(86) PCT No.: PCT/JP2021/004053
§ 371 (c)(1),
(2) Date: Aug. 4, 2022

(87) PCT Pub. No.: WO2021/157642
PCT Pub. Date: Aug. 12, 2021

(65) Prior Publication Data
US 2023/0113918 A1 Apr. 13, 2023

(30) Foreign Application Priority Data

Feb. 4, 2020 (JP) ................ 2020-017201
May 22, 2020 (JP) ................ 2020-090095
Sep. 1, 2020 (JP) ................ 2020-147167

(51) Int. Cl.
*C09K 11/02* (2006.01)
*C07D 405/10* (2006.01)
(Continued)

(52) U.S. Cl.
CPC ............ *C09K 11/02* (2013.01); *C07D 405/10* (2013.01); *C07D 409/14* (2013.01);
(Continued)

(58) Field of Classification Search
CPC . C09K 11/02; C09K 11/06; C09K 2211/1007; C09K 2211/1018;
(Continued)

(56) References Cited

U.S. PATENT DOCUMENTS

2015/0115205 A1  4/2015  Kang

FOREIGN PATENT DOCUMENTS

CN  110272427 A  9/2019
CN  110498790 A  11/2019
(Continued)

OTHER PUBLICATIONS https://www.wiredchemist.com/data/hammett-sigma-constants (Year: 2017).*

(Continued)

*Primary Examiner* — Mark Kopec
*Assistant Examiner* — Jaison P Thomas
(74) *Attorney, Agent, or Firm* — FISHERBROYLES, LLP; Roger L. Browdy

(57) ABSTRACT

To improve the emission efficiency, the driving voltage and the lifetime of an organic light-emitting device using a delayed fluorescent material. A host material for a delayed fluorescent material, containing a compound represented by the following general formula: $R^1$ to $R^5$ each are a substitu- (Continued)

ent not containing a cyano group, n1 to n5 each are 0 to 4, Ar is a monocyclic arylene group or a monocyclic heteroarylene group.

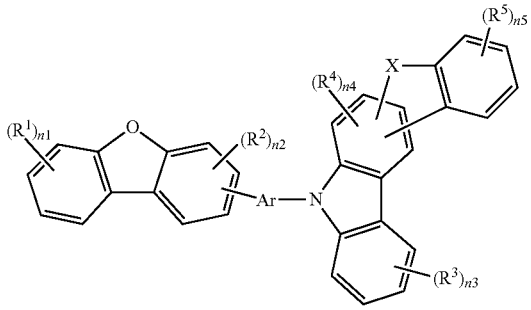

18 Claims, 1 Drawing Sheet

(51) Int. Cl.
*C07D 409/14* (2006.01)
*C07D 491/048* (2006.01)
*C07D 491/153* (2006.01)
*C09K 11/06* (2006.01)
*H10K 85/60* (2023.01)
*H10K 50/11* (2023.01)

(52) U.S. Cl.
CPC ..... *C07D 491/048* (2013.01); *C07D 491/153* (2013.01); *C09K 11/06* (2013.01); *H10K 85/654* (2023.02); *H10K 85/657* (2023.02); *H10K 85/6574* (2023.02); *H10K 85/6576* (2023.02); *C09K 2211/1007* (2013.01); *C09K 2211/1018* (2013.01); *H10K 50/11* (2023.02)

(58) Field of Classification Search
CPC ............... C07D 405/10; C07D 409/14; C07D 491/048; C07D 491/153; C07D 207/448; C07D 209/12; C07D 209/86; C07D 213/74; C07D 215/26; C07D 219/14; C07D 221/20; C07D 223/26; C07D 223/28; C07D 231/06; C07D 233/96; C07D 239/26; C07D 241/38; C07D 251/24; C07D 263/42; C07D 271/107; C07D 277/66; C07D 307/91; C07D 309/34; C07D 311/04; C07D 311/74; C07D 333/16; C07D 333/76; C07D 401/10; C07D 401/14; C07D 403/10; C07D 403/14; C07D 405/04; C07D 405/14; C07D 413/04; C07D 413/10; C07D 413/14; C07D 455/04; C07D 417/04; C07D 417/10; C07D 417/14; C07D 471/04; C07D 471/06; C07D 471/14; C07D 471/16; C07D 487/04; C07D 487/16; C07D 487/22; C07D 491/16; C07D 495/04; C07D 498/04; C07D 519/00; H10K 85/654; H10K 85/657; H10K 85/6574; H10K 85/6576; H10K 50/11; H10K 2101/20; H10K 85/6572; H10K 85/658
See application file for complete search history.

(56) References Cited

FOREIGN PATENT DOCUMENTS

| CN | 110872316 | A | | 3/2020 |
|---|---|---|---|---|
| CN | 112940023 | A | | 6/2021 |
| JP | 2017530945 | A | | 10/2017 |
| JP | 2020-132636 | A | | 8/2020 |
| KR | 1020180138422 | A | | 12/2018 |
| WO | 2013/109045 | A1 | | 7/2013 |
| WO | 2013179645 | A1 | | 12/2013 |
| WO | 2016010136 | A1 | | 1/2016 |
| WO | WO-2018113538 | A1 | * | 6/2018 |
| WO | 2018155642 | A1 | | 8/2018 |
| WO | WO-2020122118 | A1 | * | 6/2020 ........... C07D 405/10 |
| WO | 2021/157642 | A1 | | 8/2021 |
| WO | 2022/270592 | A1 | | 12/2022 |

OTHER PUBLICATIONS

International Preliminary Report on Patentability dated Jan. 4, 2024, from International Application No. PCT/JP2022/025151.
International Search Report and Written Opinion dated Apr. 6, 2021, from International Application No. PCT/JP2022/025151.
Extended European Search Report dated Jun. 26, 2023, from corresponding European patent application No. 21750815.9.
International Preliminary Report on Patentability of Chapter I for PCT/JP2021/004053, dated Jul. 28, 2022, and English translation thereof.
International Search Report and Search Opinion for PCT/JP2021/004053, dated Apr. 6, 2021, and English translation thereof.
Hansch et al., "A Survey of Hammett Substituent Constants and Resonance and Field Parameters", American Chemical Society, vol. 91, No. 2 pp. 165-195 (1991).
Joyama et al., "Highly efficient organic light-emitting diodes from delayed fluorescence" Nature I vol. 492, pp. 234-238 (Dec. 2012).

* cited by examiner

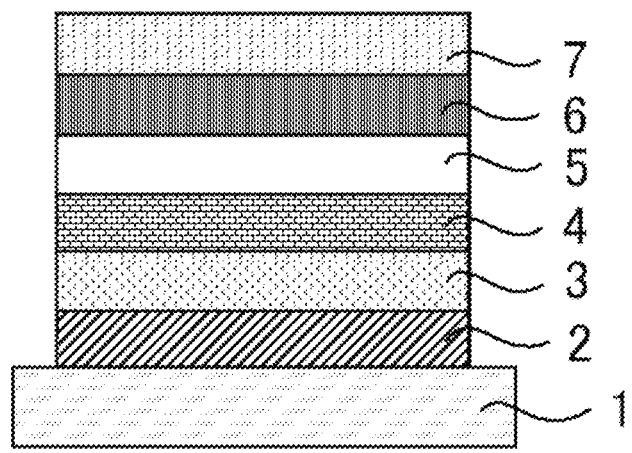

HOST MATERIAL, COMPOSITION, AND ORGANIC ELECTROLUMINESCENT ELEMENT

TECHNICAL FIELD

The present invention relates to a compound useful as a host material, and a composition and an organic light-emitting device using the compound.

BACKGROUND ART

Studies for enhancing the light emission efficiency of light-emitting devices such as organic electroluminescent devices (organic EL devices) are being made actively. In particular, various kinds of efforts have been made for increasing light emission efficiency by newly developing and combining an electron transporting material, a hole transporting material, a light emitting material, and a host material to constitute an organic electroluminescent device. Among them, an organic electroluminescent device that utilizes a delayed fluorescent material has been developed and has attracted attention (see NPL 1).

A delayed fluorescent material is a material which, in an excited state, after having undergone reverse intersystem crossing from an excited triplet state to an excited singlet state, emits fluorescence when returning back from the excited singlet state to a ground state thereof. Fluorescence through the route is observed later than fluorescence from the excited singlet state directly occurring from the ground state (ordinary fluorescence), and is therefore referred to as delayed fluorescence. Here, for example, in the case where a light-emitting compound is excited through carrier injection thereinto, the occurring probability of the excited singlet state to the excited triplet state is statistically 25%/75%, and therefore improvement of light emission efficiency by the fluorescence alone from the directly occurring excited singlet state is limited. On the other hand, in a delayed fluorescent material, not only the excited singlet state thereof but also the excited triplet state can be utilized for fluorescent emission through the route via the above-mentioned reverse intersystem crossing, and therefore as compared with an ordinary fluorescent material, a delayed fluorescent material can realize a higher emission efficiency. The delayed fluorescent material having such characteristics is generally used in a light-emitting layer of an organic electroluminescent device along with a host material therein, and actually contributes toward improvement of emission efficiency.

CITATION LIST

Non-Patent Literature

NPL 1: Uoyama, et al., Nature 492, 234-238 (2012)

SUMMARY OF INVENTION

Technical Problem

As a host material to be combined with a delayed fluorescent material, a compound having a larger lowest excited singlet energy than a delayed fluorescent material is selected. However, even when a host material used as combined with a conventional fluorescent material that does not emit delayed fluorescence is combined with a delayed fluorescent material directly as it is, a sufficient emission performance could not be realized. In particular, in an organic electroluminescent device using a delayed fluorescent material, there is room for improvement in point of driving voltage and emission lifetime. Consequently, the present inventors have made studies for the purpose of suppressing a driving voltage and prolonging an emission lifetime while attaining a high emission efficiency in an organic light-emitting device using a delayed fluorescent material.

Solution to Problem

As a result of having advanced assiduous studies, the present inventors have found that, when a host material having a specific structure is used as combined with a delayed fluorescent material, a prolonged lifetime can be attained while suppressing a driving voltage and a high emission efficiency can be thereby realized. The invention has been proposed on the basis of these findings, and specifically has the following constitution.

[1] A host material for use along with a delayed fluorescent material, containing a compound having a structure represented by the following formula (1):

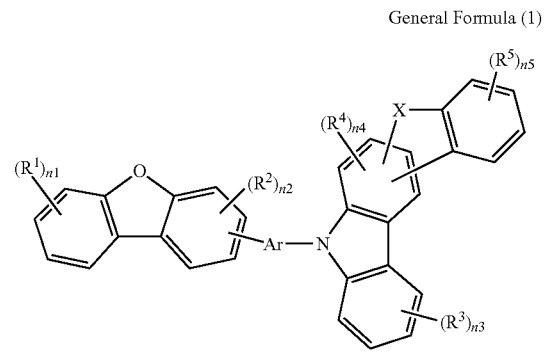

General Formula (1)

wherein $R^1$ to $R^4$ each independently represent a substituent not containing a cyano group, $R^1$ to $R^5$ do not bond to the other $R^1$ to $R^5$ or Ar to form a cyclic structure, but neighboring $R^3$'s can bond to each other to form a benzofuro structure or a benzothieno structure; n1, n3 and n5 each independently represent an integer of any of 0 to 4, n2 represents an integer of any of 0 to 3, n4 represents an integer of any of 0 to 2; X represents an oxygen atom or a sulfur atom; Ar represents a monocyclic arylene group or a monocyclic heteroarylene group, and the monocyclic arylene group and the monocyclic heteroarylene group can be substituted with a substituent not containing a cyano group.

[2] The host material according to [1], wherein the compound has a structure represented by the following general formula (2):

General Formula (2)

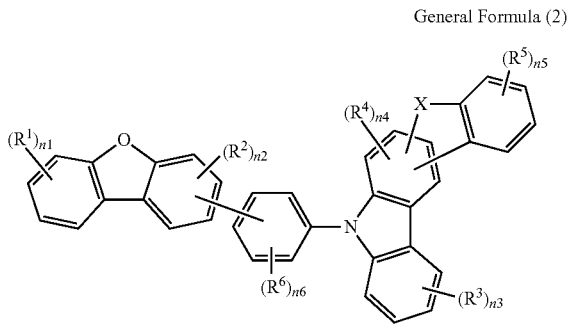

wherein $R^1$ to $R^6$ each independently represent a substituent not containing a cyano group, $R^1$ to $R^5$ do not bond to the other $R^1$ to $R^6$ to form a cyclic structure, but neighboring $R^3$'s can bond to each other to form a benzofuro structure or a benzothieno structure; n1, n3 and n5 each independently represent an integer of any of 0 to 4, n2 and n6 each independently represent an integer of any of 0 to 3, n4 represents an integer of any of 0 to 2; X represents an oxygen atom or a sulfur atom.

[3] The host material according to [1], wherein the compound has a structure represented by the following general formula (3)

General Formula (3)

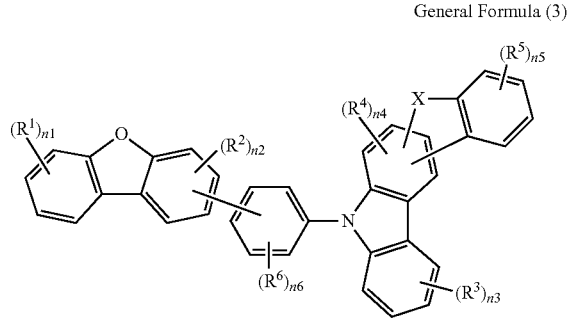

wherein $R^1$ to $R^6$ each independently represent a substituent not containing a cyano group, $R^1$ to $R^5$ do not bond to the other $R^1$ to $R^6$ to form a cyclic structure, but neighboring $R^3$'s can bond to each other to form a benzofuro structure or a benzothieno structure; n1, n3 and n5 each independently represent an integer of any of 0 to 4, n2 and n6 each independently represent an integer of any of 0 to 3, n4 represents an integer of any of 0 to 2; X represents an oxygen atom or a sulfur atom.

[4] The host material according to any one of [1] to [3], wherein $R^1$ to $R^5$ each independently represent a substituent having a Hammett's σp value that falls within a range of −0.3 to 0.3, Ar represents a monocyclic arylene group optionally substituted with a substituent having a Hammett's σp value that falls within a range of −0.3 to 0.3, or a monocyclic heteroarylene group optionally substituted with a substituent having a Hammett's σp value that falls within a range of −0.3 to 0.3.

[5] The host material according to any one of [1] to [4], wherein $R^1$ to $R^5$ each independently represent one group or a combination of two or more groups selected from the group consisting of an alkyl group (for example, having 1 to 40 carbon atoms) and an aryl group (for example, having 6 to 30 carbon atoms), Ar represents a monocyclic arylene group optionally substituted with one group or a combination of two or more groups selected from the group consisting of an alkyl group (for example, having 1 to 40 carbon atoms) and an aryl group (for example, having 6 to 30 carbon atoms), or a monocyclic heteroarylene group optionally substituted with one group or a combination of two or more groups selected from the group consisting of an alkyl group (for example, having 1 to 40 carbon atoms) and an aryl group (for example, having 6 to 30 carbon atoms).

[6] The host material according to any one of [1] to [5], wherein Ar is a substituted or unsubstituted 1,3-phenylene group.

[7] The host material according to any one of [1] to [6], wherein X is an oxygen atom.

[8] A composition containing the host material of any one of [1] to [7] doped with a delayed fluorescent material.

[9] The composition according to [8], which is a film.

[10] The composition according to [8] or [9], wherein the delayed fluorescent material is a compound having a cyanobenzene structure in which the number of the cyano group substituting on the benzene ring is one.

[11] The composition according to [8] or [9], wherein the delayed fluorescent material is a compound having a dicyanobenzene structure in which the number of the cyano groups substituting on the benzene ring is two.

[12] The composition according to any one of [8] to [11], wherein the delayed fluorescent material is a compound having an azabenzene structure in which at least one ring skeleton-constituting carbon atom of the benzene ring is replaced with a nitrogen atom.

[13] The composition according to any one of [8] to [12], further containing a fluorescent compound whose lowest excited singlet energy is lower than that of the host material and the delayed fluorescent material.

[14] An organic light-emitting device having a layer of the composition of any one of [8] to [13].

[15] The organic light-emitting device according to [14], wherein the layer is formed of atoms alone selected from the group consisting of a carbon atom, a hydrogen atom, a nitrogen atom, an oxygen atom, a sulfur atom, a boron atom, and a halogen atom.

[16] The organic light-emitting device according to [14], wherein the layer is formed of atoms alone selected from the group consisting of a carbon atom, a hydrogen atom, a nitrogen atom, an oxygen atom, and a sulfur atom.

[17] The organic light-emitting device according to any one of [14] to [16], which is an organic electroluminescent device.

[18] The organic light-emitting device according to any one of [14] to [17], wherein the composition does not contain the fluorescent compound, and the maximum component for light emission from the device is light emission from the delayed fluorescent material.

[19] The organic light-emitting device according to any one of [14] to [17], wherein the composition contains the fluorescent compound, and the maximum component for light emission from the device is light emission from the fluorescent compound.

Advantageous Effects of Invention

Using the host material doped with a delayed fluorescent material as an organic light-emitting device, there can be provided an organic light-emitting device that can be driven at a low voltage and can have a long lifetime and a high emission efficiency.

BRIEF DESCRIPTION OF DRAWING

[FIGURE] This is a schematic cross-sectional view showing an example of a layer configuration of an organic electroluminescent device.

DESCRIPTION OF EMBODIMENTS

The contents of the invention will be described in detail below. The constitutional elements may be described below with reference to representative embodiments and specific examples of the invention, but the invention is not limited to the embodiments and the examples. In the description herein, a numerical range expressed as "to" means a range that includes the numerical values described before and after "to" as the upper limit and the lower limit. The hydrogen atom that is present in the molecule of the compound used in the invention is not particularly limited in isotope species, and for example, all the hydrogen atoms in the molecule may be $^1$H, and all or a part of them may be $^2$H (deuterium D). In a preferred embodiment of the invention, all the hydrogen atoms in the molecule are $^1$H. In one embodiment of the invention, all the hydrogen atoms in the molecule are $^2$H (deuterium D). In one embodiment of the invention, a part of the hydrogen atoms in the molecule are $^1$H, and the remainder are $^2$H (deuterium D). In the description of the invention, the term "substituted" or "substituent" does not include a hydrogen isotope except $^1$H such as $^2$H (deuterium D).

(Compound Represented by General Formula (1))

In the invention, a compound represented by the following general formula (1) is used.

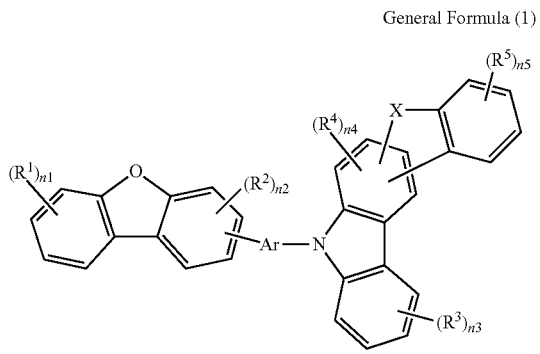

General Formula (1)

In the general formula (1), $R^1$ to $R^5$ each independently represent a substituent not containing a cyano group.

In one embodiment of the invention, $R^1$ to $R^5$ each independently represent a substituent having a Hammett's σp value that falls within a range of −0.3 to 0.3. In one embodiment of the invention, $R^1$ to $R^5$ each independently represent a substituent having a Hammett's σp value that falls within a range of −0.2 to 0.2. In one embodiment of the invention. $R^1$ to $R^5$ each independently represent a substituent having a Hammett's σp value that falls within a range of −0.1 to 0.1. In one embodiment of the invention, $R^1$ to $R^5$ each independently represent a substituent having a Hammett's σp value that falls within a range of more than 0 and 0.3 or less. In one embodiment of the invention, $R^1$ to $R^5$ each independently represent a substituent having a Hammett's σp value that falls within a range of −0.3 or more and less than 0.

Here. "Hammett's $\sigma_p$ value" is one propounded by L. P. Hammett. and is one to quantify the influence of a substituent on the reaction rate or the equilibrium of a para-substituted benzene derivative. Specifically, the value is a constant ($\sigma_p$) peculiar to the substituent in the following equation that is established between a substituent and a reaction rate constant or an equilibrium constant in a para-substituted benzene derivative:

$$\log(k/k_0)=\rho\sigma_p$$

or $$\log(K/K_0)=\rho\sigma_p$$

In the above equations, k represents a rate constant of a benzene derivative not having a substituent; $k_0$ represents a rate constant of a benzene derivative substituted with a substituent; K represents an equilibrium constant of a benzene derivative not having a substituent; $K_0$ represents an equilibrium constant of a benzene derivative substituted with a substituent; ρ represents a reaction constant to be determined by the kind and the condition of reaction. Regarding the description relating to the "Hammett's $\sigma_p$ value" and the numerical value of each substituent, reference may be made to the description relating to $\sigma_p$ value in Hansch, C. et. al., Chem. Rev., 91, 165-195 (1991). A group having a negative Hammett's $\sigma_p$ value tends to exhibit an electron donor property, and a group having a positive Hammett's $\alpha_p$ value tends to exhibit an electron acceptor property.

In one embodiment of the invention, $R^1$ to $R^5$ each are independently a substituent not having an unshared electron pair. In one embodiment of the invention, $R^1$ to $R^5$ each are independently a substituent not having a n-electron.

In one embodiment of the invention, $R^1$ to $R^5$ each independently represent one group or a combination of two or more groups selected from the group consisting of an alkyl group (for example, having 1 to 40 carbon atoms) and an aryl group (for example, having 6 to 30 carbon atoms).

In one embodiment of the invention, $R^1$ to $R^5$ each are independently an alkyl group having 1 to 30 carbon atoms and optionally substituted with an aryl group having 6 to 20 carbon atoms. In one embodiment of the invention, $R^1$ to $R^5$ each are independently an aryl group having 6 to 20 carbon atoms and optionally substituted with an alkyl group having 1 to 30 carbon atoms. In one embodiment of the invention, $R^1$ to $R^5$ each are independently an unsubstituted alkyl group having 1 to 30 carbon atoms. In one embodiment of the invention, $R^1$ to $R^5$ each are independently an unsubstituted aryl group having 6 to 20 carbon atoms.

$R^1$ to $R^5$ do not bond to the other $R^1$ to $R^5$ or Ar to form a cyclic structure, but neighboring $R^3$'s can bond to each other to form a benzofuro structure or a benzothieno structure. Consequently, the dibenzofuran (tricyclic structure) on the left side in the general formula (1) is not further condensed with any other ring to form a tetracyclic or more polycyclic structure. Also, the benzofurocarbazole (pentacyclic structure), the benzothienocarbazole (pentacyclic structure), a bisbenzofurocarbazole (heptacyclic structure) and the bisbenzothienocarbazole (heptacyclic structure) on the right side in the general formula (1) are not further condensed with any other ring. Preferably, the structure on the right side of the general formula (1) is a pentacyclic structure. Namely, in one preferred embodiment of the invention, R³'s do not bond to each other to form a cyclic structure.

In the general formula (1), n1, n3 and n5 each independently represent an integer of any of 0 to 4, n2 represents an integer of any of 0 to 3, n4 represents an integer of any of 0 to 2. In one embodiment of the invention, n1 to n5 each are independently an integer of any of 0 to 2. In one embodiment of the invention, n1 is 0. In one embodiment of the invention, n2 is 0. In one embodiment of the invention, n3 is 0. In one embodiment of the invention, n4 is 0. In one embodiment of the invention, n5 is 0. In one preferred embodiment of the invention, n1 to n5 are all 0.

In the general formula (1), X represents an oxygen atom or a sulfur atom. In one embodiment of the invention, X is a sulfur atom. In one preferred embodiment of the invention, X is an oxygen atom.

In the general formula (1), a single bond extends in the lower left direction from the ortho-position of the benzene ring bonding to the right side of X. The single bond may bond to any of the 1- to 4-positions of the carbazole structure positioned on the right side of Ar in the general formula (1). Also, X may bond to any of the 1- to 4-positions of the carbazole structure positioned on the right side of Ar in the general formula (1). However, the single bond and X bond to the neighboring carbon atoms that constitute the skeleton of the carbazole structure. Consequently, when the single bond bonds to the 2-position, X bonds to the 1-position or the 3-position. When the single bond bonds to the 3-position, X bonds to the 2-position or the 4-position. When the single bond bonds to the 1-position, X bonds to the 2-position. When the single bond bonds to the 4-position, X bonds to the 3-position. In the general formula (1), the single bond is positioned upper than X, but the general formula (1) shall include a structure of the following general formula (1') where the single bond is positioned lower than X.

General Formula (1')

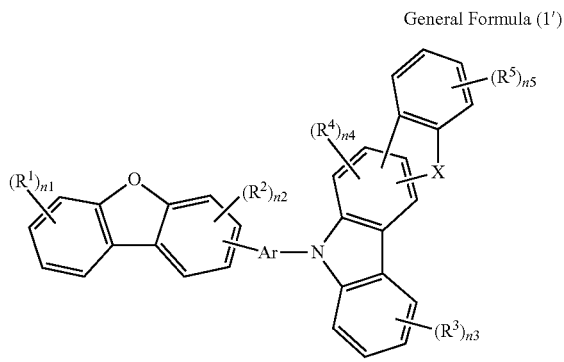

As the benzofurocarbazol-9-yl group bonding to Ar in the general formula (1), a substituted or unsubstituted benzofuro[2,3-a]carbazol-9-yl group can be employed. Also, a substituted or unsubstituted benzofuro[3,2-a]carbazol-9-yl group can be employed. Also, a substituted or unsubstituted benzofuro[2,3-b]carbazol-9-yl group can be employed. Also, a substituted or unsubstituted benzofuro[3,2-b]carbazol-9-yl group can be employed. Also, a substituted or unsubstituted benzofuro[2,3-c]carbazol-9-yl group can be employed. Also, a substituted or unsubstituted benzofuro[3,2-c]carbazol-9-yl group can be employed.

As the benzothienocarbazol-9-yl group bonding to Ar in the general formula (1), a substituted or unsubstituted benzothieno[2,3-a]carbazol-9-yl group can be employed. Also, a substituted or unsubstituted benzothieno[3,2-a]carbazol-9-yl group can be employed. Also, a substituted or unsubstituted benzothieno[2,3-b]carbazol-9-yl group can be employed. Also, a substituted or unsubstituted benzothieno[3,2-b]carbazol-9-yl group can be employed. Also, a substituted or unsubstituted benzothieno[2,3-c]carbazol-9-yl group can be employed. Also, a substituted or unsubstituted benzothieno[3,2-c]carbazol-9-yl group can be employed.

As the bisbenzofurocarbazol-9-yl group bonding to Ar in the general formula (1), a substituted or unsubstituted bisbenzofuro[2,3-a:2',3'-f]carbazol-9-yl group can be employed. Also a substituted or unsubstituted bisbenzofuro[3,2-a:3',2'-f]carbazol-9-yl group can be employed. Also a substituted or unsubstituted bisbenzofuro[2,3-b:2',3'-e]carbazol-9-yl group can be employed. Also a substituted or unsubstituted bisbenzofuro[3,2-b:3',2'-e]carbazol-9-yl group can be employed. Also a substituted or unsubstituted bisbenzofuro[2,3-c:2',3'-d]carbazol-9-yl group can be employed. Also a substituted or unsubstituted bisbenzofuro[3,2-c:3',2'-d]carbazol-9-yl group can be employed.

As the bisbenzothienocarbazol-9-yl group bonding to Ar in the general formula (1), a substituted or unsubstituted bisbenzothieno[2,3-a:2',3'-f]carbazol-9-yl group can be employed. Also a substituted or unsubstituted bisbenzothieno[3,2-a:3',2'-f]carbazol-9-yl group can be employed. Also a substituted or unsubstituted bisbenzothieno[2,3-b:2',3'-e]carbazol-9-yl group can be employed. Also a substituted or unsubstituted bisbenzothieno[3,2-b:3',2'-e]carbazol-9-yl group can be employed. Also a substituted or unsubstituted bisbenzothieno [2,3-c:2',3'-d]carbazol-9-yl group can be employed. Also a substituted or unsubstituted bisbenzothieno [3,2-c:3',2'-d]carbazol-9-yl group can be employed.

Specific examples of the substituted or unsubstituted benzofurocarbazol-9-yl group or the substituted or unsubstituted benzothienocarbazol-9-yl group bonding to Ar in general formula (1) are shown below. However, the structure employable in the invention should not be limitatively interpreted by these specific examples. In this description, * shows a bonding position. Ph represents an unsubstituted phenyl group. Also in this description, a methyl group is not expressed as CH₃, and the expression of CH₃ is omitted as on the left lower side of D7.

D1

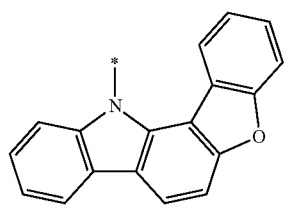

D2

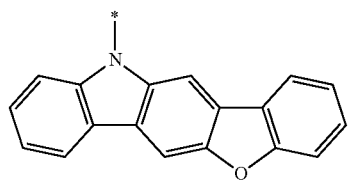

-continued
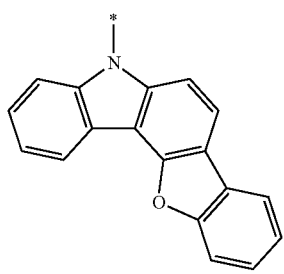
D3
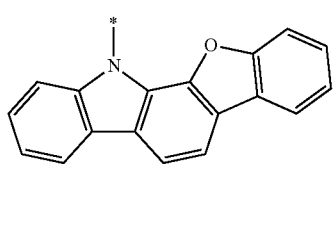
D4
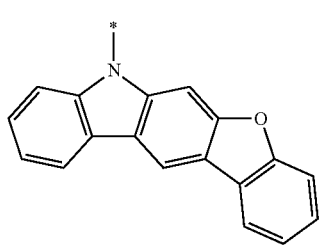
D5
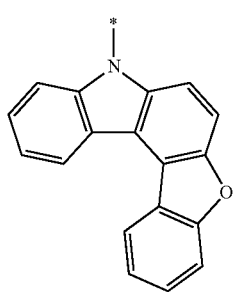
D6
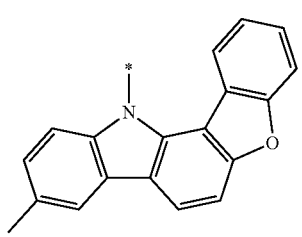
D7
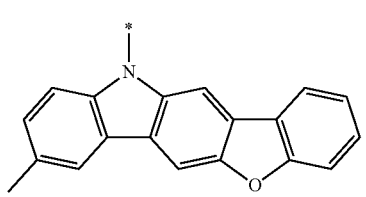
D8
-continued
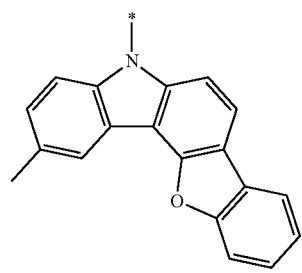
D9
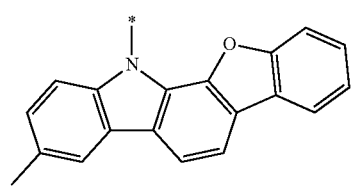
D10
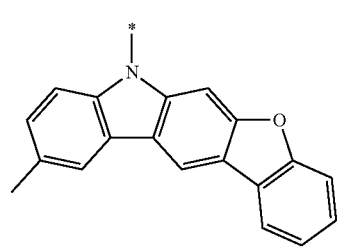
D11
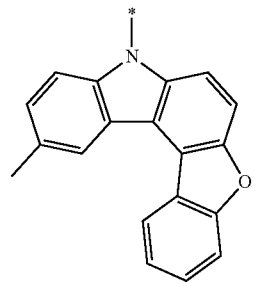
D12
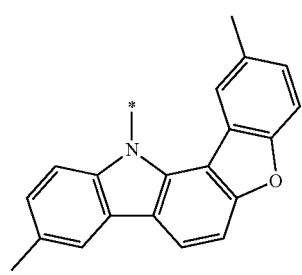
D13
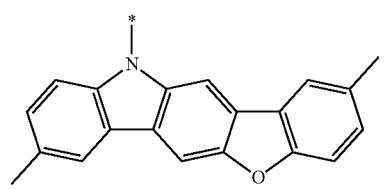
D14

D15 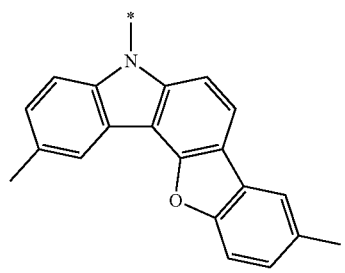
D16 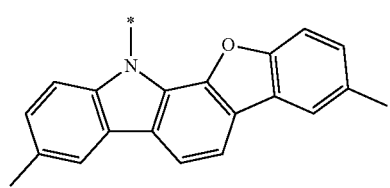
D17 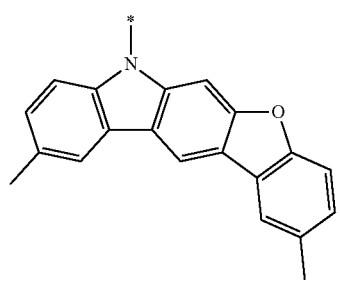
D18 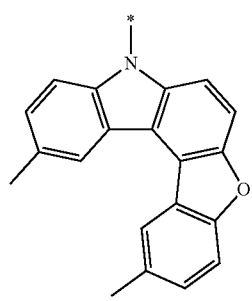
D19 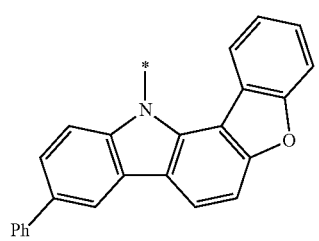
D20 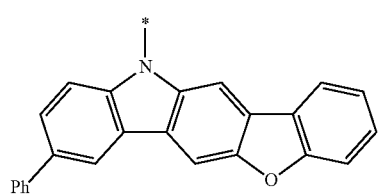
D21 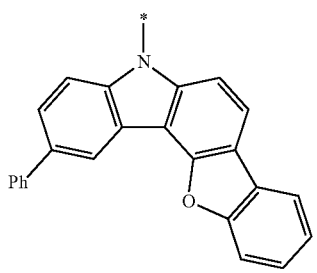
D22 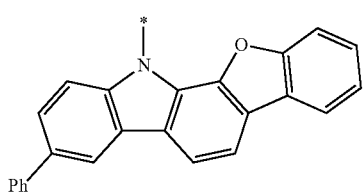
D23 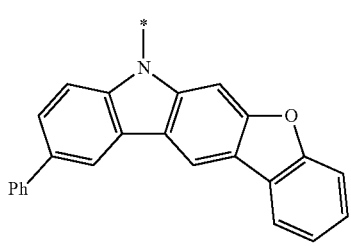
D24 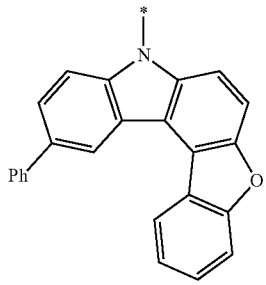
D25 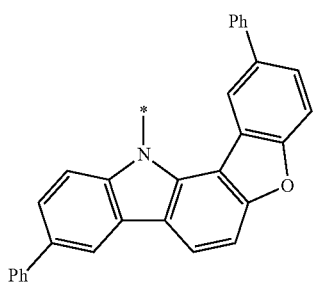
D26 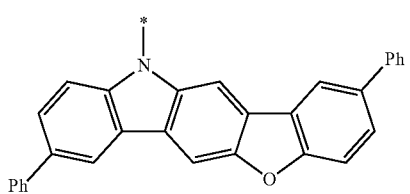

D27 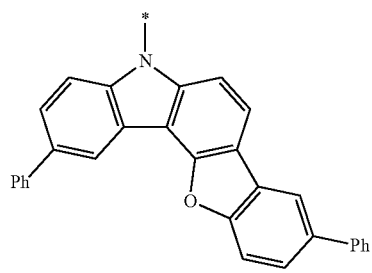
D28 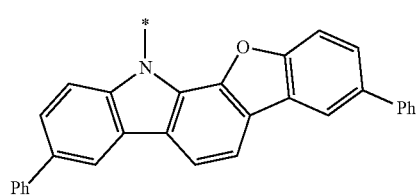
D29 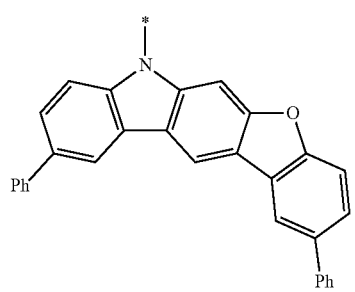
D30 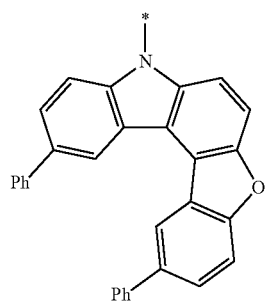
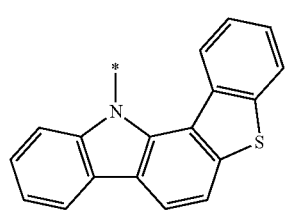 D31
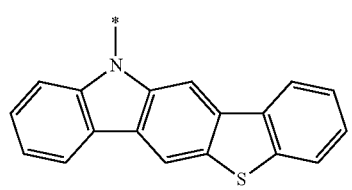 D32
D33 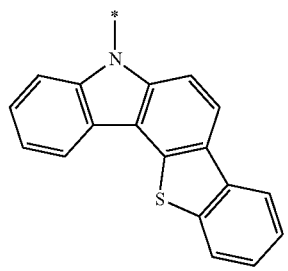
D34 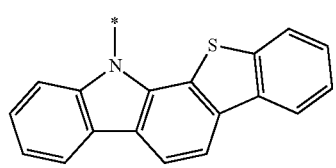
D35 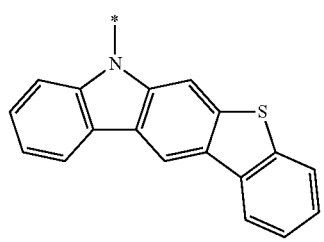
D36 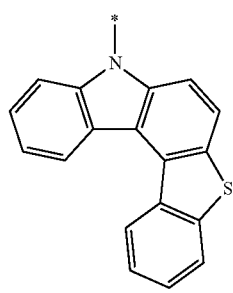
D37 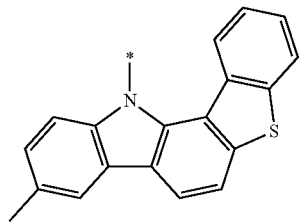
D38 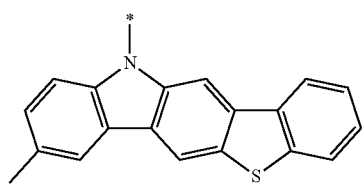

-continued
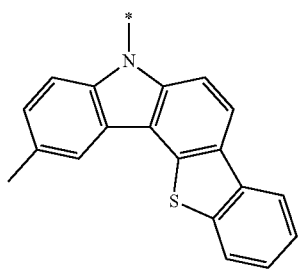
D39
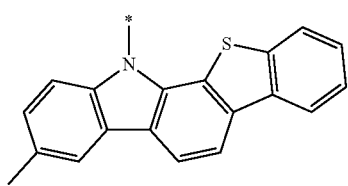
D40
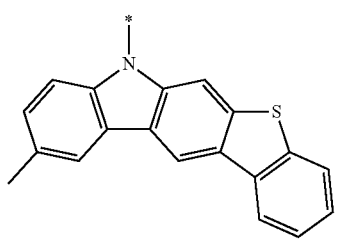
D41
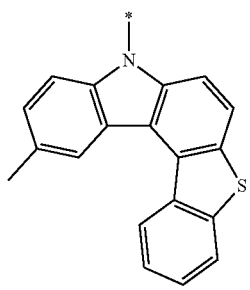
D42
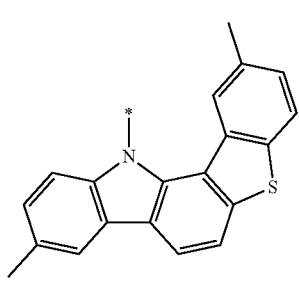
D43
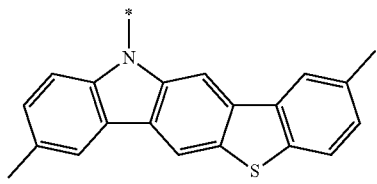
D44
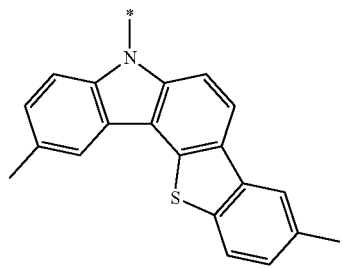
D45
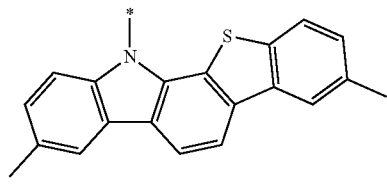
D46
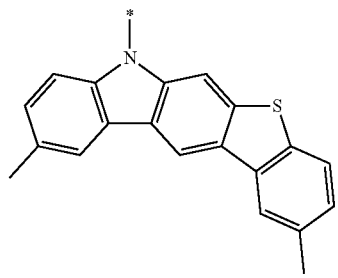
D47
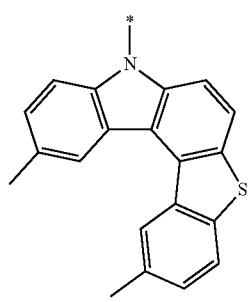
D48
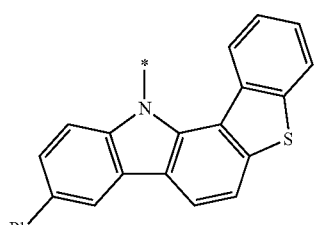
D49
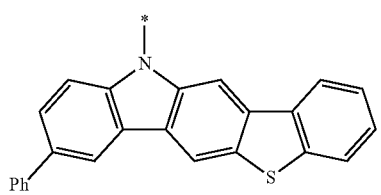
D50

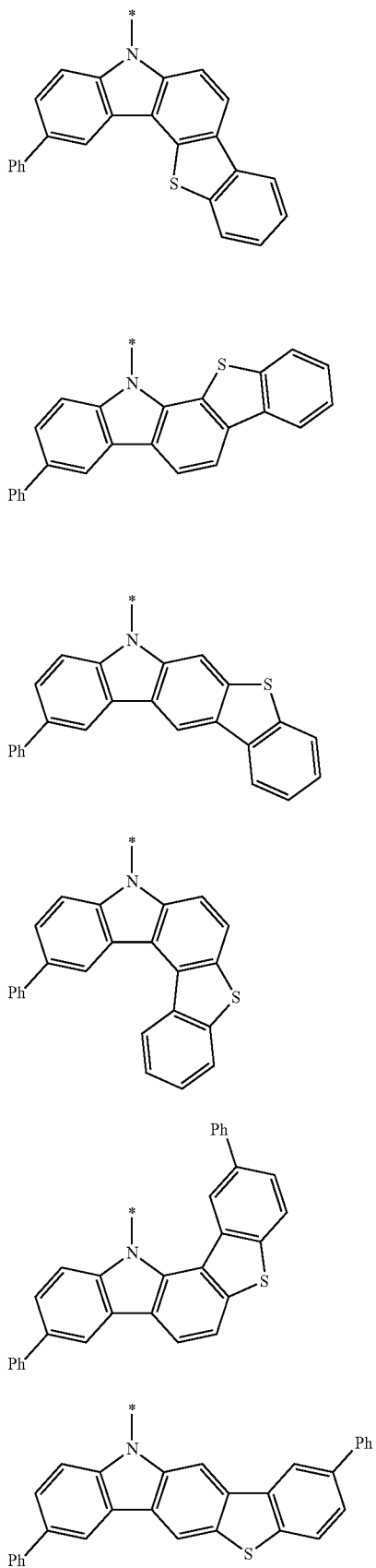
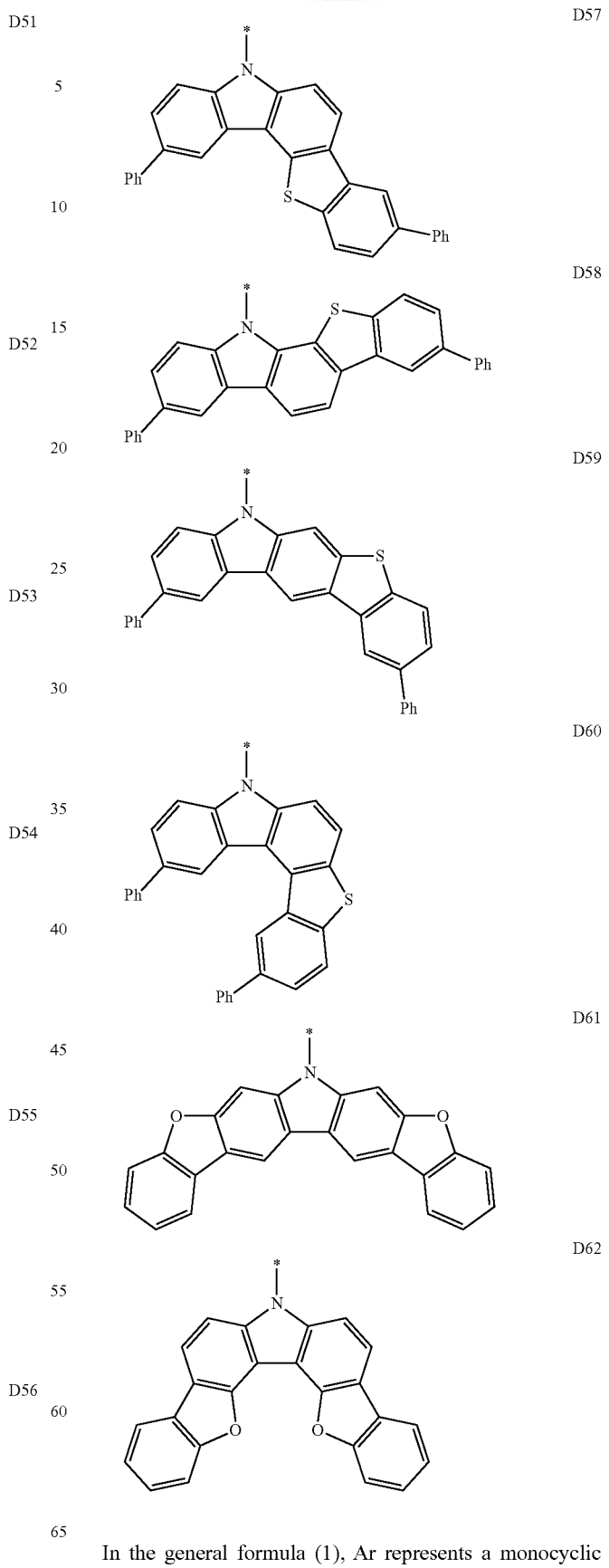
In the general formula (1), Ar represents a monocyclic arylene group or a monocyclic heteroarylene group. A monocyclic arylene group referred to herein means a non-condensed phenylene group. A monocyclic heteroarylene group means a non-condensed, monocyclic structured aromatic ring group, which contains a hetero atom as a ring skeleton-constituting atom. The number of the ring skeleton-constituting atoms of the monocyclic heteroarylene group is preferably 5 to 7, more preferably 5 or 6, and for example, one having 6 such atoms can be employed. Examples of the hetero atom to constitute the ring skeleton of the monocyclic heteroarylene group include a nitrogen atom, an oxygen atom and a sulfur atom, and a nitrogen atom is preferred. The ring to constitute the monocyclic heteroarylene group includes a pyridine ring, a pyridazine ring, a pyrimidine ring, a pyrazine ring, and a triazine ring.

When the carbazole expressed on the right side in the general formula (1) bonds to the 1-position of the single ring that constitutes Ar, the benzofuran expressed on the left side in the general formula (1) may bond to any position of the single ring to constitute Ar. Preferably, the dibenzofuran bonds to the 3-position or the 4-position of the single ring to constitute Ar. In one preferred embodiment of the invention, the dibenzofuran bonds to the 3-position of the single ring to constitute Ar (for example, Ar is a substituted or unsubstituted 1,3-phenylene group).

The monocyclic arylene group and the monocyclic heteroarylene group that Ar can take each may be substituted with a substituent not containing a cyano group. In one preferred embodiment of the invention, as the substituent, a group having a Hammett's σp value that falls within a range of −0.3 to 0.3 is selected. Regarding the description and the preferred range of the substituent having a Hammett's σp value that falls within a range of −0.3 to 0.3, reference can be made to the corresponding description of $R^1$ to $R^5$. In one embodiment of the invention, a group not having an unshared electron pair is selected as the substituent. In one embodiment of the invention, a group not having a n-electron is selected as the substituent. In one preferred embodiment of the invention, one group or a combination of two or more groups selected from the group consisting of an alkyl group (for example, having 1 to 40 carbon atoms) and an aryl group (for example, having 6 to 30 carbon atoms) is selected as the substituent. In one preferred embodiment of the invention, an alkyl group having 1 to 30 carbon atoms is selected as the substituent. Regarding the description and the preferred range of the alkyl group, reference can be made to the corresponding description of $R^1$ to $R^5$.

In one preferred embodiment of the invention, Ar is a phenylene group optionally substituted with one to four alkyl groups each having 1 to 20 carbon atoms, or a monocyclic heteroarylene group optionally substituted with one to three alkyl groups each having 1 to 20 carbon atoms. In one preferred embodiment of the invention, Ar is an unsubstituted phenylene group or an unsubstituted monocyclic heteroarylene group.

Specific examples of Ar in the general formula (1) are shown below, but the structure employable in the invention should not be limitatively interpreted by these specific examples. t-Bu represents a tert-butyl group, and Ph represents an unsubstituted phenyl group.

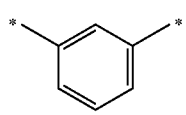

Ar1

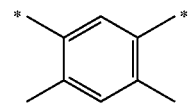

Ar2

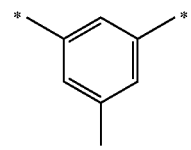

Ar3

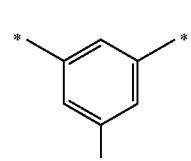

Ar4

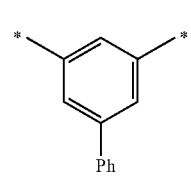

Ar5

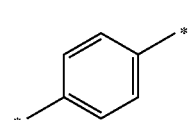

Ar6

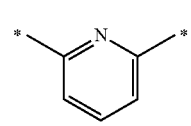

Ar7

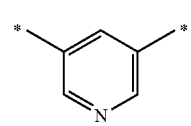

Ar8

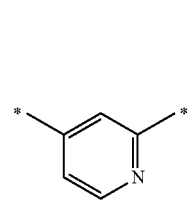

Ar9

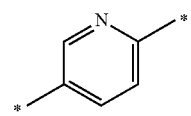

Ar10

The dibenzofuran expressed on the left side of the general formula (1) can bond to Ar at any of the 1- to 4-positions. In one preferred embodiment of the invention, the dibenzofuran bonds to Ar at the 2-position. In one embodiment of the invention, the dibenzofuran bonds to Ar at the 1-position. In one embodiment of the invention, the dibenzofuran bonds to Ar at the 3-position. In one embodiment of the invention, the dibenzofuran bonds to Ar at the 4-position. The 1- to 4-positions of the dibenzofuran are as shown below.

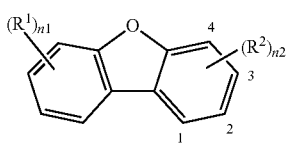

Specific examples of the dibenzofuranyl group bonding to Ar in the general formula (1) are shown below, but the structure employable in the invention should not be limitatively interpreted by these specific examples.

B1

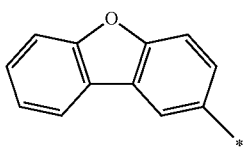

B2

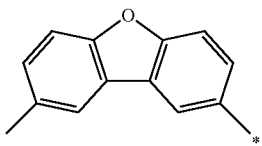

B3

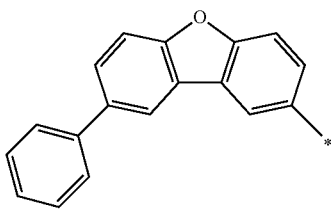

B4

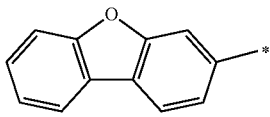

B5

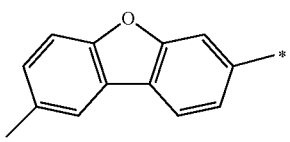

B6

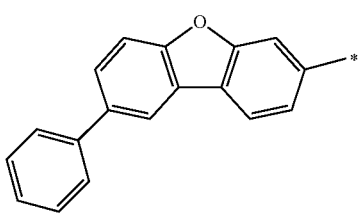

B7

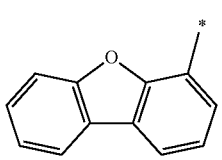

B8

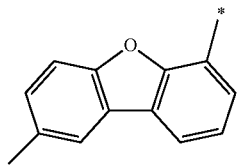

B9

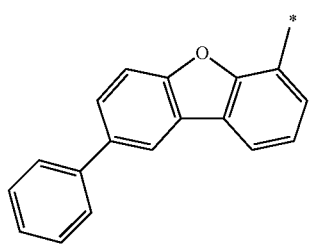

B10

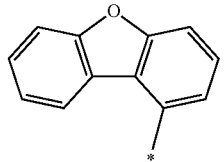
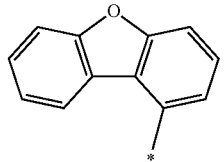

B11

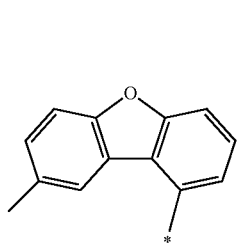
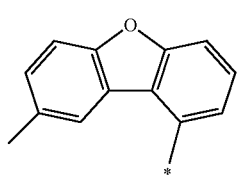

B12

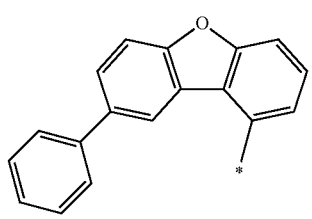
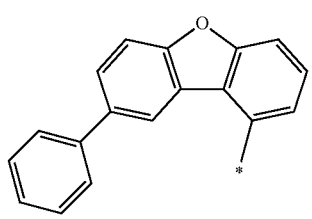

In the general formula (1), a cyano group is not present. In one preferred embodiment of the invention, the general formula (1) is composed of a carbon atom, a hydrogen atom, a nitrogen atom, an oxygen atom and a sulfur atom alone. In one preferred embodiment of the invention, the general formula (1) is composed of a carbon atom, a hydrogen atom, a nitrogen atom and an oxygen atom alone. The molecular weight of the compound represented by the general formula (1) is 499 or more, and is preferably 700 or less, more preferably 600 or less, and can be, for example, 550 or less, or 530 or less.

A compound represented by the following general formula (2) can be preferably exemplified as the compound represented by the general formula (1).

General Formula (2)

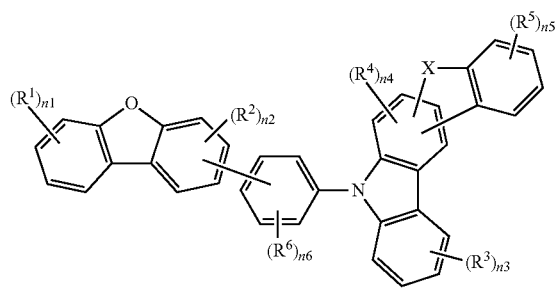

A compound represented by the following general formula (3) can be preferably exemplified as the compound represented by the general formula (1).

General Formula (3)

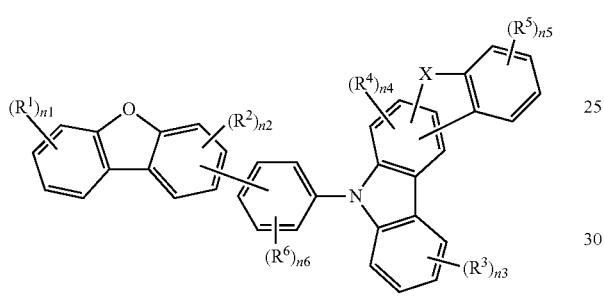

Regarding the definition and the description of R¹ to R⁵, n1 to n5, and X in the general formula (2) and the general formula (3), reference can be made to the corresponding definition and description of the general formula (1).

Regarding the definition and the description of R⁶ in the general formula (2) and the general formula (3), reference can be made to the definition and the description of R¹ to R⁵ in the general formula (1). n6 in the general formula (2) and the general formula (3) is an integer of any of 0 to 3. n6 can be selected within a range of 0 to 2, or can be 0 or 1, and is preferably 0. n1 to n6 in the general formula (2) and the general formula (3) can be each independently selected within a range of 0 to 2, or can be 0 or 1. n1 to n6 can be all 0.

Specific examples of the compound represented by the general formula (1) are shown below, but the compound employable in the invention should not be limitatively interpreted by these specific examples.

Compound 1

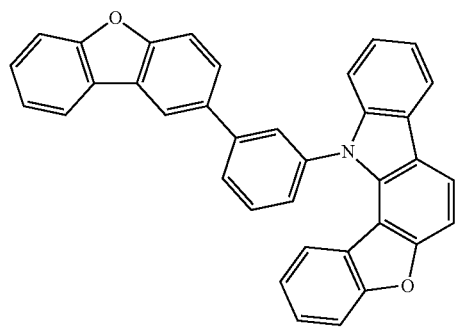

Compound 2

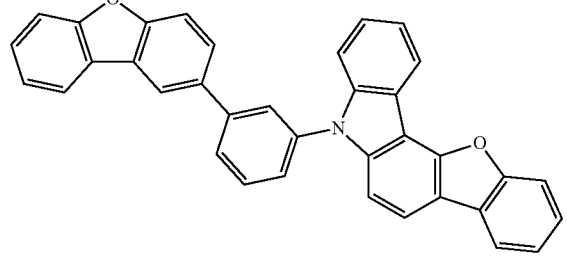

Compound 3

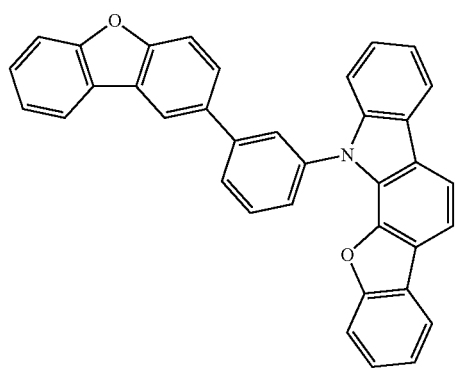

Compound 4

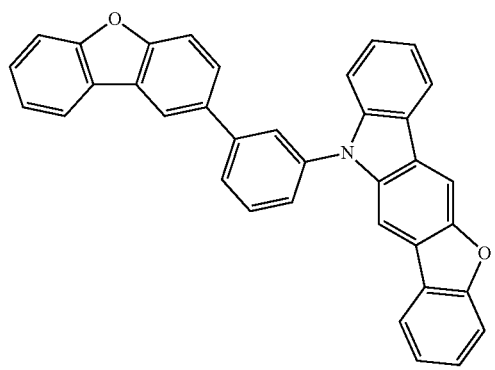

Compound 5

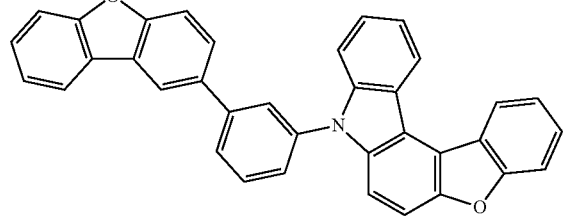

Compound 6
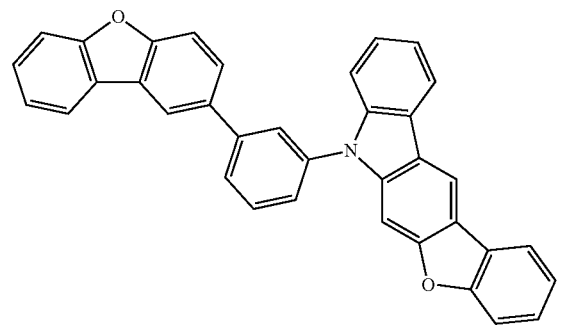
Compound 7
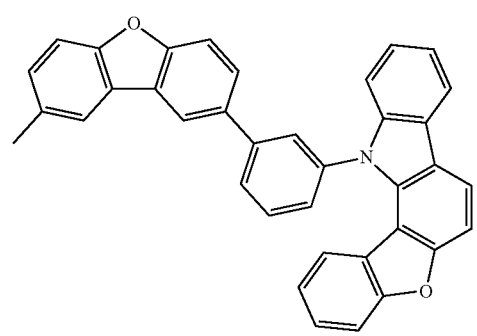
Compound 8
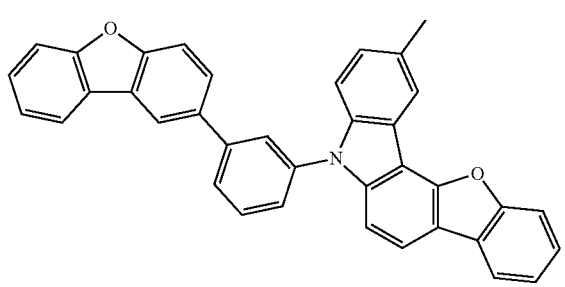
Compound 9
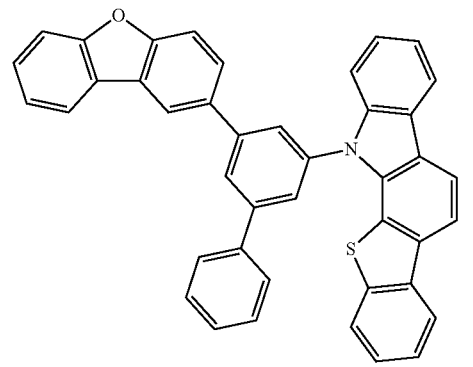
Compound 10
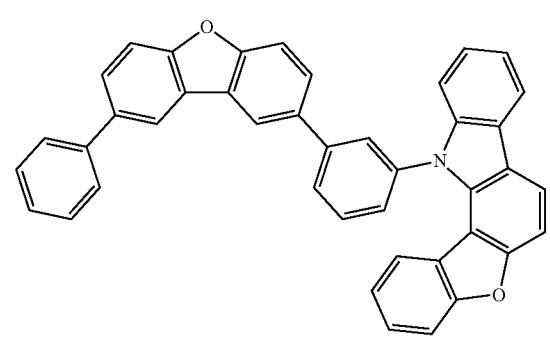
Compound 11
Compound 12
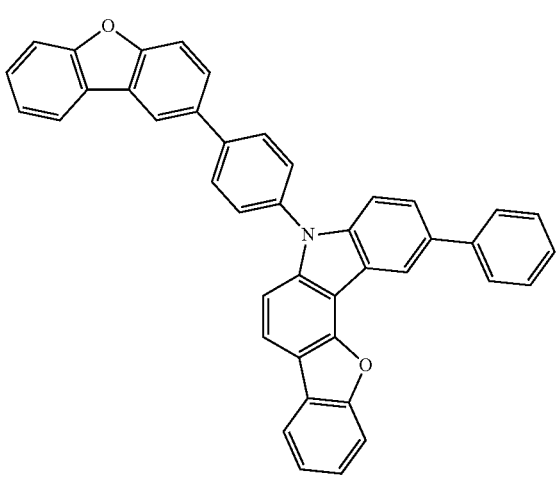
Compound 13
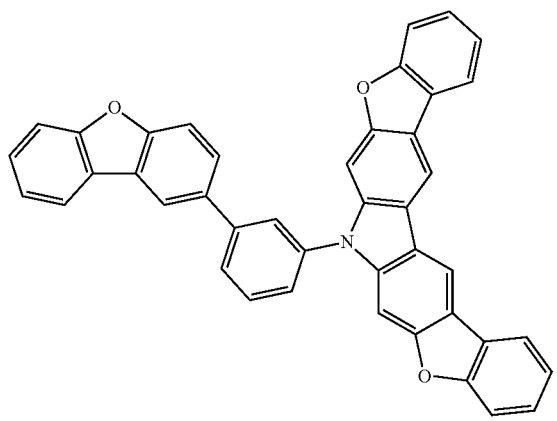

-continued

Compound 14

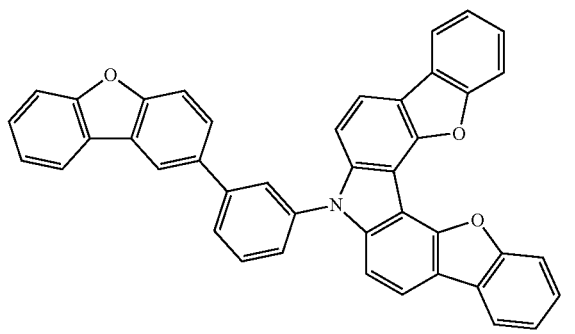

(Delayed Fluorescent Material)

The compound represented by the general formula (1) is useful as a host material for use along with a delayed fluorescent material.

"Delayed fluorescent material" as referred to herein is an organic compound which, in an excited state, undergoes reverse intersystem crossing from an excited triplet state to an excited singlet state, and which emits delayed fluorescence in returning back from the excited singlet state to a ground state. In the invention, a compound which gives fluorescence having an emission lifetime of 100 ns (nanoseconds) or longer, when the emission lifetime is measured with a fluorescence lifetime measuring system (e.g., streak camera system by Hamamatsu Photonics KK), is referred to as a delayed fluorescent material.

When the compound represented by the general formula (1) is used as combined with a delayed fluorescent material, the delayed fluorescent material receives energy from the compound represented by the general formula (1) in an excited singlet state to transition into an excited singlet state. Also, the delayed fluorescent material can receive energy from the compound of the general formula (1) in an excited triplet state to transition into an excited triplet state. Of the delayed fluorescent material, the difference between the excited singlet energy and the excited triplet energy ($\Delta E_{ST}$) is small, and therefore a delayed fluorescent material in an excited triplet state can readily undergo reverse intersystem crossing to be a delayed fluorescent material in an excited singlet state. The delayed fluorescent material in an excited singlet state formed through these routes can contribute toward light emission.

The delayed fluorescent material is preferably such that the difference $\Delta E_{st}$ between the lowest excited singlet energy level and the lowest excited triplet energy level at 77K is 0.3 eV or less, more preferably 0.25 eV or less, even more preferably 0.2 eV or less, further more preferably 0.15 eV or less, further more preferably 0.1 eV or less, further more preferably 0.07 eV or less, further more preferably 0.05 eV or less, further more preferably 0.03 eV or less, further more preferably 0.01 eV or less.

When $\Delta E_{st}$ is smaller, reverse intersystem crossing from an excited singlet state to an excited triplet state can more readily occur through thermal energy absorption, and therefore the compound of the type can function as a thermal activation type delayed fluorescent material. A thermal activation type delayed fluorescent material can absorb heat generated by a device to relatively readily undergo reverse intersystem crossing from an excited triplet state to an excited singlet state, and can make the excited triplet energy efficiently contribute toward light emission.

In the invention, a lowest excited singlet energy level ($E_{S1}$) and a lowest excited triplet energy level ($E_{T1}$) of a compound are determined according to the following process. $\Delta E_{ST}$ is a value determined by calculating $E_{S1}$-$E_{T1}$.

(1) Lowest Excited Singlet Energy ($E_{S1}$)

A thin film or a toluene solution (concentration: $10^{-5}$ mol/L) of the targeted compound is prepared as a measurement sample. The fluorescent spectrum of the sample is measured at room temperature (300 K). For the fluorescent spectrum, the emission intensity is on the vertical axis and the wavelength is on the horizontal axis. A tangent line is drawn to the rising of the emission spectrum on the short wavelength side, and the wavelength value λedge [n] at the intersection between the tangent line and the horizontal axis is read. The wavelength value is converted into an energy value according to the following conversion expression to calculate $E_{S1}$.

$E_{S1}[eV]=1239.85/\lambda\text{edge}$    Conversion Expression:

For the measurement of the emission spectrum in Examples given below, an LED light source (by Thorlabs Corporation, M300L4) was used as an excitation light source along with a detector (by Hamamatsu Photonics K.K., PMA-12 Multichannel Spectroscope C10027-01).

(2) Lowest Excited Triplet Energy ($E_{T1}$)

The same sample as that for measurement of the lowest excited singlet energy ($E_{S1}$) is cooled to 77 [K] with liquid nitrogen, and the sample for phosphorescence measurement is irradiated with excitation light (300 nm), and using a detector, the phosphorescence thereof is measured. The emission after 100 milliseconds from irradiation with the excitation light is drawn as a phosphorescent spectrum. A tangent line is drawn to the rising of the phosphorescent spectrum on the short wavelength side, and the wavelength value λedge [nm] at the intersection between the tangent line and the horizontal axis is read. The wavelength value is converted into an energy value according to the following conversion expression to calculate $E_{T1}$.

$E_{T1}[eV]=1239.85/\lambda\text{edge}$    Conversion Expression:

The tangent line to the rising of the phosphorescent spectrum on the short wavelength side is drawn as follows. While moving on the spectral curve from the short wavelength side of the phosphorescent spectrum toward the maximum value on the shortest wavelength side among the maximum values of the spectrum, a tangent line at each point on the curve toward the long wavelength side is taken into consideration. With rising thereof (that is, with increase in the vertical axis), the inclination of the tangent line increases. The tangent line drawn at the point at which the inclination value has a maximum value is referred to as the tangent line to the rising on the short wavelength side of the phosphorescent spectrum.

The maximum point having a peak intensity of 10% or less of the maximum peak intensity of the spectrum is not included in the maximum value on the above-mentioned shortest wavelength side, and the tangent line drawn at the point which is closest to the maximum value on the shortest wavelength side and at which the inclination value has a maximum value is referred to as the tangent line to the rising on the short wavelength side of the phosphorescent spectrum.

In one preferred embodiment of the invention, a compound having a cyanobenzene structure in which the number of the cyano group substituting on the benzene ring is one (a cyanobenzene derivative) is used as the delayed fluorescent material. In another preferred embodiment of the invention, a compound having a dicyanobenzene structure in which the number of the cyano groups substituting on the benzene ring is two (a dicyanobenzene derivative) is used as the delayed fluorescent material. In another preferred embodiment of the invention, a compound having an azabenzene structure in which at least one ring skeleton-constituting carbon atom of the benzene ring is replaced with a nitrogen atom (an azabenzene derivative) is used as the delayed fluorescent material.

In one preferred embodiment of the invention, a compound represented by the following general formula (4) is used as the delayed fluorescent material

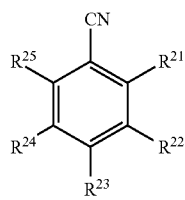

General Formula (4)

In the general formula (4), one of $R^{21}$ to $R^{23}$ represents a cyano group or a group represented by the following general formula (5), the remaining two of $R^{21}$ to $R^{23}$ and at least one of $R^{24}$ and $R^{25}$ each represent a group represented by the following general formula (6), the remaining $R^{21}$ to $R^{25}$ each represent a hydrogen atom or a substituent (provided that the substituent as referred to herein is not a cyano group, a group represented by the following formula (5) and a group represented by the following formula (6).

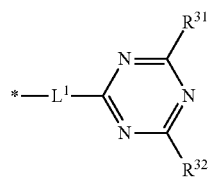

General Formula (5)

In the general formula (5), $L^1$ represents a single bond or a divalent linking group, $R^{31}$ and $R^{32}$ each independently represent a hydrogen atom or a substituent, * indicates a bonding position.

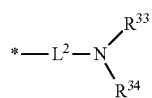

General Formula (6)

In the general formula (6). $L^2$ represents a single bond or a divalent linking group, $R^{33}$ and $R^{34}$ each independently represent a hydrogen atom or a substituent, * indicates a bonding position.

In one preferred embodiment of the invention, $R^{22}$ is a cyano group. In one preferred embodiment of the invention. $R^{22}$ is a group represented by the general formula (5). In one embodiment of the invention, $R^{21}$ is a cyano group or a group represented by the general formula (5). In one embodiment of the invention, $R^{23}$ is a cyano group or a group represented by the general formula (5). In one embodiment of the invention, one of $R^{21}$ to $R^{23}$ is a cyano group. In one embodiment of the invention, one of $R^{21}$ to $R^{23}$ is a group represented by the general formula (5).

In one preferred embodiment of the invention, $L^1$ in the general formula (5) is a single bond. In one embodiment of the invention. $L^1$ is a divalent linking group, preferably a substituted or unsubstituted arylene group, or a substituted or unsubstituted heteroarylene group, more preferably a substituted or unsubstituted arylene group, even more preferably a substituted or unsubstituted 1,4-phenylene group (the substituent is, for example, an alkyl group having 1 to 3 carbon atoms).

In one embodiment of the invention, $R^{31}$ and $R^{32}$ in the general formula (5) each are independently one group or a combination of two or more groups selected from the group consisting of an alkyl group (for example, having 1 to 40 carbon atoms), an aryl group (for example, having 6 to 30 carbon atoms, a heteroaryl group (for example, the number of the ring skeleton-constituting atoms thereof is 5 to 30), an alkenyl group (for example, having 2 to 40 carbon atoms) and an alkynyl group (for example, having 2 to 40 carbon atoms) (hereinunder these groups will be referred to as "group of substituent group A"). In one preferred embodiment of the invention, $R^{31}$ and $R^{32}$ each are independently a substituted or unsubstituted aryl group (for example, having 6 to 30 carbon atoms), and the substituent for the aryl group includes the groups of the substituent group A. In one preferred embodiment of the invention. $R^{31}$ and $R^{32}$ are the same.

In one preferred embodiment of the invention, $L^2$ in the general formula (6) is a single bond. In one embodiment of the invention, $L^2$ is a divalent linking group, preferably a substituted or unsubstituted arylene group, or a substituted or unsubstituted heteroarylene group, more preferably a substituted or unsubstituted arylene group, even more preferably a substituted or unsubstituted 1,4-phenylene group (the substituent is, for example, an alkyl group having 1 to 3 carbon atoms).

In one embodiment of the invention, $R^{33}$ and $R^{34}$ in the general formula (6) each are independently a substituted or unsubstituted alkyl group (for example, having 1 to 40 carbon atoms), a substituted or unsubstituted alkenyl group (for example, having 1 to 40 carbon atoms), a substituted or unsubstituted aryl group (for example, having 6 to 30 carbon atoms), or a substituted or unsubstituted heteroaryl group (for example, having 5 to 30 carbon atoms). Here, the substituent for the alkyl group, the alkenyl group, the aryl group and the heteroaryl group includes one group or a combination of two or more groups selected from the group consisting of a hydroxy group, a halogen atom (for example, a fluorine atom, a chlorine atom, a bromine atom, an iodine atom), an alkyl group (for example, having 1 to 40 carbon atoms), an alkoxy group (for example, having 1 to 40 carbon atoms), an alkylthio group (for example, having 1 to 40 carbon atoms), an aryl group (for example, having 6 to 30 carbon atoms), an aryloxy group (for example, having 6 to 30 carbon atoms), an arylthio group (for example, having 6 to 30 carbon atoms), a heteroaryl group (for example, the number of the ring skeleton-constituting atoms therein is 5 to 30), a heteroaryloxy group (for example, the number of the ring skeleton-constituting atoms therein is 5 to 30), a heteroarylthio group (for example, the number of the ring skeleton-constituting atoms therein is 5 to 30), an acyl group (for example, having 1 to 40 carbon atoms), an alkenyl group (for example, having 1 to 40 carbon atoms), an alkynyl group (for example, having 1 to 40 carbon atoms, an alkoxycarbonyl group (for example, having 2 to 40 carbon atoms), an aryloxycarbonyl group (for example, having 7 to 40 carbon atoms), a heteroaryloxycarbonyl group (for example, having 4 to 40 carbon atoms), a silyl group (for example, a trialkylsilyl group having 3 to 40 carbon atoms), a nitro group and a cyano group (hereinunder these groups will be referred to as "group of substituent group B").

$R^{33}$ and $R^{34}$ can bond to each other via a single bond or a linking group to form a cyclic structure. In particular, in the case where $R^{33}$ and $R^{34}$ each are an aryl group, preferably, these bond to each other via a single bond or a linking group to form a cyclic structure. The linking group as referred to herein includes —O—, —S—, —N($R^{35}$)—, —C($R^{36}$)($R^{37}$)—, and —C(=O)—, and —O—, —S—, —N($R^{35}$)—, and —C($R^{36}$)($R^{37}$)— are preferred. —O—, —S—, and —N($R^{35}$)— are more preferred. $R^{35}$ to $R^{37}$ each independently represent a hydrogen atom or a substituent. As the substituent, a group of the above-mentioned substituent group A, or a group of the above-mentioned substituent group B can be selected, and the substituent is preferably one group or a combination of two or more groups selected from the group consisting of an alkyl group having 1 to 10 carbon atoms and an aryl group having 6 to 14 carbon atoms.

The group represented by the general formula (6) is preferably a group represented by the following general formula (7).

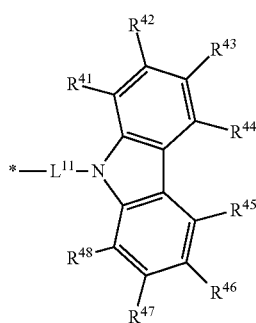

General Formula (7)

In the general formula (7), $L^{11}$ represents a single bond or a divalent linking group. Regarding the description and the preferred range of $L^{11}$, reference can be made to the description and the preferred range of $L^2$ mentioned hereinabove.

In the general formula (7). $R^{41}$ to $R^{48}$ each independently represent a hydrogen atom or a substituent. $R^{41}$ and $R^{42}$, $R^{42}$ and $R^{43}$, $R^{43}$ and $R^{44}$, $R^{44}$ and $R^{45}$, $R^{45}$ and $R^{46}$, $R^{46}$ and $R^{47}$, and $R^{47}$ and $R^{48}$ each may bond to each other to forma cyclic structure. The cyclic structure to be formed by bonding to each other may be an aromatic ring or an aliphatic ring, or may also be one containing a hetero atom, and further, the cyclic structure may be a condensed ring of two or more rings. The hetero atom as referred to herein is preferably selected from the group consisting of a nitrogen atom, an oxygen atom and a sulfur atom. Examples of the cyclic structure to be formed includes a benzene ring, a naphthalene ring, a pyridine ring, a pyridazine ring, a pyrimidine ring, a pyrazine ring, a pyrrole ring, an imidazole ring, a pyrazole ring, an imidazoline ring, an oxazole ring, an isoxazole ring, a thiazole ring, an isothiazole ring, a cyclohexadiene ring, a cyclohexene ring, a cyclopentaene ring, a cycloheptatriene ring, a cycloheptadiene ring, a cycloheptaene ring, a furan ring, a thiophene ring, a naphthyridine ring, a quinoxaline ring, and a quinoline ring. A number of ring may be condensed to form a condensed ring, such as a phenanthrene ring and a triphenylene ring. The number of the rings contained in the group represented by the general formula (7) can be selected from a range of 3 to 5, or from a range of 5 to 7.

The substituent that $R^{41}$ to $R^{48}$ can take includes groups of the above-mentioned substituent group B, and is preferably an unsubstituted alkyl group having 1 to 10 carbon atoms, or an aryl group having 6 to 10 carbon atoms and optionally substituted with an unsubstituted alkyl group having 1 to 10 carbon atoms. In one preferred embodiment of the invention, $R^{41}$ to $R^{48}$ each are a hydrogen atom or an unsubstituted alkyl group having 1 to 10 carbon atoms. In one preferred embodiment of the invention. $R^{41}$ to $R^{48}$ each are a hydrogen atom or an unsubstituted aryl group having 6 to 10 carbon atoms. In one preferred embodiment of the invention, $R^{41}$ to $R^{48}$ are all hydrogen atoms.

In the general formula (7), * indicates a bonding position.

In one preferred embodiment of the invention, an azabenzene derivative is used as the delayed fluorescent material. In one preferred embodiment of the invention, the azabenzene derivative has an azabenzene structure where three ring skeleton-constituting carbon atoms of the benzene ring are replaced with nitrogen atoms. For example, an azabenzene derivative having a 1,3,5-triazine structure is preferably selected. In one preferred embodiment of the invention, the azabenzene derivative has an azabenzene structure where two ring skeleton-constituting carbon atoms of the benzene ring are replaced with nitrogen atoms. Examples of the structure of the azabenzene derivative include a pyridazine structure, a pyrimidine structure and a pyrazine structure. An azabenzene derivative having a pyrimidine structure is preferably selected. In one embodiment of the invention, the azabenzene derivative has a pyridine structure where one ring skeleton-constituting carbon atom of the benzene ring is replaced with a nitrogen atom.

In one preferred embodiment of the invention, a compound represented by the following general formula (8) is used as the delayed fluorescent material.

General Formula (8)

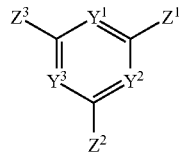

In the general formula (8), at least one of $Y^1$, $Y^2$ and $Y^3$ is a nitrogen atom, and the remaining thereof is a methine group. In one embodiment of the invention, $Y^1$ is a nitrogen atom, $Y^2$ and $Y^3$ are methine groups. Preferably, $Y^1$ and $Y^2$ are nitrogen atoms, and $Y^3$ is a methine group. More preferably, $Y^1$ to $Y^3$ are all nitrogen atoms.

In the general formula (8), $Z^1$ to $Z^3$ each independently represent a hydrogen atom or a substituent, and at least one is a donor substituent. The donor substituent means a group having a negative Hammett's σp value. Preferably, at least one of $Z^1$ to $Z^3$ is a group containing a diarylamino structure (where the two aryl groups bonding to the nitrogen atom may bond to each other), more preferably a group represented by the general formula (6), and is, for example, a group represented by the general formula (7). In one embodiment of the invention, only one of $Z^1$ to $Z^3$ is a group represented by the general formula (6) or (7). In one embodiment of the invention, two of $Z^1$ to $Z^3$ each are independently a group represented by the general formula (6) or (7). In one embodiment of the invention, all $Z^1$ to $Z^3$ each are independently a group represented by the general formula (6) or (7). Regarding the details and the preferred range of the general formula (6) and the general formula (7), reference can be made to the corresponding description given hereinabove. The remaining $Z^1$ to $Z^3$ that are not groups represented by the general formula (6) and the general formula (7) are preferably a substituted or unsubstituted aryl group (for example, having 6 to 40, preferably 6 to 20 carbon atoms). Examples of the substituent for the aryl group referred to herein include one group or a combination of two or more kinds of groups selected from the group consisting of an aryl group (for example, having 6 to 20, preferably 6 to 14 carbon atoms) and an alkyl group (for example, having 1 to 20, preferably 1 to 6 carbon atoms). In one embodiment of the invention, the general formula (8) does not contain a cyano group.

In one preferred embodiment of the invention, a compound represented by the following general formula (9) is used as the delayed fluorescent material.

General Formula (9)

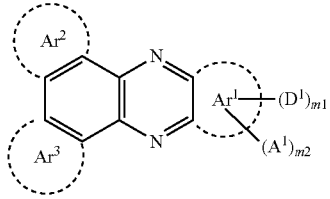

In the general formula (9), $Ar^1$ forms a cyclic structure that can be substituted with the following $A^1$ and $D^1$, representing a benzene ring, a naphthalene ring, an anthracene ring or a phenanthrene ring. $Ar^2$ and $Ar^3$ each may form a cyclic structure, and the cyclic structure to be formed is a benzene ring, a naphthalene ring, a pyridine ring or a benzene ring substituted with a cyano group. m1 represents an integer of any of 0 to 2, m2 represents an integer of any of 0 to 1. $A^1$ represents a cyano group, a phenyl group, a pyrimidyl group, a triazyl group, or a benzonitrile group. $D^1$ represents a substituted or unsubstituted 5H-indole[3,2,1-de]phenazin-5-yl group, or a substituted or unsubstituted heteroring-condensed carbazolyl group not containing a naphthalene structure, and in the case where plural $D^1$'s exist in the general formula (9), they may be the same or different. The substituents of $D^1$ may bond to each other to form a cyclic structure.

Preferred compounds for use as the delayed fluorescent material are mentioned below, but the delayed fluorescent material usable in the invention should not be limitatively interpreted by these specific examples.

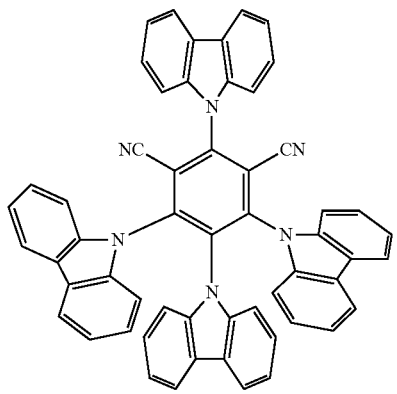

TADF1

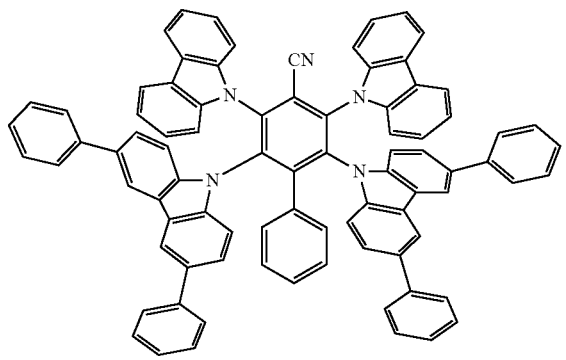

TADF2

-continued
TADF3
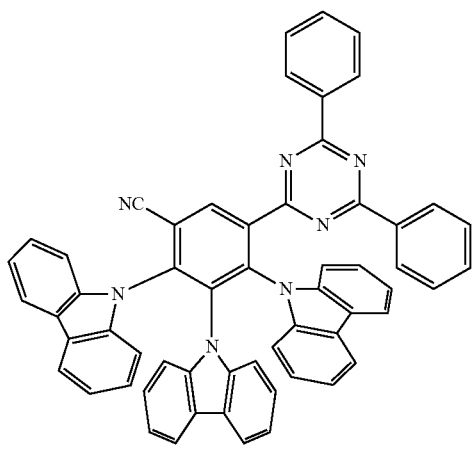
TADF4
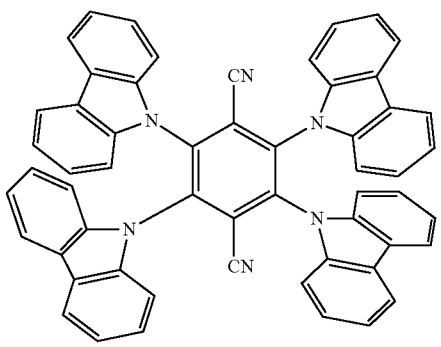
TADF5
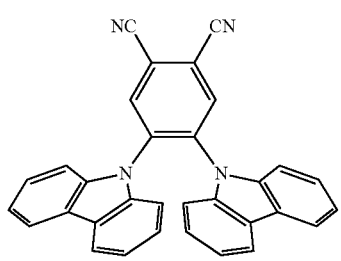
TADF6
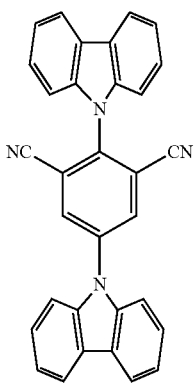
TADF7
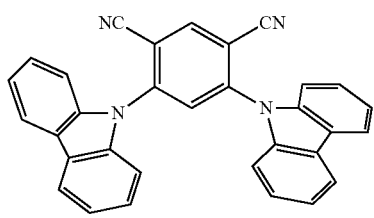
TADF8
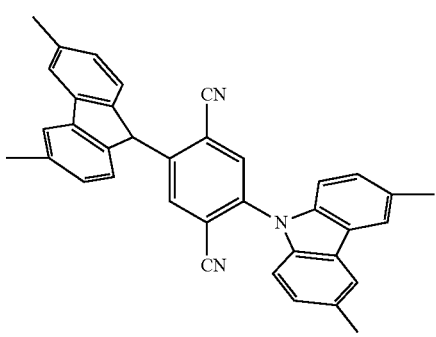
TADF9
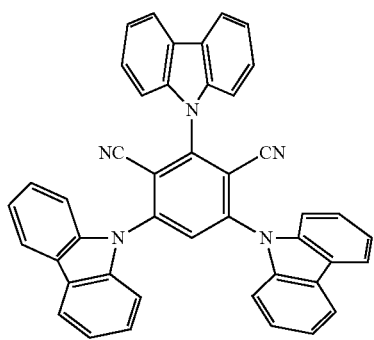
TADF10
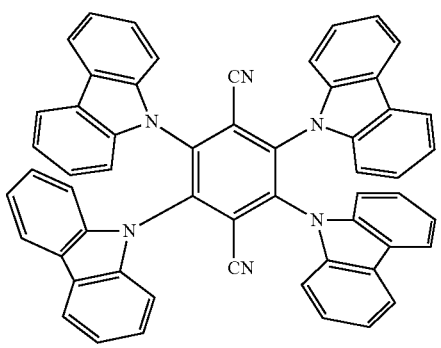

-continued
TADF11
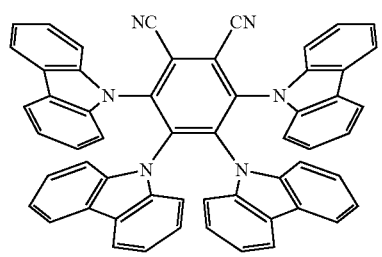
TADF12
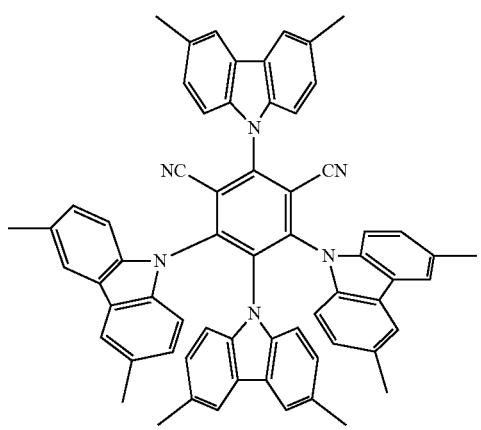
TADF13
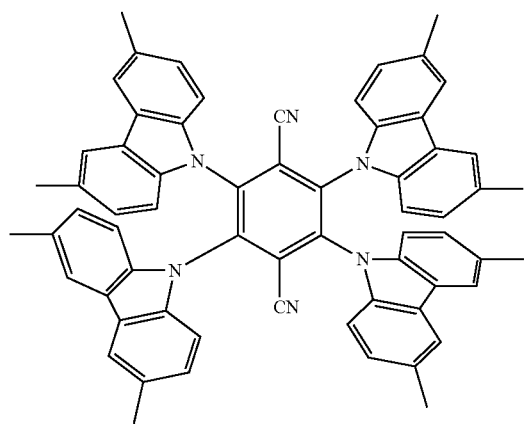
TADF14
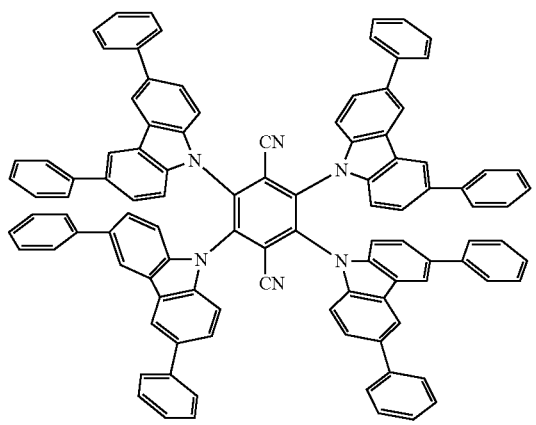
TADF15
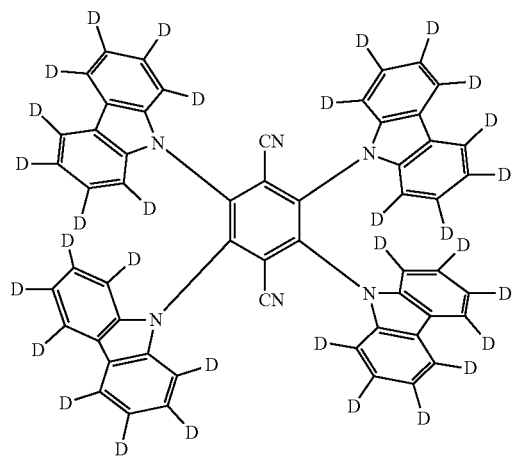
TADF16
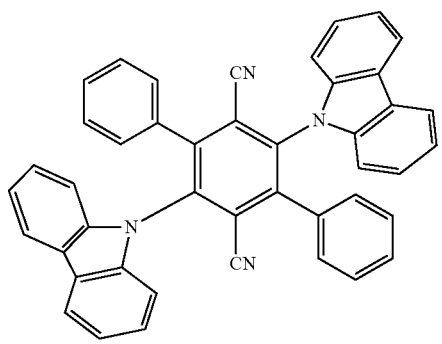

-continued
TADF17
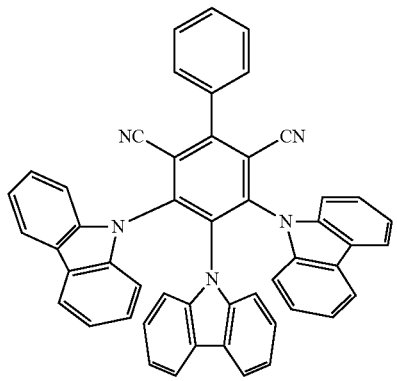
TADF18
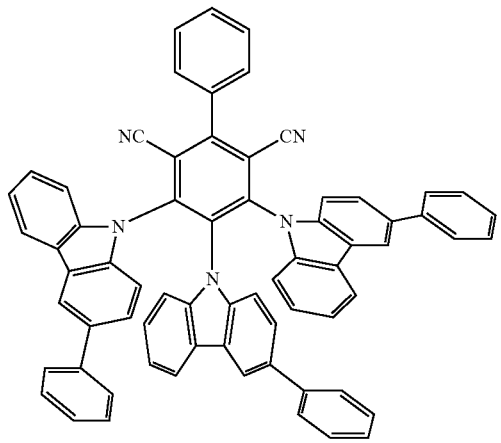
TADF19
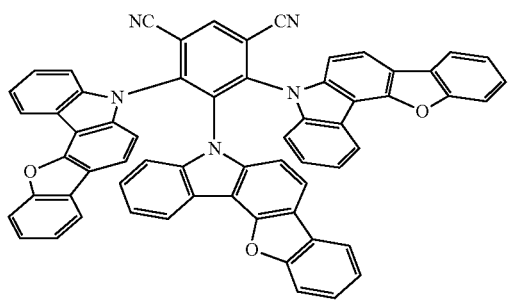
TADF20
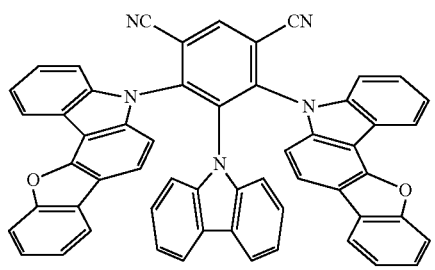
TADF21
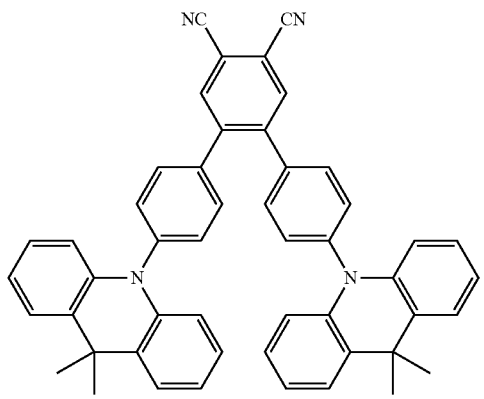
TADF22
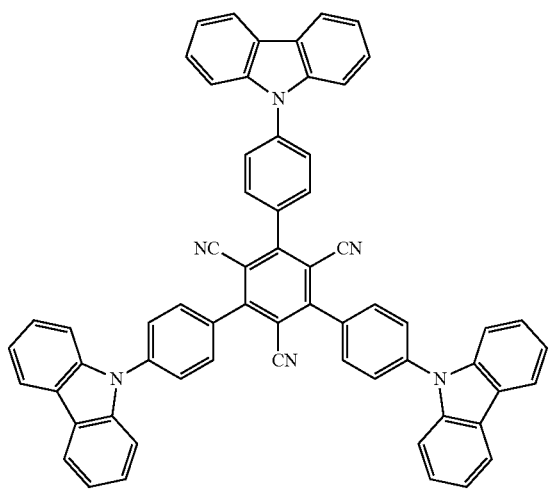
TADF23
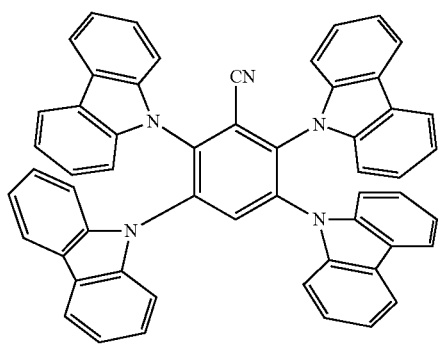
TADF24
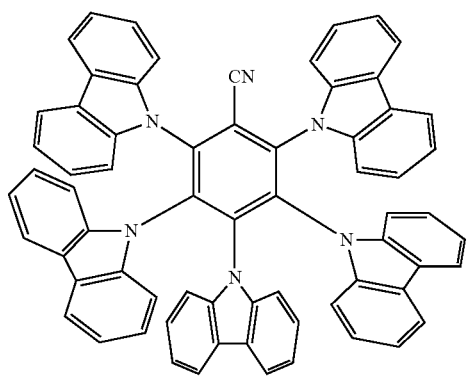

-continued
TADF25
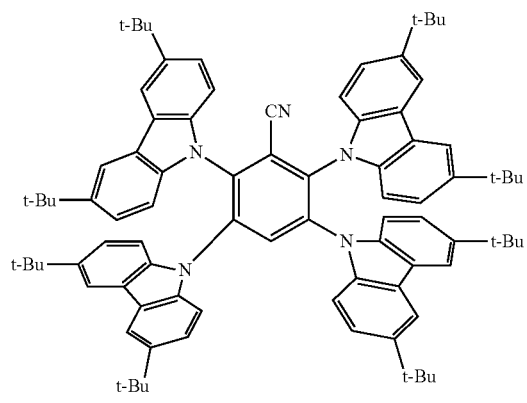
TADF26
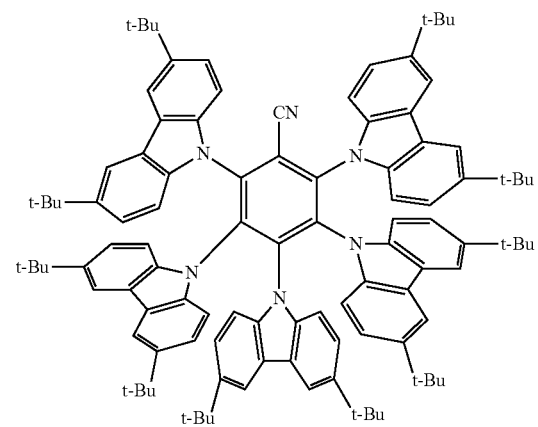
TADF27
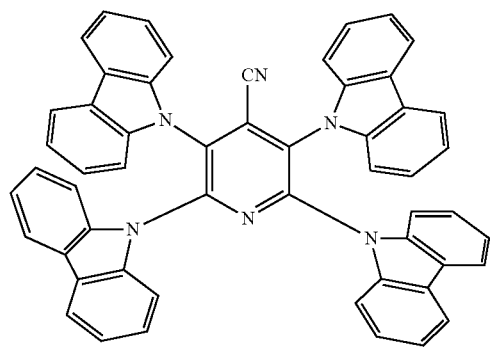
TADF28
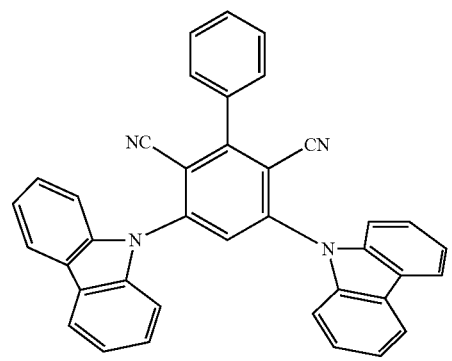
TADF29
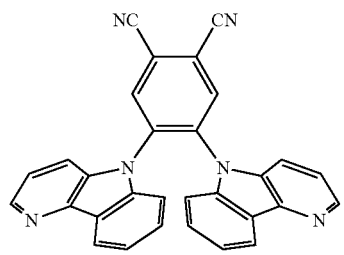
TADF30
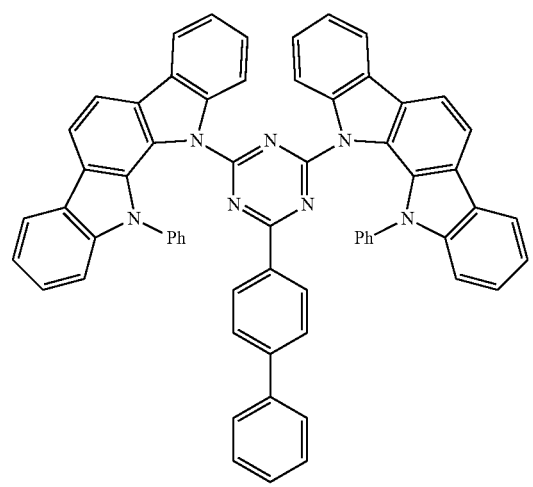

-continued
TADF31
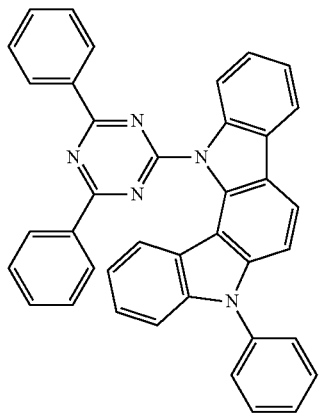 [SMILES: c1ccc(-c2nc(-c3ccccc3)nc(-n3c4ccccc4c4ccc5c(c6ccccc6n5-c5ccccc5)c43)n2)cc1]
TADF32
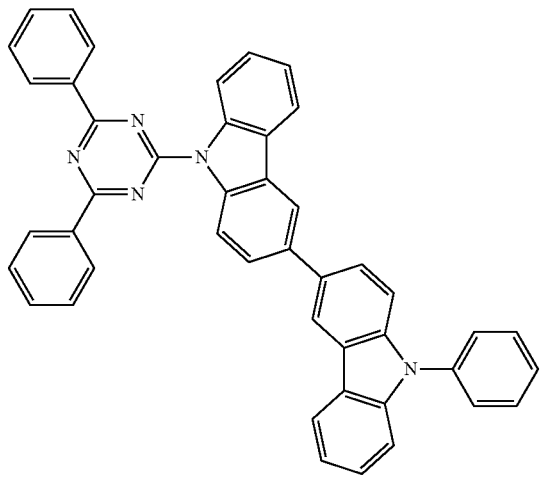
TADF33
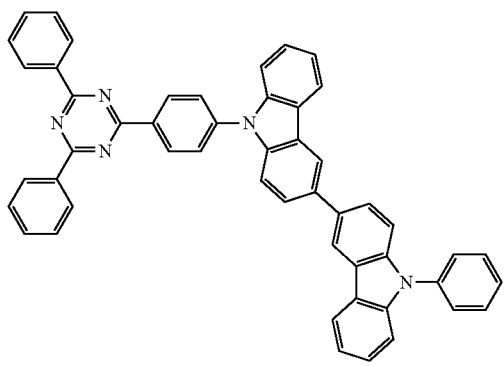
TADF34
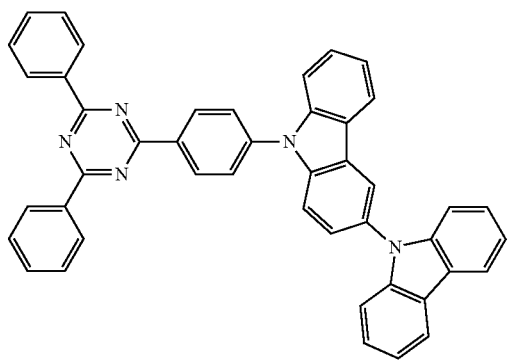
TADF35
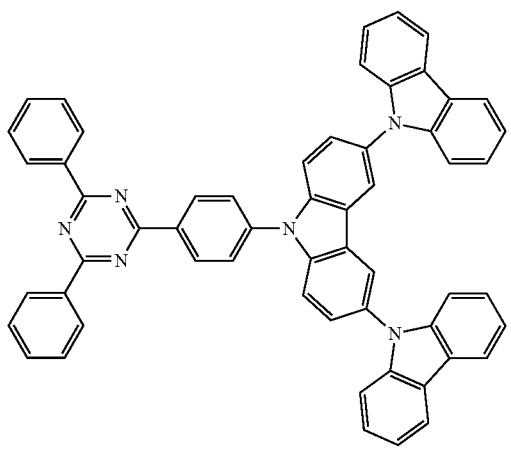
TADF36
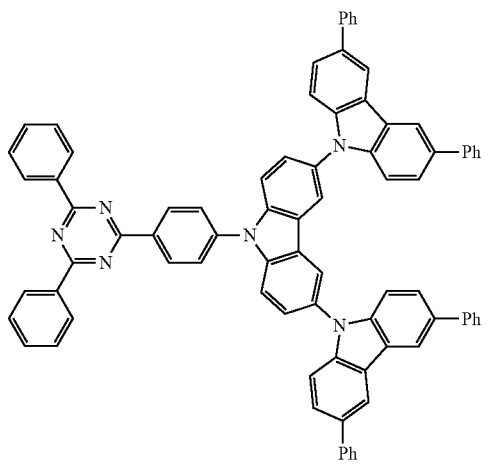

-continued
TADF37
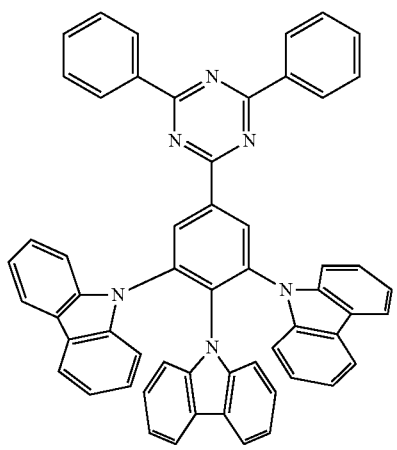
TADF38
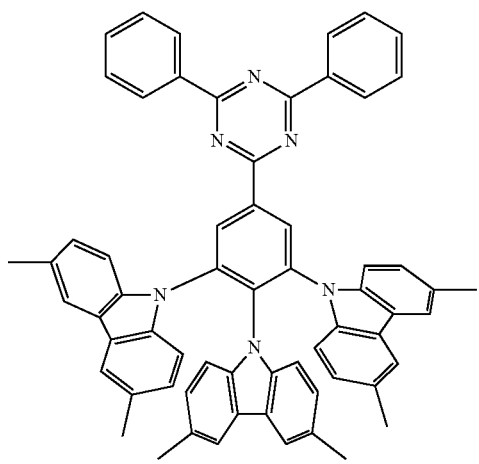
TADF39
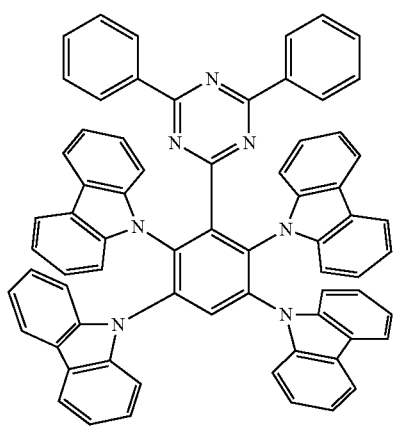
TADF40
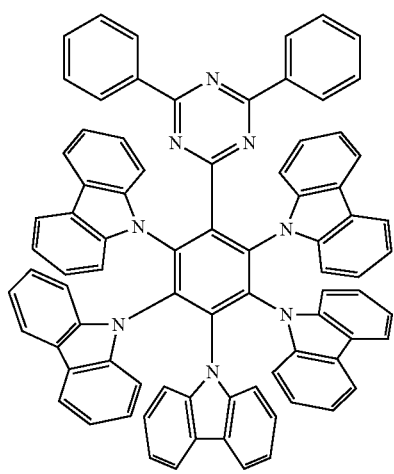
TADF41
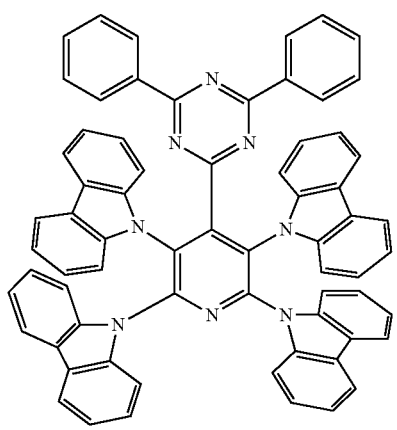
TADF42
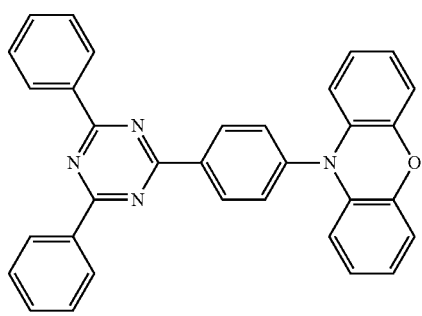

-continued
TADF43
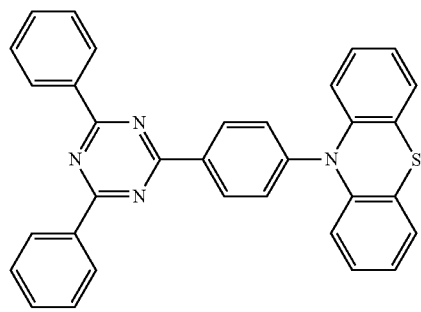
TADF44
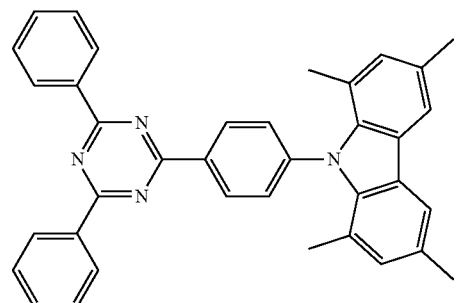
TADF45
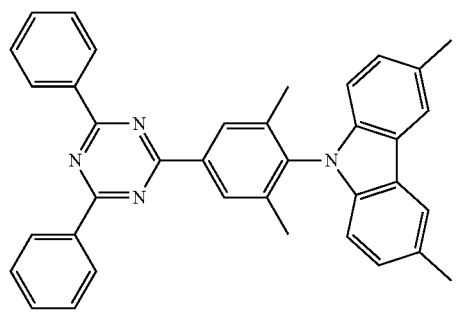
TADF46
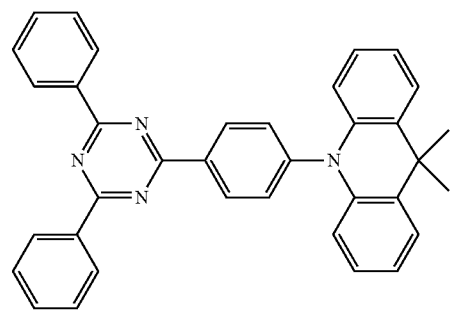
TADF47
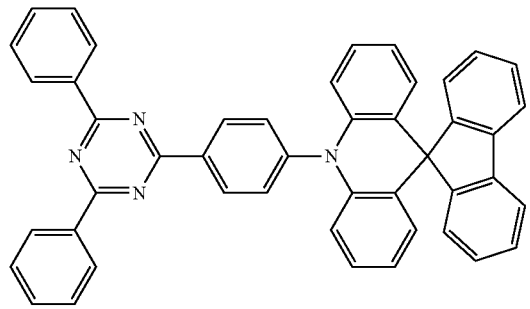
TADF48
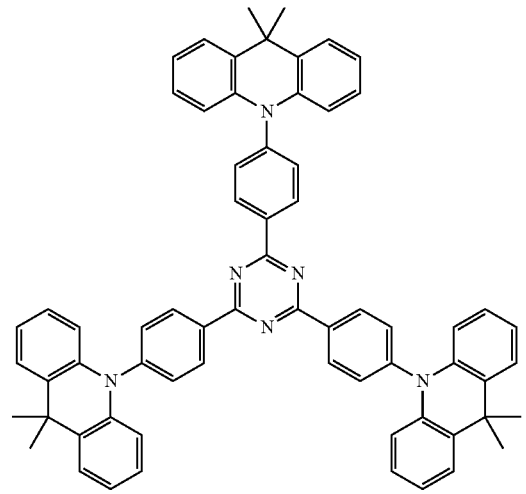
TADF49
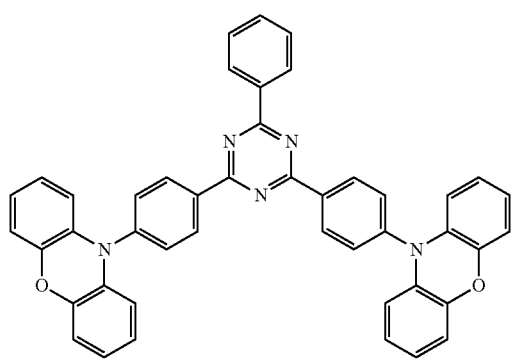
TADF50
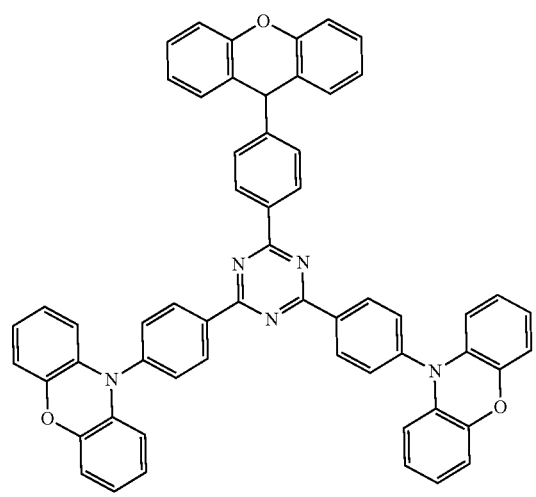

TADF51
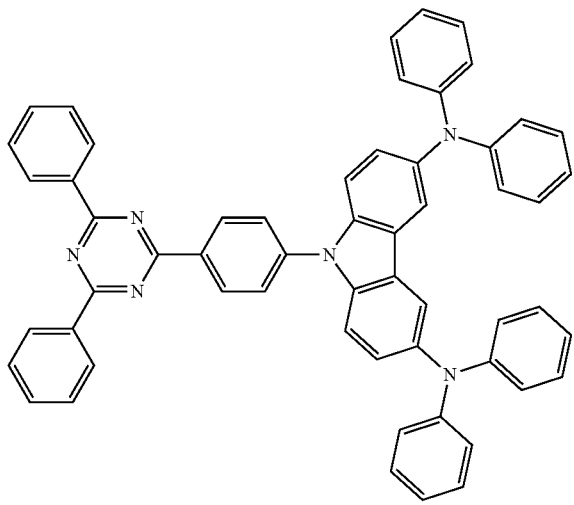
TADF52
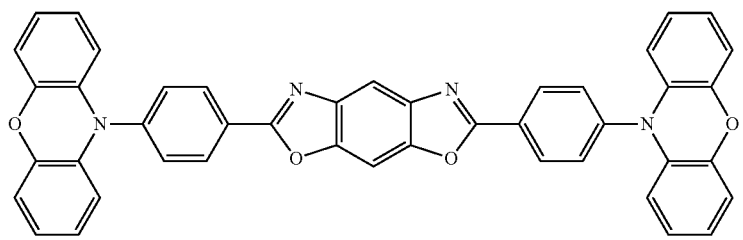
TADF53
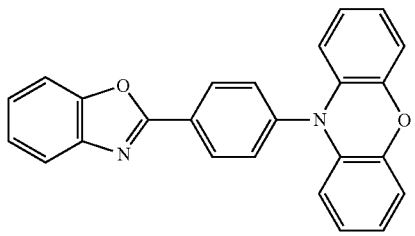
TADF54
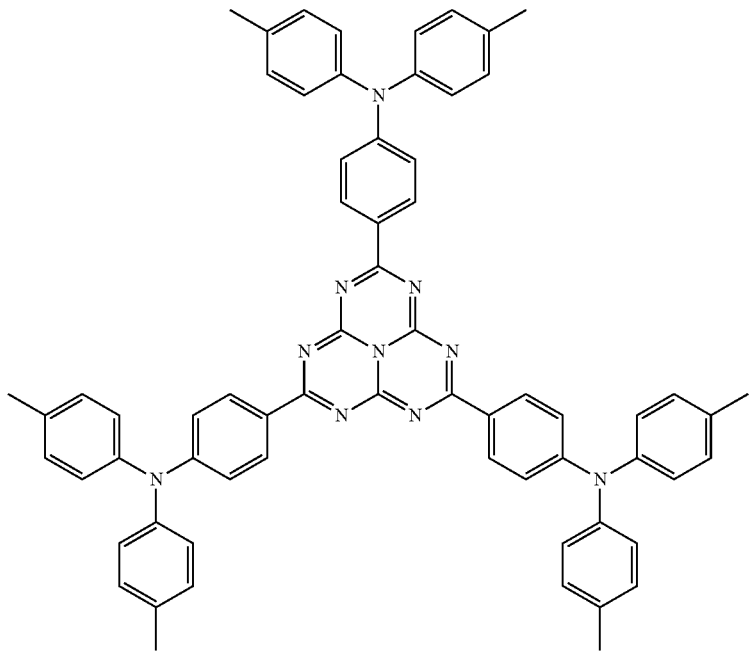

TADF55
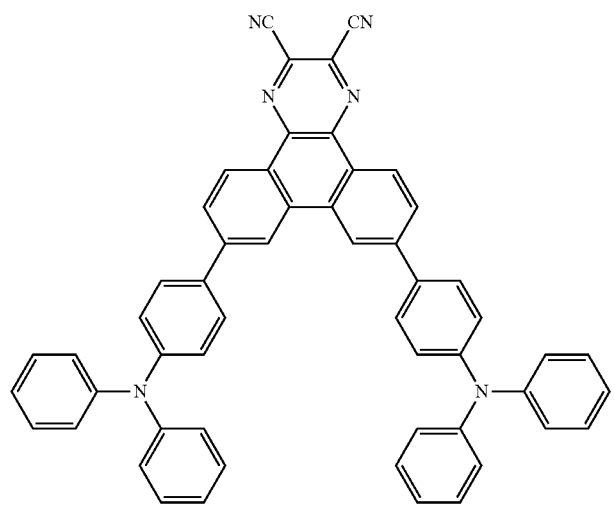
TADF56
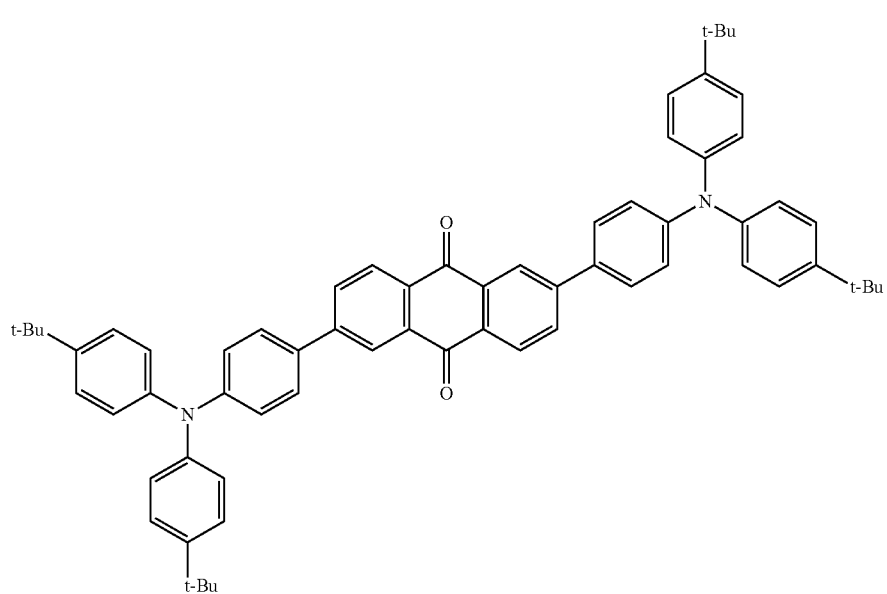
TADF57
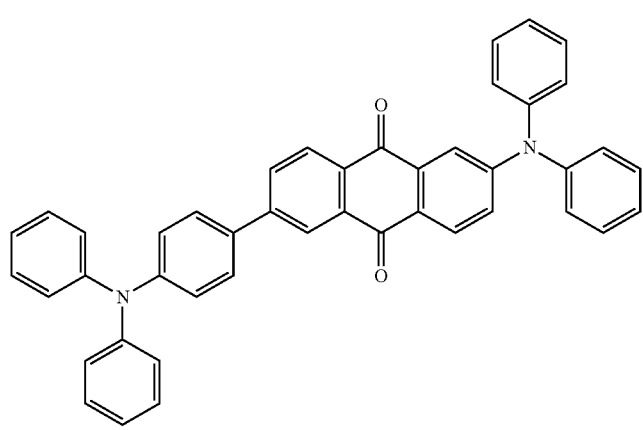

-continued
TADF58
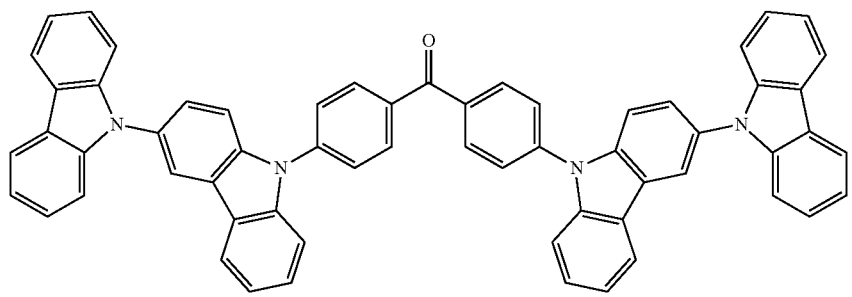
TADF59
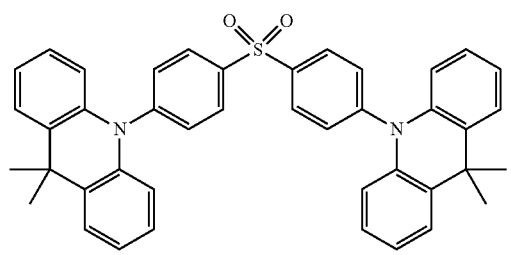
TADF60
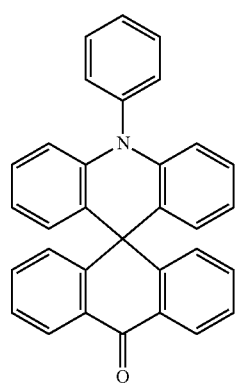
TADF61
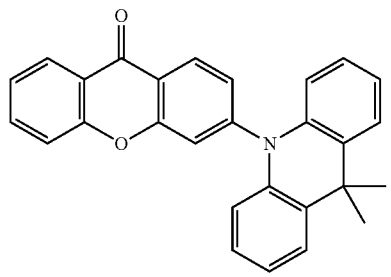
TADF62
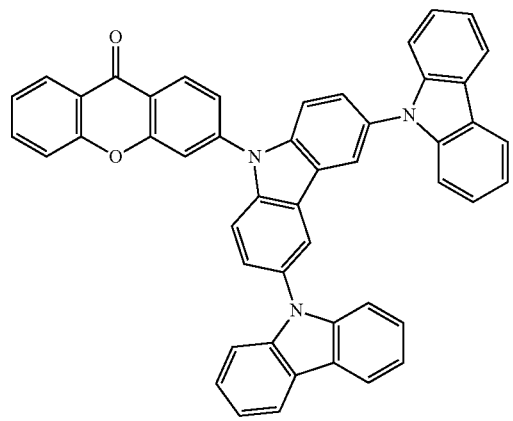
TADF63
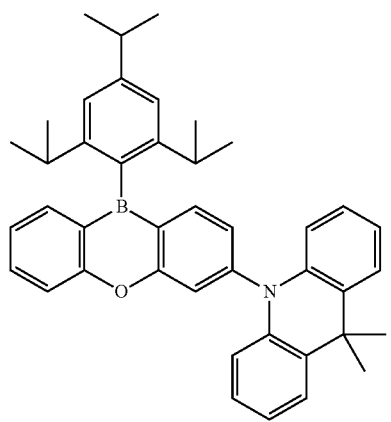
TADF64
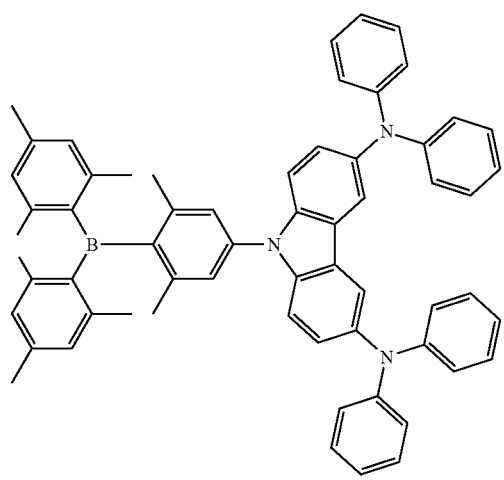

TADF65

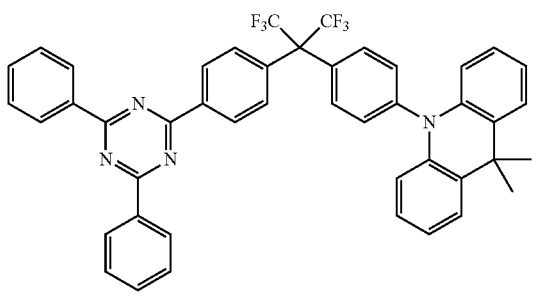

TADFG66

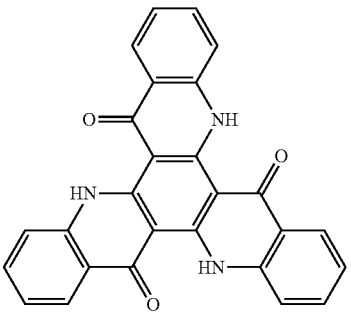

TADF67

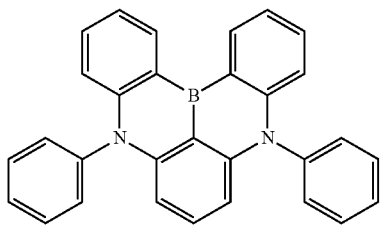

TADF68

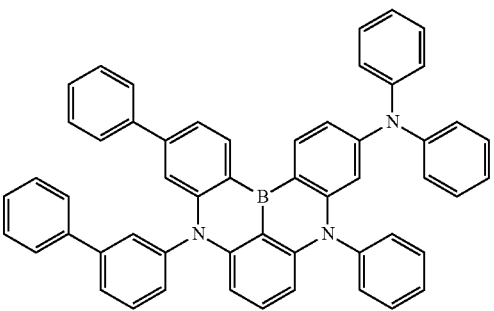

TADF69

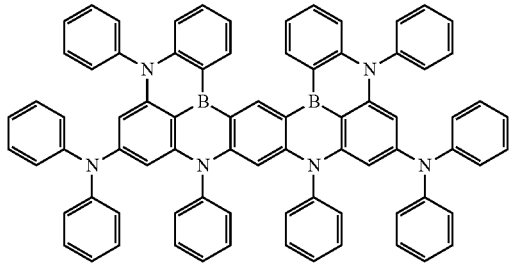

TADF70

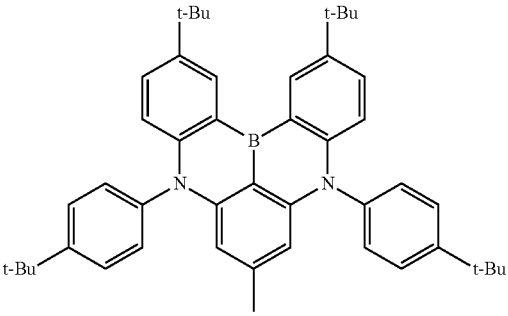

In the invention, any other known delayed fluorescent material than the above can be appropriately combined with the compound represented by the general formula (1) and can be used here thus combined. In addition, unknown delayed fluorescent materials can also be used.

As delayed fluorescent materials, there can be mentioned compounds included in the general formulae described in WO2013/154064, paragraphs 0008 to 0048 and 0095 to 0133; WO2013/011954, paragraphs 0007 to 0047 and 0073 to 0085; WO2013/011955, paragraphs 0007 to 0033 and 0059 to 0066; WO2013/081088, paragraphs 0008 to 0071 and 0118 to 0133; JP 2013-256490 A, paragraphs 0009 to 0046 and 0093 to 0134; JP 2013-116975 A, paragraphs 0008 to 0020 and 0038 to 0040: WO2013/133359, paragraphs 0007 to 0032 and 0079 to 0084: WO2013/161437, paragraphs 0008 to 0054 and 0101-0121: JP 2014-9352 A, paragraphs 0007 to 0041 and 0060 to 0069; JP 2014-9224 A, paragraphs 0008 to 0048 and 0067 to 0076: JP 2017-119663 A, paragraphs 0013 to 0025; JP 2017-119664 A, paragraphs 0013 to 0026; JP 2017-222623 A, paragraphs 0012 to 0025; JP 2017-226838 A, paragraphs 0010 to 0050: JP 2018-100411 A, paragraphs 0012 to 0043; WO2018/047853, paragraphs 0016 to 0044; and especially, exemplary compounds therein capable of emitting delayed fluorescence. In addition, also employable here are light-emitting materials capable of emitting delayed fluorescence, as described in JP 2013-253121 A, WO2013/133359, WO2014/034535, WO2014/115743, WO2014/122895, WO2014/126200, WO2014/136758, WO2014/133121. WO2014/136860, WO2014/196585, WO2014/189122, WO2014/168101, WO2015/008580, WO2014/203840, WO2015/002213, WO2015/016200, WO2015/019725, WO2015/072470, WO2015/108049, WO2015/080182, WO2015/072537, WO2015/080183, JP 2015-129240 A, WO2015/129714, WO2015/129715, WO2015/133501, WO2015/136880, WO2015/137244, WO2015/137202, WO2015/137136, WO2015/146541 and WO2015/159541. These patent publications described in this paragraph are hereby incorporated as a part of this description by reference.

Preferably, the delayed fluorescent material for use in the invention does not contain a metal atom. For example, as the delayed fluorescent material, a compound composed of atoms alone selected from the group consisting of a carbon atom, a hydrogen atom, a nitrogen atom, an oxygen atom, and a sulfur atom can be selected. For example, as the delayed fluorescent material, a compound composed of atoms alone selected from the group consisting of a carbon atom, a hydrogen atom, a nitrogen atom, and an oxygen atom can be selected. For example, as the delayed fluorescent material, a compound composed of atoms alone selected from the group consisting of a carbon atom, a hydrogen atom, and a nitrogen atom can be selected.

Unless otherwise specifically indicated, details of the alkyl group, the alkenyl group, the aryl group and the heteroaryl groups are as mentioned below.

The "alkyl group" may be any of a linear, branched or cyclic one. The group may have two or more kinds of a linear moiety, a cyclic moiety and a branched moiety as combined. The carbon number of the alkyl group may be, for example, 1 or more, 2 or more, or 4 or more. The carbon number may be 30 or less, 20 or less, 10 or less, 6 or less, or 4 or less. Specific examples of the alkyl group include a methyl group, an ethyl group, an n-propyl group, an isopropyl group, an n-butyl group, an isobutyl group, a tert-butyl group, an n-pentyl group, an isopentyl group, an n-hexyl group, an isohexyl group, a 2-ethylhexyl group, an n-heptyl group, an isoheptyl group, an n-octyl group, an isooctyl group, an n-nonyl group, an isononyl group, an n-decanyl group, an isodecanyl group, a cyclopentyl group, a cyclohexyl group, and a cycloheptyl group. The alkyl group to be a substituent may be further substituted with an aryl group. Regarding the alkyl moiety in the "alkoxy group", the "alkylthio group", the "acyl group" and the "alkoxycarbonyl group", reference can be made to the description of the "alkyl group" given herein.

The "alkenyl group" as referred to herein may be any of a linear, branched or cyclic one. The group may have two or more kinds of a linear moiety, a cyclic moiety and a branched moiety as combined. The carbon number of the alkenyl group may be, for example, 2 or more, or 4 or more. The carbon number may be 30 or less, 20 or less, 10 or less, 6 or less, or 4 or less. Specific examples of the alkenyl group include an ethenyl group, an n-propenyl group, an isopropenyl group, an n-butenyl group, an isobutenyl group, an n-pentenyl group, an isopentenyl group, an n-hexenyl group, an isohexenyl group, and a 2-ethylhexenyl group. The alkenyl group to be a substituent may be further substituted with an aryl group.

The "aryl group" and the "heteroaryl group" each may be a single ring or may be a condensed ring of two or more kinds of rings. In the case of a condensed ring, the number of the rings that are condensed is preferably 2 to 6, and, for example, can be selected from 2 to 4. Specific examples of the ring include a benzene ring, a pyridine ring, a pyrimidine ring, a triazine ring, a naphthalene ring, an anthracene ring, a phenanthrene ring, a triphenylene ring, a quinoline ring, a pyrazine ring, a quinoxaline ring, and a naphthyridine ring. Specific examples of the aryl group or the heteroaryl group include a phenyl group, a 1-naphthyl group, a 2-naphthyl group, a 1-anthracenyl group, a 2-anthracenyl group, a 9-anthracenyl group, a 2-pyridyl group, a 3-pyridyl group, and a 4-pyridyl group. Regarding the "arylene group" and the "heteroarylene group", reference can be made to the description of the aryl group and the heteroaryl group, in which the valency of the group is changed from 1 to 2. Regarding the aryl moiety of the "aryloxy group", the "arylthio group" and the "aryloxycarbonyl group", reference can be made to the description of the "aryl group". Regarding the heteroaryl moiety of the "heteroaryloxy group", the "heteroarylthio group" and the "heteroaryloxycarbonyl group", reference can be made to the description of the "heteroaryl group".

(Composition)

The composition of the invention contains a compound represented by the general formula (1) and a delayed fluorescent material. In one embodiment of the invention, the composition is composed of one or more compounds represented by the general formula (1) and one or more delayed fluorescent materials alone. In one embodiment of the invention, the composition is composed of one compound represented by the general formula (1) and one delayed fluorescent material alone. In one embodiment of the invention, the composition contains a third component in addition to a compound represented by the general formula (1) and a delayed fluorescent material. The third component as referred to herein is neither a compound represented by the general formula (1) nor a delayed fluorescent material. The composition may contain one third component, or may contain two or more kinds of third components. The content of the third component in the composition can be selected within a range of 30% by weight or less, or can be selected within a range of 10% by weight or less, or can be selected within a range of 1% by weight or less, or can be selected within a range of 0.1% by weight or less. In one embodiment of the invention, the third component does not emit light. In one embodiment of the invention, the third component emits fluorescence. In one preferred embodiment of the invention, the maximum component of emission from the composition of the invention is fluorescence (including delayed fluorescence).

In the composition of the invention, the content by weight of the compound represented by the general formula (1) is larger than that of the delayed fluorescent material. The content of the compound represented by the general formula (1) can be selected within a range of at least three times by weight the content of the delayed fluorescent material, or can be selected within a range of at least 10 times by weight, or can be selected within a range of at least 100 times by weight, or can be selected within a range of at least 1000 times by weight, or can be selected, for example, within a range of at most 10000 times by weight.

In the composition of the invention, preferably, a delayed fluorescent material having a smaller excited singlet energy than the excited singlet energy of the compound represented by the general formula (1) is selected. The excited singlet energy difference can be 0.1 eV or more, 0.3 eV or more, 0.5 eV or more, or can be 2 eV or less, or 1.5 eV or less, or 1.0 eV or less.

Preferably, the composition of the invention does not contain a metal element. In one embodiment of the invention, the composition of the invention is composed of atoms alone selected from the group consisting of a carbon atom, a hydrogen atom, a nitrogen atom, an oxygen atom, a sulfur atom, a boron atom and a halogen atom. In one embodiment of the invention, the composition of the invention is composed of atoms alone selected from the group consisting of a carbon atom, a hydrogen atom, a nitrogen atom, an oxygen atom, and a sulfur atom.

In one embodiment of the invention, the compound represented by the general formula (1) is useful as a host material to be used along with a delayed fluorescent material and a fluorescent compound. Consequently, in one embodiment of the invention, the composition of the invention contains fluorescent compound in addition to the compound represented by the general formula (1) and a delayed fluorescent material.

Preferably, the fluorescent compound has a smaller lowest excited single energy (ES1) than the compound represented by the general formula (1) and the delayed fluorescent material. The fluorescent compound receives energy from the compound of the general formula (1) and the delayed fluorescent material in an excited singlet state and from the delayed fluorescent material having been in an excited singlet state from an excited triplet state through reverse intersystem crossing to transition into a singlet excited state, and emits fluorescence when thereafter returning back to a ground state. Not specifically limited, the fluorescent compound may be any one capable of receiving energy from the compound represented by the general formula (1) and the delayed fluorescent material to emit fluorescence, and the emission from the compound may be fluorescence or delayed fluorescence. Above all, the light-emitting material for use as the fluorescent compound is preferably one capable of emitting fluorescence when returning back from a lowest excited singlet energy level to a ground energy level. Two or more kinds of fluorescent compounds can be used here as combined. For example, by combining two or more kinds of fluorescent compounds that differ in the emission color, it is possible to emit light of a desired color.

As the fluorescent compound, usable herein are an anthracene derivative, a tetracene derivative, a naphthacene derivative, a pyrene derivative, a perylene derivative, a chrysene derivative, a rubrene derivative, a coumarin derivative, a pyran derivative, a stilbene derivative, a fluorene derivative, an anthryl derivative, a pyrromethene derivative, a terphenyl derivative, a terphenylene derivative, a fluoranthene derivative, an amine derivative, a quinacridone derivative, an oxadiazole derivative, a malononitrile derivative, a pyran derivative, a carbazole derivative, a julolidine derivative, a thiazole derivative, and a derivative having a metal (Al, Zn), and a compound having a multiple resonance effect such as a boron-containing polycyclic aromatic skeleton-having compound such as diazaboranaphthoanthracene. The skeletons exemplified herein may have a substituent, or may not have a substituent. These exemplified skeletons can be combined together.

For specific examples of the fluorescent compound, reference can be made to the compounds exemplified hereinabove as the specific examples of the delayed fluorescent material. At that time, the composition of the invention contains two or more kinds of delayed fluorescent materials, in which one having a higher lowest excited singlet energy functions as an assist dopant and the other having a lower lowest excited single energy functions as a fluorescent compound that mainly acts for light emission. Preferably, the compound used as the fluorescent compound has a PL emission quantum yield of 60% or more, more preferably 80% or more. Also preferably, the compound used as the fluorescent compound shows an instantaneous fluorescence lifetime of 50 ns or less, more preferably 20 ns or less. The instantaneous fluorescence lifetime means an emission lifetime of a component that decays first among plural exponential decay components observed in measuring the emission lifetime of thermally activated delayed fluorescence compounds. Also preferably, of the compound used as the fluorescent compound, the fluorescence emission speed to the ground state from the lowest excited singlet state (S1) is higher than the intersystem crossing speed from S1 to the lowest excited triplet state (T1). Regarding the computation method for the speed constant of compounds, reference can be made to known literature relating to thermally activated delayed fluorescent materials (e.g., H. Uoyama, et al., Nature 492, 234 (2012), K. Masui, et al., Org. Electron. 14, 2721, (2013)).

Preferred compounds usable as fluorescent compounds along with delayed fluorescent materials are shown below, but the fluorescent compounds usable in the invention should not be limitatively interpreted by these specific examples.

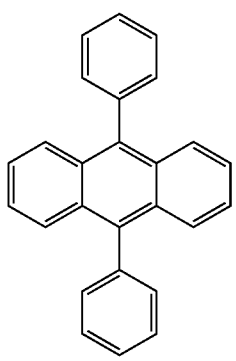

D1

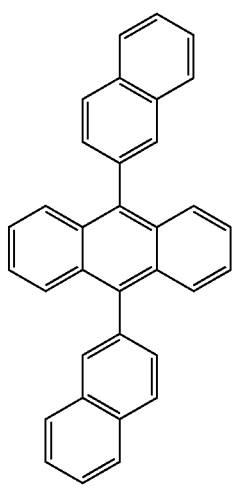

D2

-continued

D3

D4

D5

D6

-continued
| | |
|---|---|
| D7 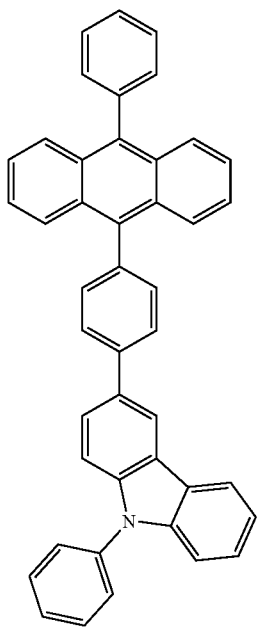 | D8 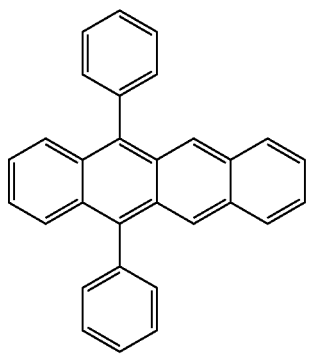 |
| D9 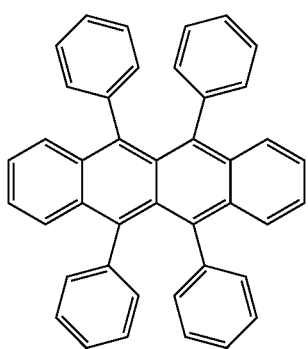 | D10 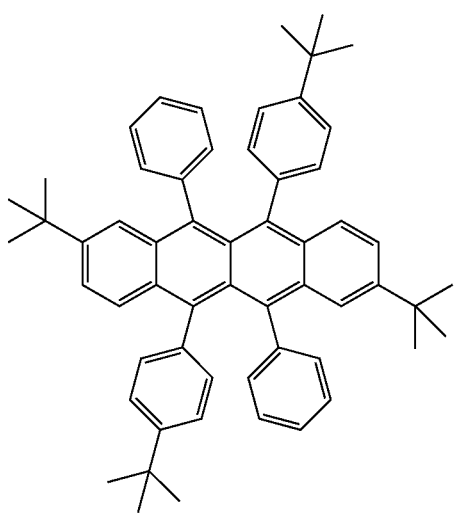 |
| D11 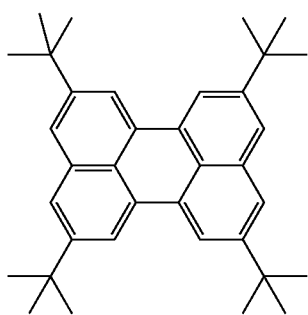 | D12 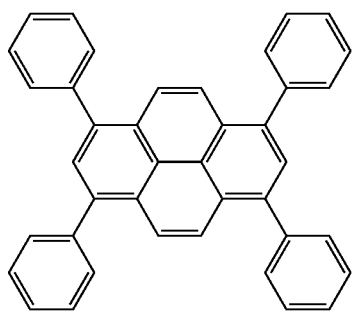 |

-continued
| | |
|---|---|
| D13 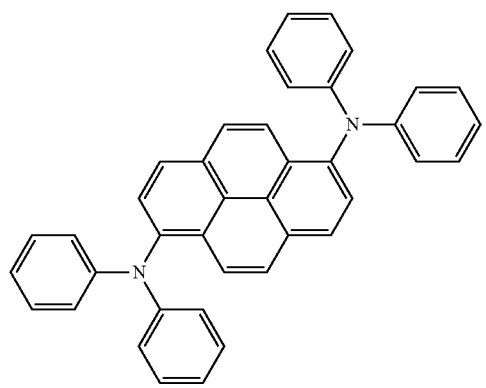 | D14 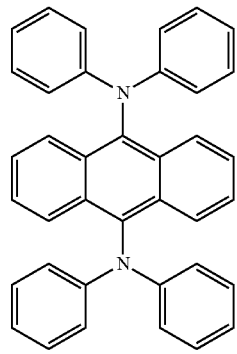 |
| D15 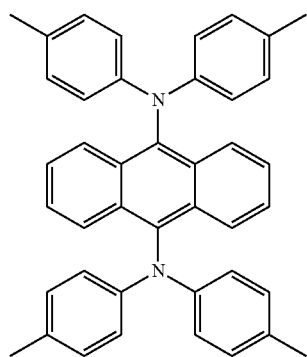 | D16 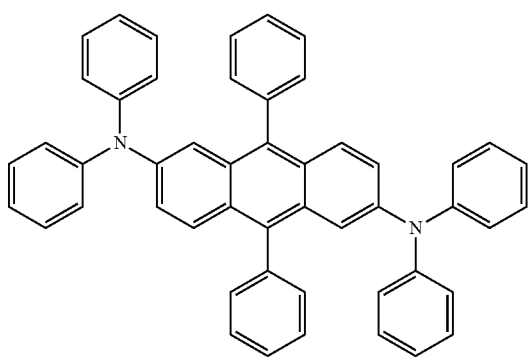 |
| D17 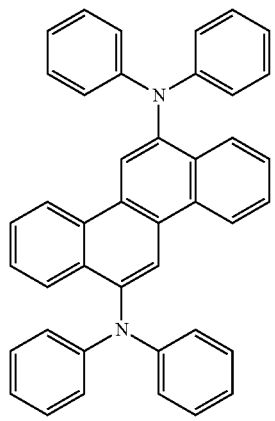 | D18 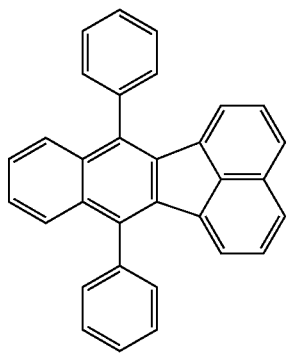 |
| D19 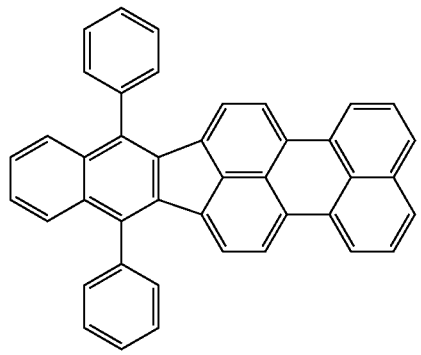 | D20 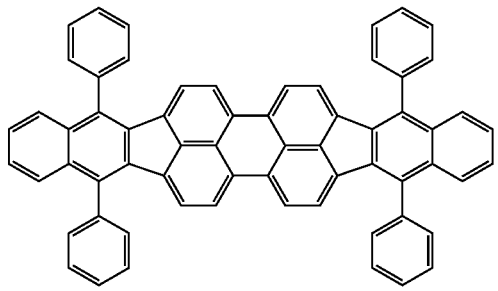 |

-continued
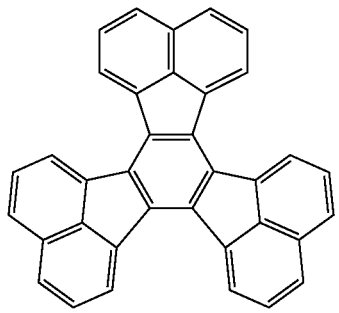 D21
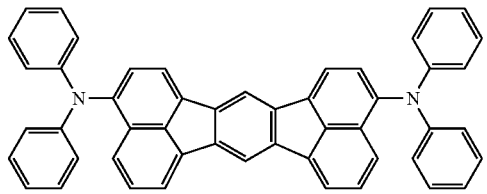 D22
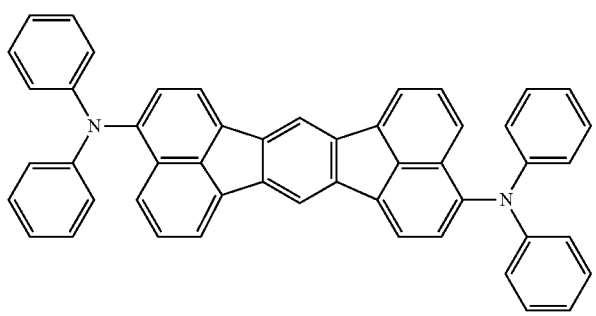 D23
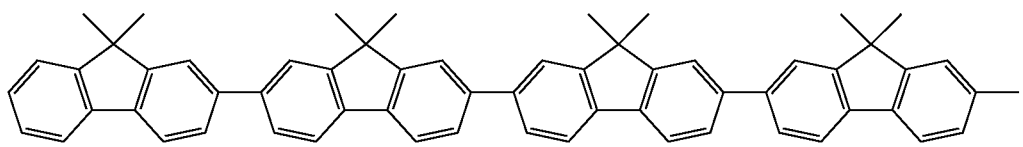 D24
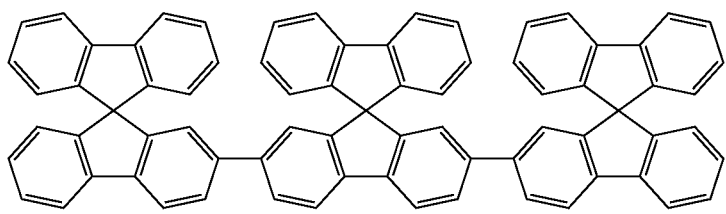 D25
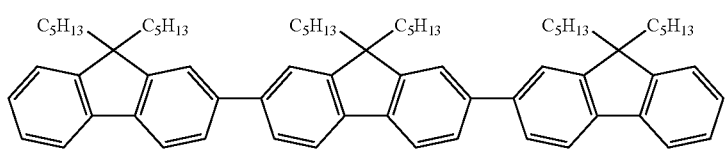 D26

-continued
D27
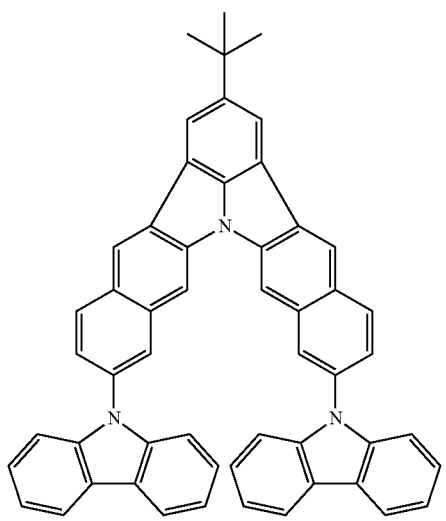
D28
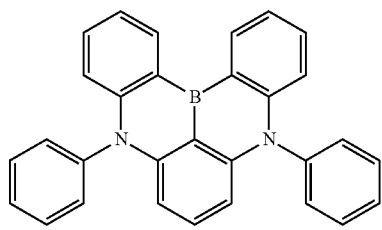
D29
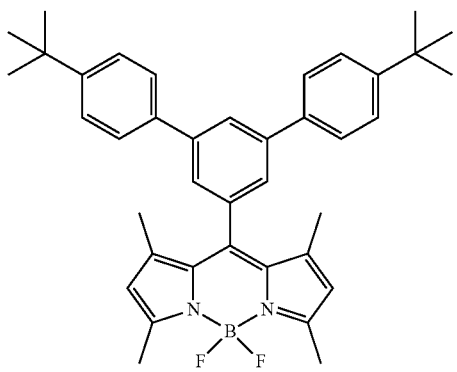
D30
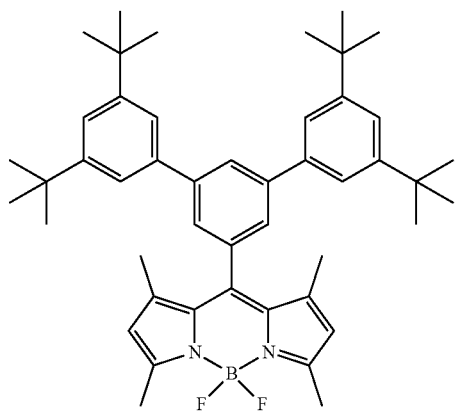
D31
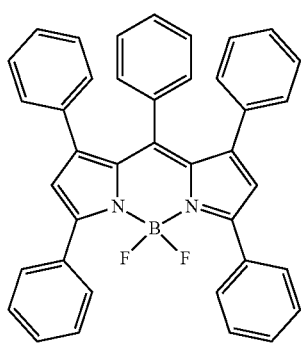
D32
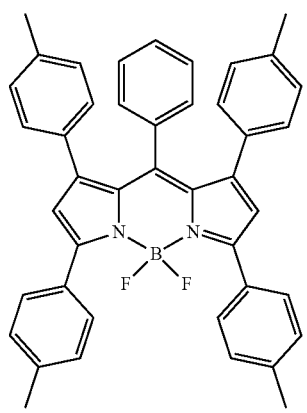
D33
D34

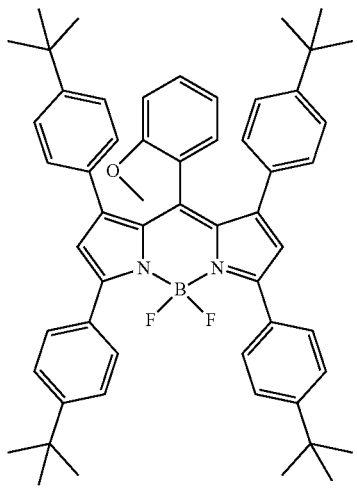

The compounds described in WO2015/022974, paragraphs 0220 to 0239 are also preferably employed as a fluorescent compound in the invention.

In one embodiment of the invention, the compound represented by the general formula (1) can be used along with any other host material in a light-emitting layer (composition) containing plural host materials. Namely, in one embodiment of the invention, the composition of the invention contains plural host materials including the compound represented by the general formula (1). In the composition of the invention plural kinds of compounds represented by the general formula (1) can be used, or a combination of a compound represented by the general formula (1) and a host material not represented by the general formula (1) can be used.

Hereinunder, preferred compounds usable as the second host material along with the compound represented by the general formula (1) are shown, but the second host material usable in the invention should not be limitatively interpreted by these specific examples.

-continued

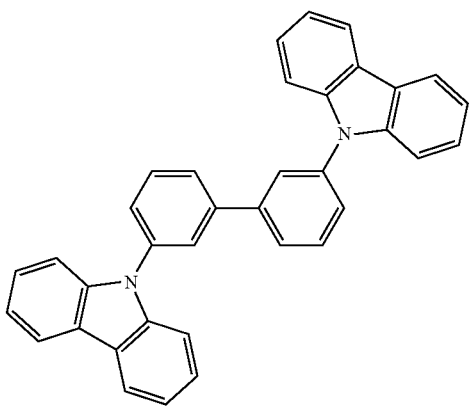

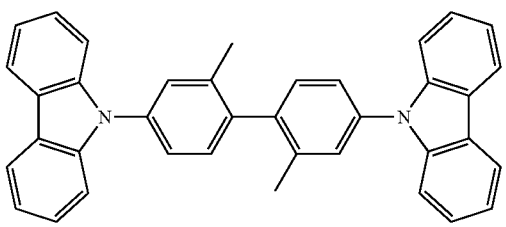

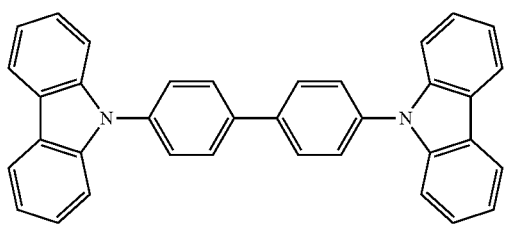

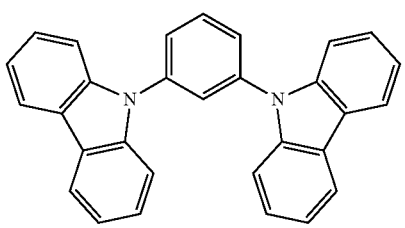

-continued
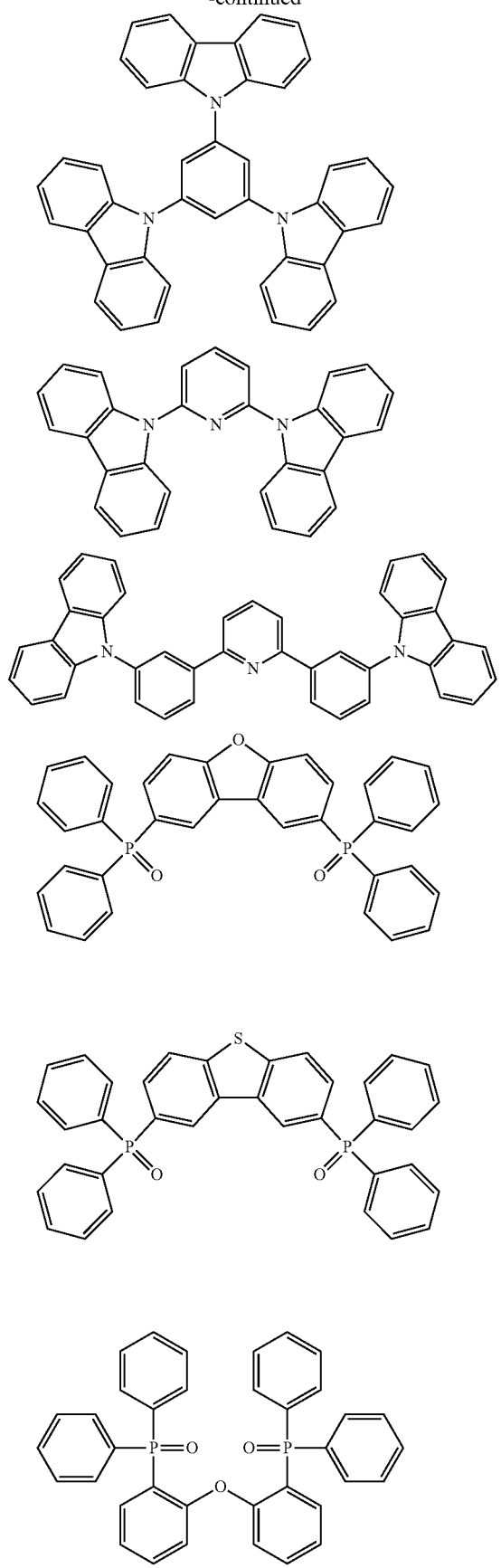
-continued
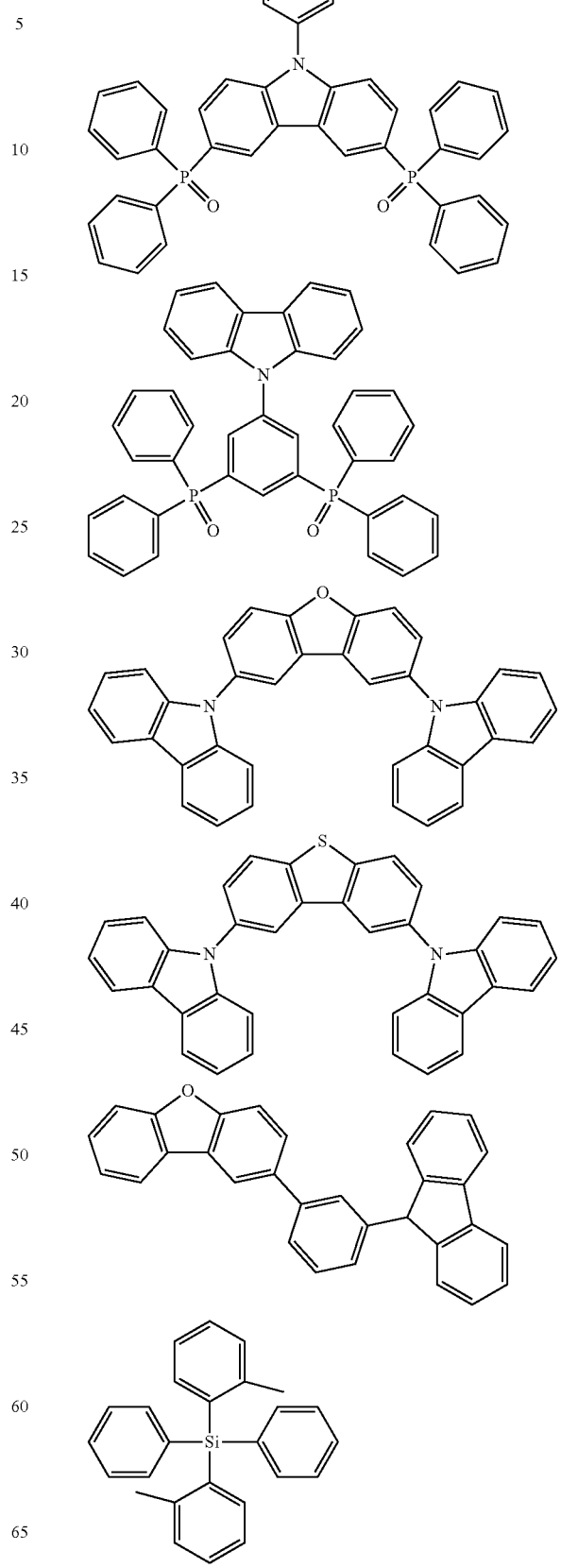

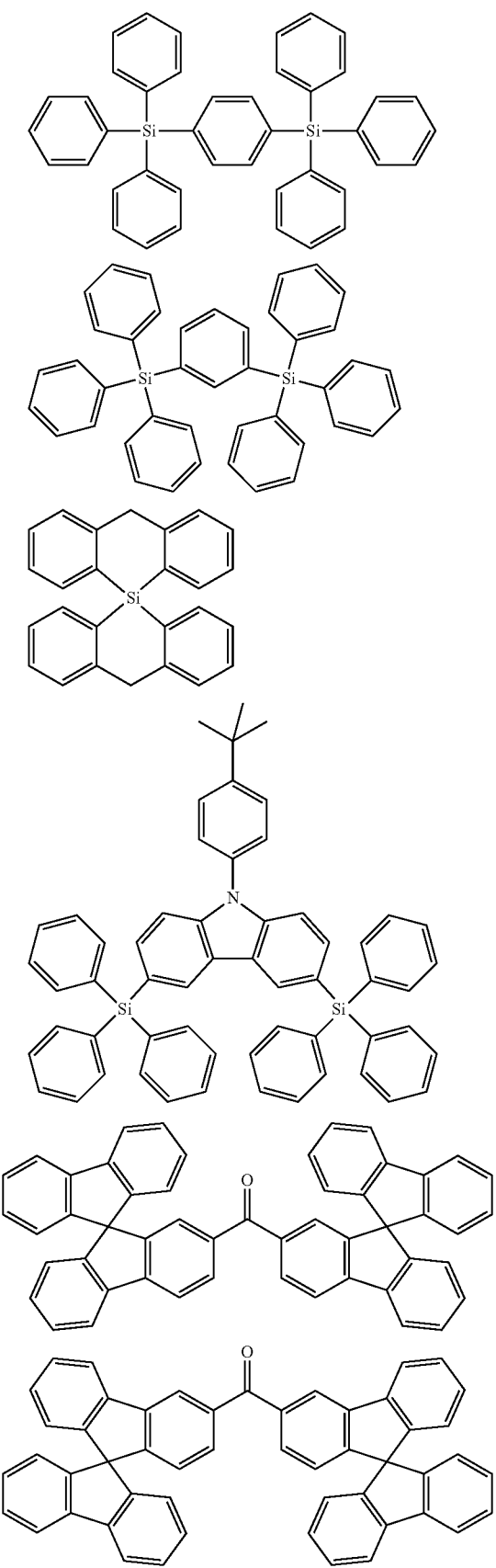
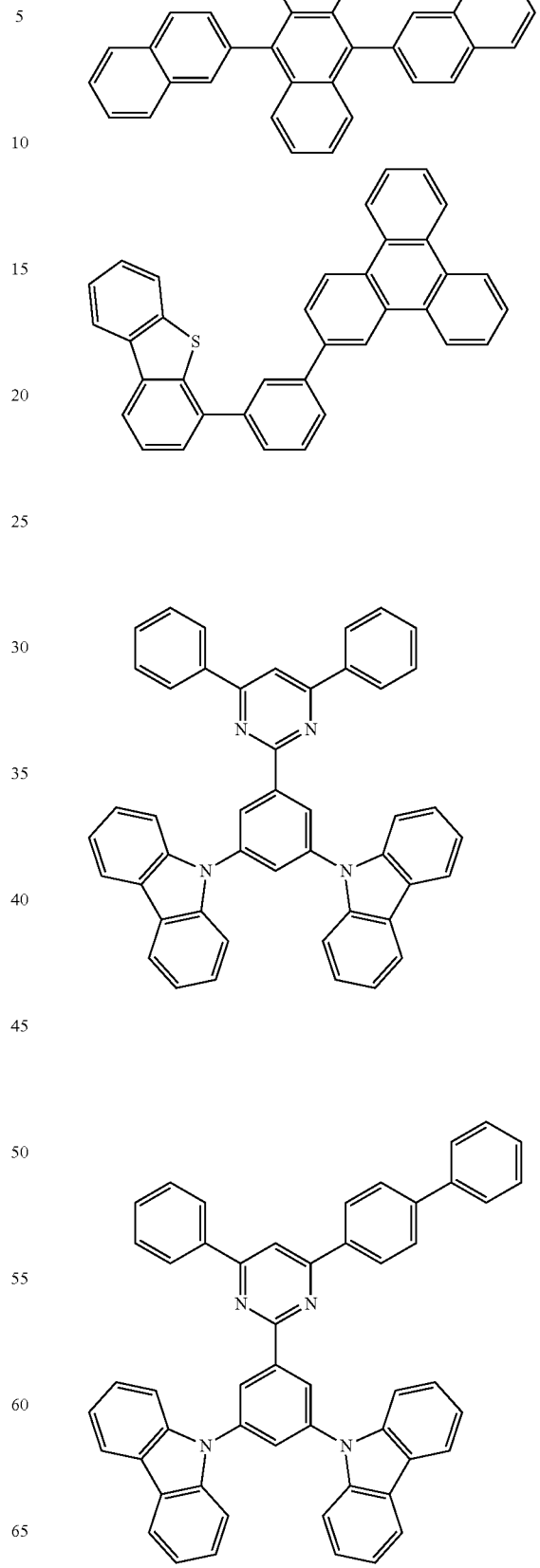

-continued

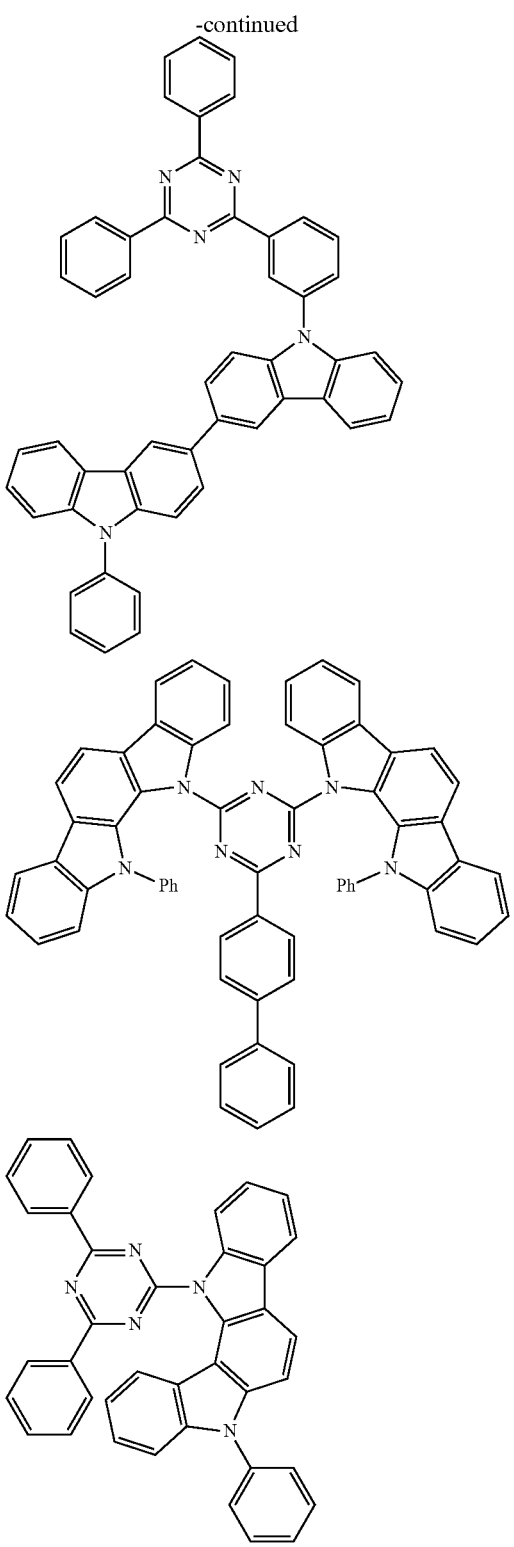

The form of the composition of the invention is not specifically limited. In one especially preferred embodiment of the invention, the composition of the invention is a film. The film of the composition of the invention can be formed in a wet process or in a dry process.

In a wet process, a solution prepared by dissolving the composition of the invention is applied onto a surface, and the solvent used is removed to form a light-emitting layer.

The wet process includes a spin coating method, a slit coating method, an inkjet method (spray method), a gravure printing method, an offset printing method, and a flexographic printing method, but is not limited to these. In the wet process, a suitable organic solvent capable of dissolving the composition of the invention is selected and used. In some embodiments, a substituent (for example, an alkyl group) capable of increasing the solubility in an organic solvent can be introduced into the compound contained in the composition of the invention.

As a dry process, a vacuum evaporation method is preferably employed. In the case where a vacuum evaporation method is employed, the compounds constituting the composition of the invention can be co-evaporated from individual evaporation sources, or can be co-evaporated from a single evaporation source prepared by mixing all the compounds. In the case where a single evaporation source is used, a mixed powder prepared by mixing powders of all the compounds can be used, or a compressed-molded article prepared by compression-molding the mixed powder can be used, or a mixture prepared by heating, meting and mixing the compounds and then cooling the resultant mixture can be used. In some embodiments, plural compounds contained in a single evaporation source is co-evaporated under the condition that the evaporation speed (weight reducing speed) is the same or is nearly the same between the plural compounds to thereby form a film having a compositional ratio corresponding to the compositional ratio of the plural compounds contained in the evaporation source. When plural compounds are mixed to prepare an evaporation source in the same compositional ratio as the compositional ratio of the film to be formed, a film having a desired compositional ratio can be formed in a simple manner. In some embodiments, a temperature at which the compounds to be co-evaporated could have the same weight reduction rate is specifically defined, and the temperature can be employed as the temperature for co-evaporation. In the case where a film is formed in an evaporation method, the molecular weight of each compound to constitute the composition is preferably 1500 or less, more preferably 1200 or less, even more preferably 1000 or less, further more preferably 900 or less. The lower limit of the molecular weight can be, for example, 450, or can be 500, or can be 600.

(Organic Light-Emitting Device)

By forming a light-emitting layer of the composition of the invention, there can be provided an excellent organic light-emitting device such as an organic photoluminescent device (organic PL device) and an organic electroluminescent device (organic EL device). The organic light-emitting device of the invention is a fluorescence emitting device, and the maximum component for emission from the device is fluorescence (here, fluorescence includes delayed fluorescence).

The thickness of the light-emitting layer can be, for example, 1 to 15 nm, or can be 2 to 10 nm, or can be 3 to 7 nm.

An organic photoluminescent device has a configuration that has at least a light-emitting layer formed on a substrate. An organic electroluminescent device has a configuration that has at least an anode, a cathode, and an organic layer formed between the anode and the cathode. The organic layer contains at least alight-emitting layer, and can be a light-emitting layer alone, or can have any other one or more organic layers than alight-emitting layer. Such other organic layers include a hole transporting layer, a hole injection layer, an electron barrier layer, a hole barrier layer, an electron injection layer, an electron transporting layer, and an exciton barrier layer. The hole transporting layer may also be a hole injection transporting layer having a hole injection function, and the electron transporting layer may also be an electron injection transporting layer having an electron injection function. A specific configuration example of an organic electroluminescent device is shown in FIGURE. In FIGURE, 1 is a substrate, 2 is an anode, 3 is a hole injection layer, 4 is a hole transporting layer, 5 is a light-emitting layer, 6 is an electron transporting layer, and 7 is a cathode.

In the case where the organic light-emitting device of the invention is a multi-wavelength emission-type organic light-emitting device, the device can be so designed that shortest wavelength emission contains delayed fluorescence. The device can be so designed that shortest wavelength emission does not contain delayed fluorescence.

The organic light-emitting device using the composition of the invention is, when excited by a thermal or electronic means, able to emit light in a UV region, or light of blue, green, yellow, orange or red in a visible region (e.g., 420 to 500 nm, 500 to 600 nm or 600 to 700 nm) or light in a near IR region. For example, the organic light-emitting device can emit light in a red or orange region (e.g., 620 to 780 nm). For example, the organic light-emitting device can emit light in an orange or yellow region (e.g., 570 to 620 nm). For example, the organic light-emitting device can emit light in a green region (e.g., 490 to 575 nm). For example, the organic light-emitting device can emit light in a blue region (e.g., 400 to 490 nm). For example, the organic light-emitting device can emit light in a UV spectral region (e.g., 280 to 400 nm). For example, the organic light-emitting device can emit light in an IR spectral region (e.g., 780 to 2 µm).

The maximum component of light emission from the organic light-emitting device using the composition of the invention is preferably light emission from the delayed fluorescent material contained in the composition of the invention. Emission from the compound represented by the general formula (1) is preferably less than 10% of light emission from the organic light-emitting device, and can be less than 1%, less than 0.1% or less than 0.01%, or even a detection limit or less. Emission from the delayed fluorescent material can be, for example, more than 50%, more than 90%, or more than 99 of light emission from the organic light-emitting device. In the case where the layer (light-emitting layer) containing the composition of the invention contains a fluorescent material as a third component, the maximum component of light emission from the organic light-emitting device can be emission from the fluorescent material. In that case, light emission from the fluorescent material can be, for example, more than 50%, more than 90% or more than 99% of light emission from the organic light-emitting device.

In the following, the constituent members and the other layers than the light-emitting layer of the organic electroluminescent device are described.

Substrate:

In some embodiments, the organic electroluminescent device of the invention is supported by a substrate, wherein the substrate is not particularly limited and may be any of those that have been commonly used in an organic electroluminescent device, for example those formed of glass, transparent plastics, quartz and silicon.

Anode

In some embodiments, the anode of the organic electroluminescent device is made of a metal, an alloy, an electroconductive compound, or a combination thereof. In some embodiments, the metal, alloy, or electroconductive compound has a large work function (4 eV or more). In some embodiments, the metal is Au. In some embodiments, the electroconductive transparent material is selected from CuI, indium tin oxide (ITO), $SnO_2$, and ZnO. In some embodiments, an amorphous material capable of forming a transparent electroconductive film, such as IDIXO ($In_2O_3$—ZnO), is be used. In some embodiments, the anode is a thin film. In some embodiments the thin film is made by vapor deposition or sputtering. In some embodiments, the film is patterned by a photolithography method. In some embodiments, where the pattern may not require high accuracy (for example, approximately 100 µm or more), the pattern may be formed with a mask having a desired shape on vapor deposition or sputtering of the electrode material. In some embodiments, when a material can be applied as a coating, such as an organic electroconductive compound, a wet film forming method, such as a printing method and a coating method is used. In some embodiments, when the emitted light goes through the anode, the anode has a transmittance of more than 10%, and the anode has a sheet resistance of several hundred Ohm per square or less. In some embodiments, the thickness of the anode is from 10 to 1,000 nm. In some embodiments, the thickness of the anode is from 10 to 200 nm. In some embodiments, the thickness of the anode varies depending on the material used.

Cathode

In some embodiments, the cathode is made of an electrode material a metal having a small work function (4 eV or less) (referred to as an electron injection metal), an alloy, an electroconductive compound, or a combination thereof. In some embodiments, the electrode material is selected from sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. In some embodiments, a mixture of an electron injection metal and a second metal that is a stable metal having a larger work function than the electron injection metal is used. In some embodiments, the mixture is selected from a magnesium-silver mixture, a magnesium-aluminum mixture, a magnesium-indium mixture, an aluminum-aluminum oxide ($Al_2O_3$) mixture, a lithium-aluminum mixture, and aluminum. In some embodiments, the mixture increases the electron injection property and the durability against oxidation. In some embodiments, the cathode is produced by forming the electrode material into a thin film by vapor deposition or sputtering. In some embodiments, the cathode has a sheet resistance of several hundred Ohm per square or less. In some embodiments, the thickness of the cathode ranges from 10 nm to 5 µm. In some embodiments, the thickness of the cathode ranges from 50 to 200 nm. In some embodiments, for transmitting the emitted light, any one of the anode and the cathode of the organic electroluminescent device is transparent or translucent. In some embodiments, the transparent or translucent electroluminescent devices enhances the light emission luminance.

In some embodiments, the cathode is formed with an electroconductive transparent material, as described for the anode, to form a transparent or translucent cathode. In some embodiments, a device comprises an anode and a cathode, both being transparent or translucent.

Injection Layer

An injection layer is a layer between the electrode and the organic layer. In some embodiments, the injection layer decreases the driving voltage and enhances the light emission luminance. In some embodiments the injection layer includes a hole injection layer and an electron injection layer. The injection layer can be positioned between the anode and the light-emitting layer or the hole transporting layer, and between the cathode and the light-emitting layer or the electron transporting layer. In some embodiments, an injection layer is present. In some embodiments, no injection layer is present.

Preferred compound examples for use as a hole injection material are shown below.

MoO₃,

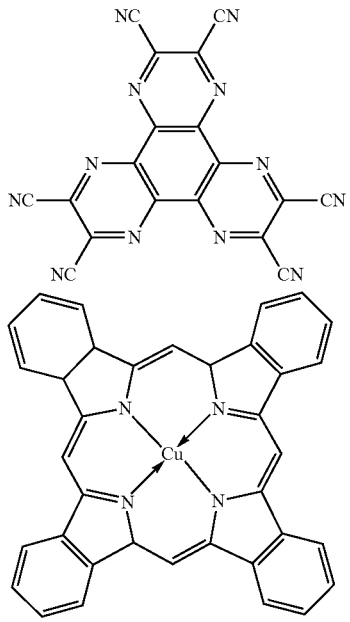

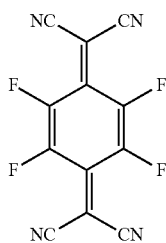

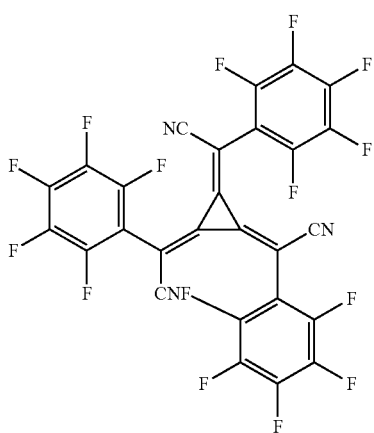

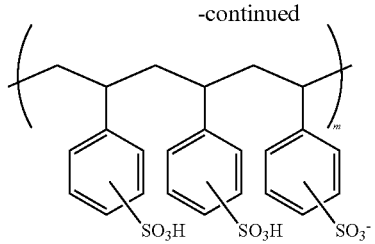

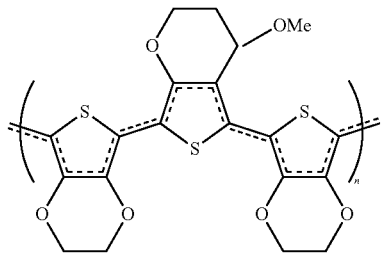

Next, preferred compound examples for use as an electron injection material are shown below.

LiF, CsF,

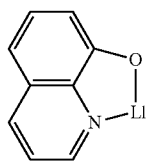

Barrier Layer

A barrier layer is a layer capable of inhibiting charges (electrons or holes) and/or excitons present in the light-emitting layer from being diffused outside the light-emitting layer. In some embodiments, the electron barrier layer is between the light-emitting layer and the hole transporting layer, and inhibits electrons from passing through the light-emitting layer toward the hole transporting layer. In some embodiments, the hole barrier layer is between the light-emitting layer and the electron transporting layer, and inhibits holes from passing through the light-emitting layer toward the electron transporting layer. In some embodiments, the barrier layer inhibits excitons from being diffused outside the light-emitting layer. In some embodiments, the electron barrier layer and the hole barrier layer are exciton barrier layers. As used herein, the term "electron barrier layer" or "exciton barrier layer" includes a layer that has the functions of both electron barrier layer and of an exciton barrier layer.

Hole Barrier Layer

A hole barrier layer acts as an electron transporting layer. In some embodiments, the hole barrier layer inhibits holes from reaching the electron transporting layer while transporting electrons. In some embodiments, the hole barrier layer enhances the recombination probability of electrons and holes in the light-emitting layer. The material for the hole barrier layer may be the same materials as the ones described for the electron transporting layer.

Preferred compound examples for use for the hole barrier layer are shown below.

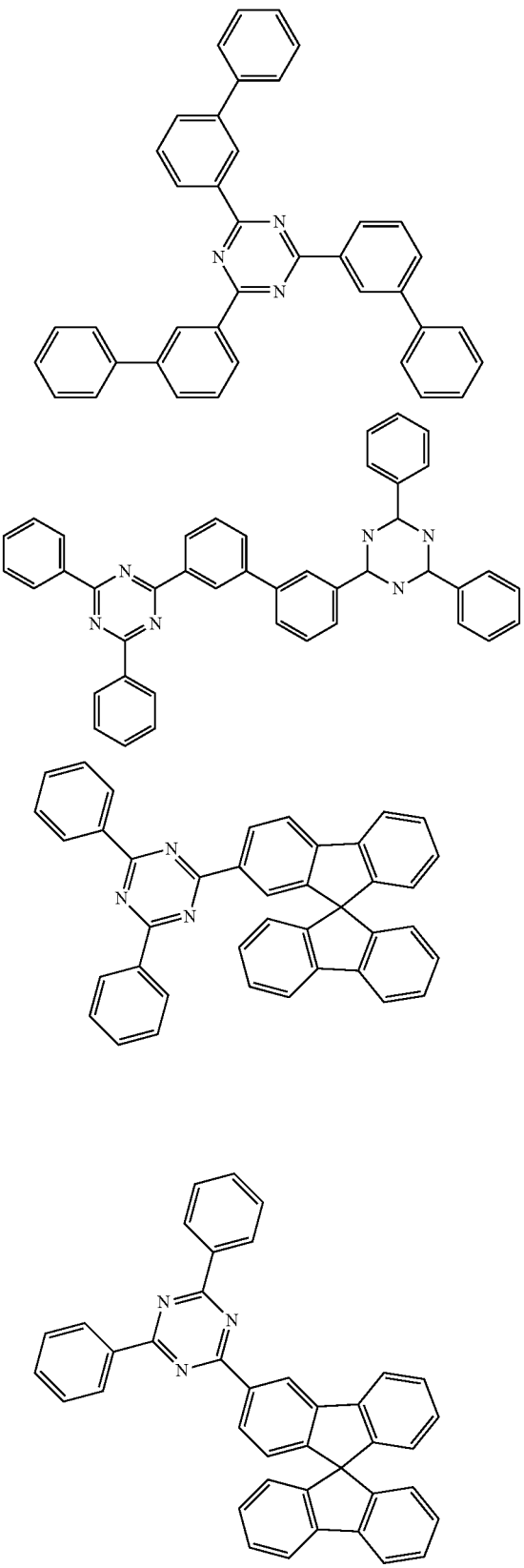

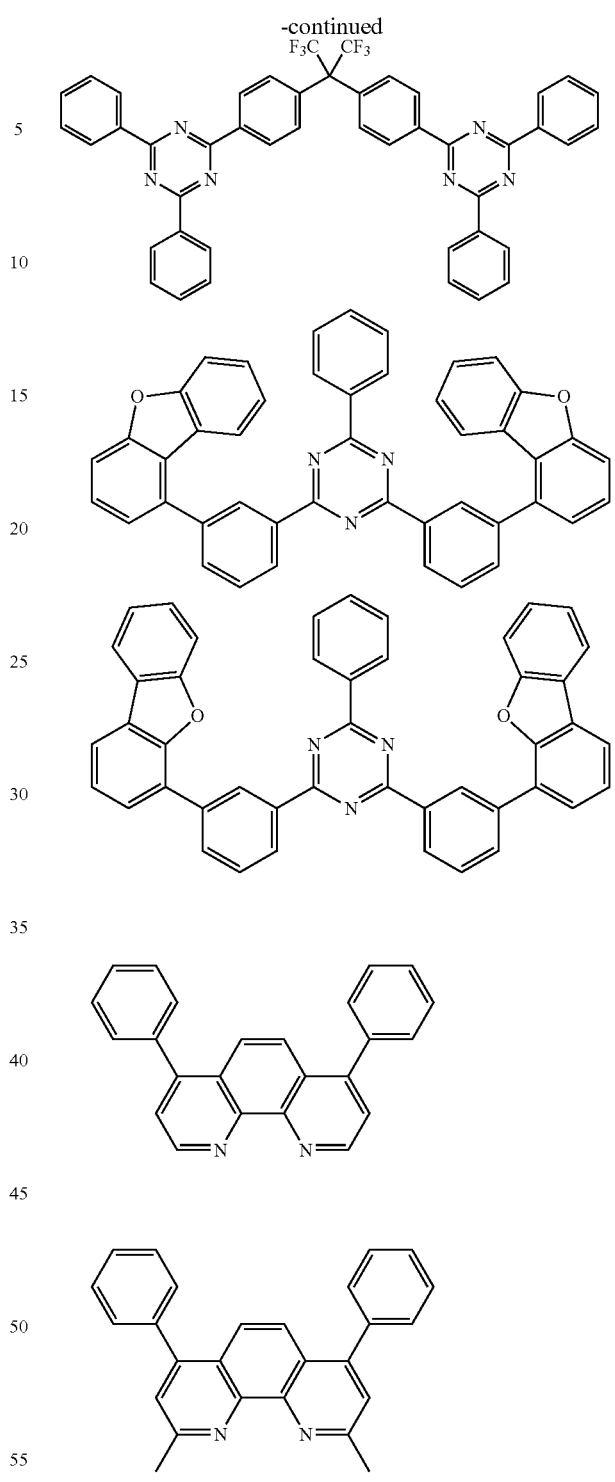

Electron Barrier Layer

As electron barrier layer transports holes. In some embodiments, the electron barrier layer inhibits electrons from reaching the hole transporting layer while transporting holes. In some embodiments, the electron barrier layer enhances the recombination probability of electrons and holes in the light-emitting layer.

Preferred compound examples for use as the electron barrier material are shown below.

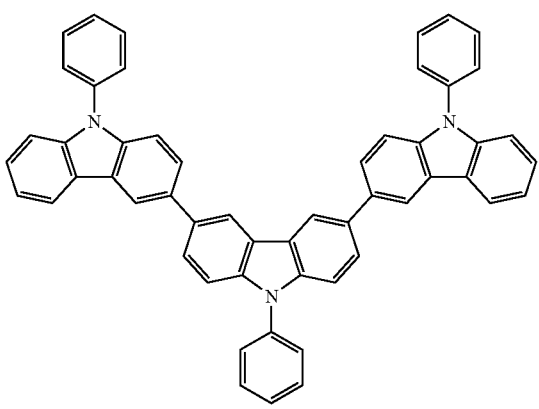

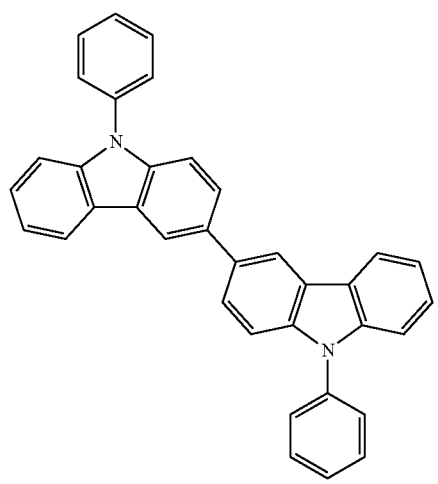

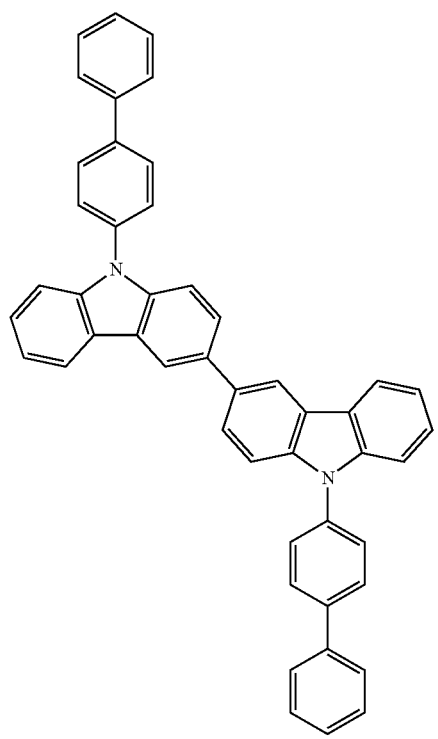

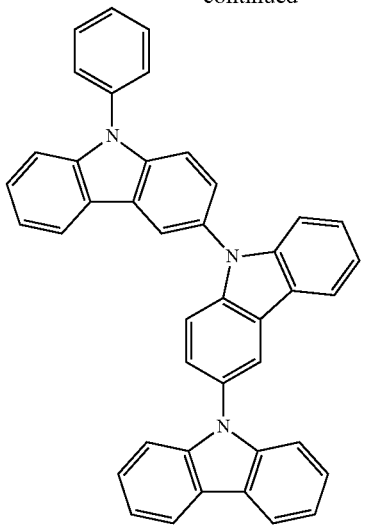

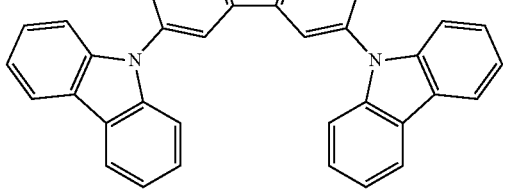

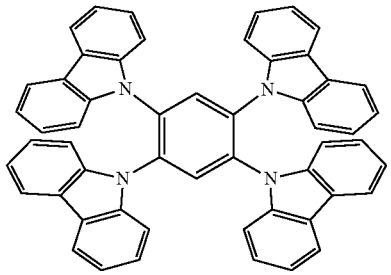

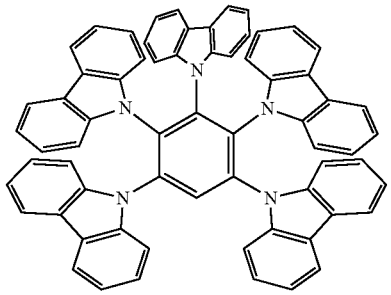

Exciton Barrier Layer

An exciton barrier layer inhibits excitons generated through recombination of holes and electrons in the light-emitting layer from being diffused to the charge transporting layer. In some embodiments, the exciton barrier layer enables effective confinement of excitons in the light-emitting layer. In some embodiments, the light emission efficiency of the device is enhanced. In some embodiments, the exciton barrier layer is adjacent to the light-emitting layer on any of the side of the anode and the side of the cathode, and on both the sides. In some embodiments, where the exciton barrier layer is on the side of the anode, the layer can be between the hole transporting layer and the light-emitting laver and adjacent to the light-emitting layer. In some embodiments, where the exciton barrier layer is on the side of the cathode, the layer can be between the light-emitting layer and the cathode and adjacent to the light-emitting layer. In some embodiments, a hole injection layer, an electron barrier layer, or a similar layer is between the anode and the exciton barrier layer that is adjacent to the light-emitting layer on the side of the anode. In some embodiments, a hole injection layer, an electron barrier layer, a hole barrier layer, or a similar layer is between the cathode and the exciton barrier layer that is adjacent to the light-emitting layer on the side of the cathode. In some embodiments, the exciton barrier layer comprises excited singlet energy and excited triplet energy, at least one of which is higher than the excited singlet energy and the excited triplet energy of the light-emitting material, respectively.

Hole Transporting Layer

The hole transporting layer comprises a hole transporting material. In some embodiments, the hole transporting layer is a single layer. In some embodiments, the hole transporting layer comprises a plurality layers.

In some embodiments, the hole transporting material has one of injection or transporting property of holes and barrier property of electrons. In some embodiments, the hole transporting material is an organic material. In some embodiments, the hole transporting material is an inorganic material. Examples of known hole transporting materials that may be used herein include but are not limited to a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer, or a combination thereof. In some embodiments, the hole transporting material is selected from a porphyrin compound, an aromatic tertiary amine compound, and a styrylamine compound. In some embodiments, the hole transporting material is an aromatic tertiary amine compound. Preferred compound examples for use as the hole transporting material are shown below.

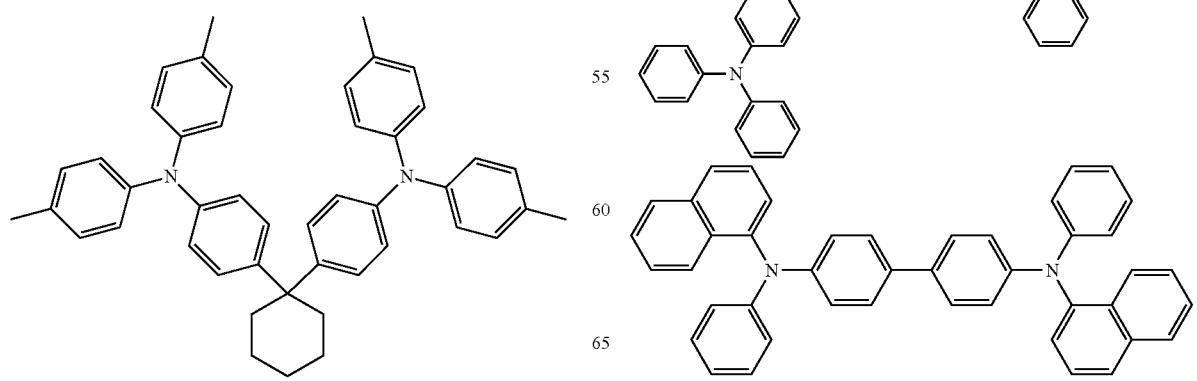

89
-continued
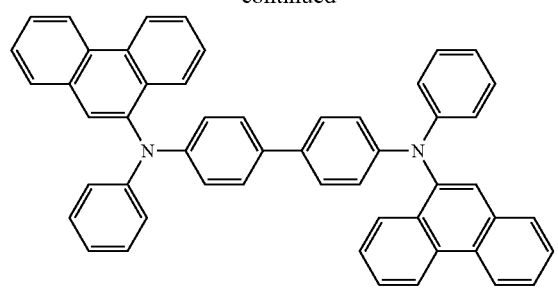
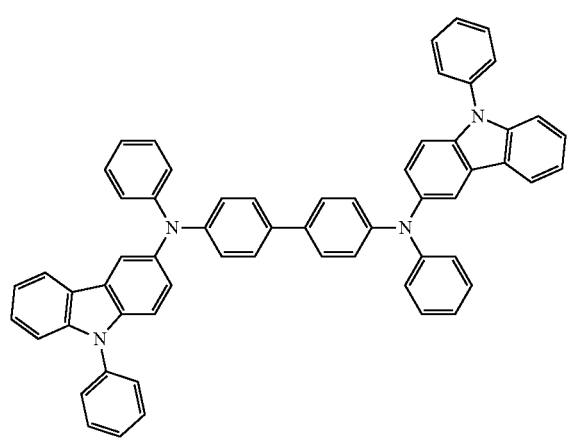
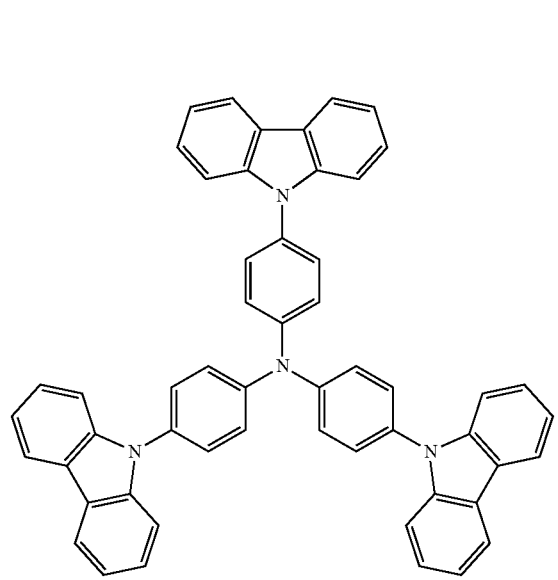
90
-continued
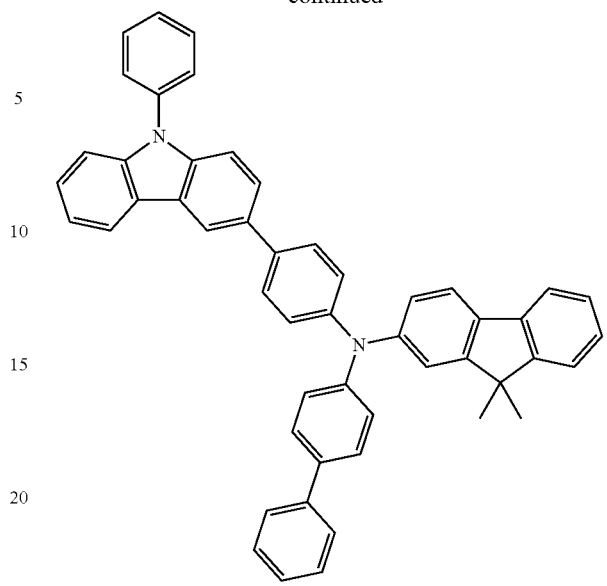
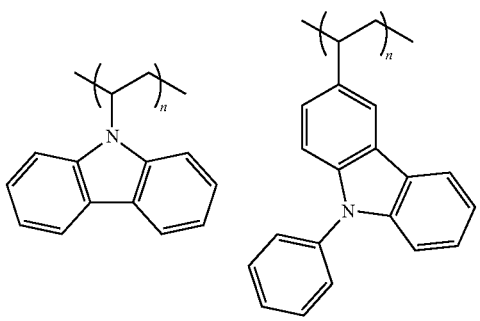
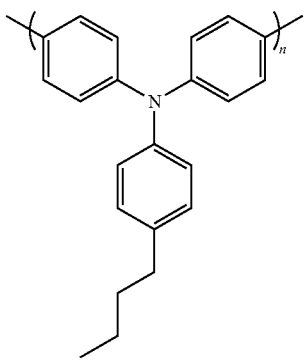
Electron Transporting Layer
The electron transporting layer comprises an electron transporting material. In some embodiments, the electron transporting layer is a single layer. In some embodiments, the electron transporting layer comprises a plurality of layer.

In some embodiments, the electron transporting material needs only to have a function of transporting electrons, which are injected from the cathode, to the light-emitting layer. In some embodiments, the electron transporting material also function as a hole barrier material. Examples of the electron transporting layer that may be used herein include but are not limited to a nitro-substituted fluorene derivative, a diphenylquinone derivative, a thiopyran dioxide derivative, carbodiimide, a fluorenylidene methane derivative, anthraquinodimethane, an anthrone derivatives, an azole derivative, an azine derivative, an oxadiazole derivative, or a combination thereof, or a polymer thereof. In some embodiments, the electron transporting material is a thiadiazole derivative, or a quinoxaline derivative. In some embodiments, the electron transporting material is a polymer material. Preferred compound examples for use as the electron transporting material are shown below.

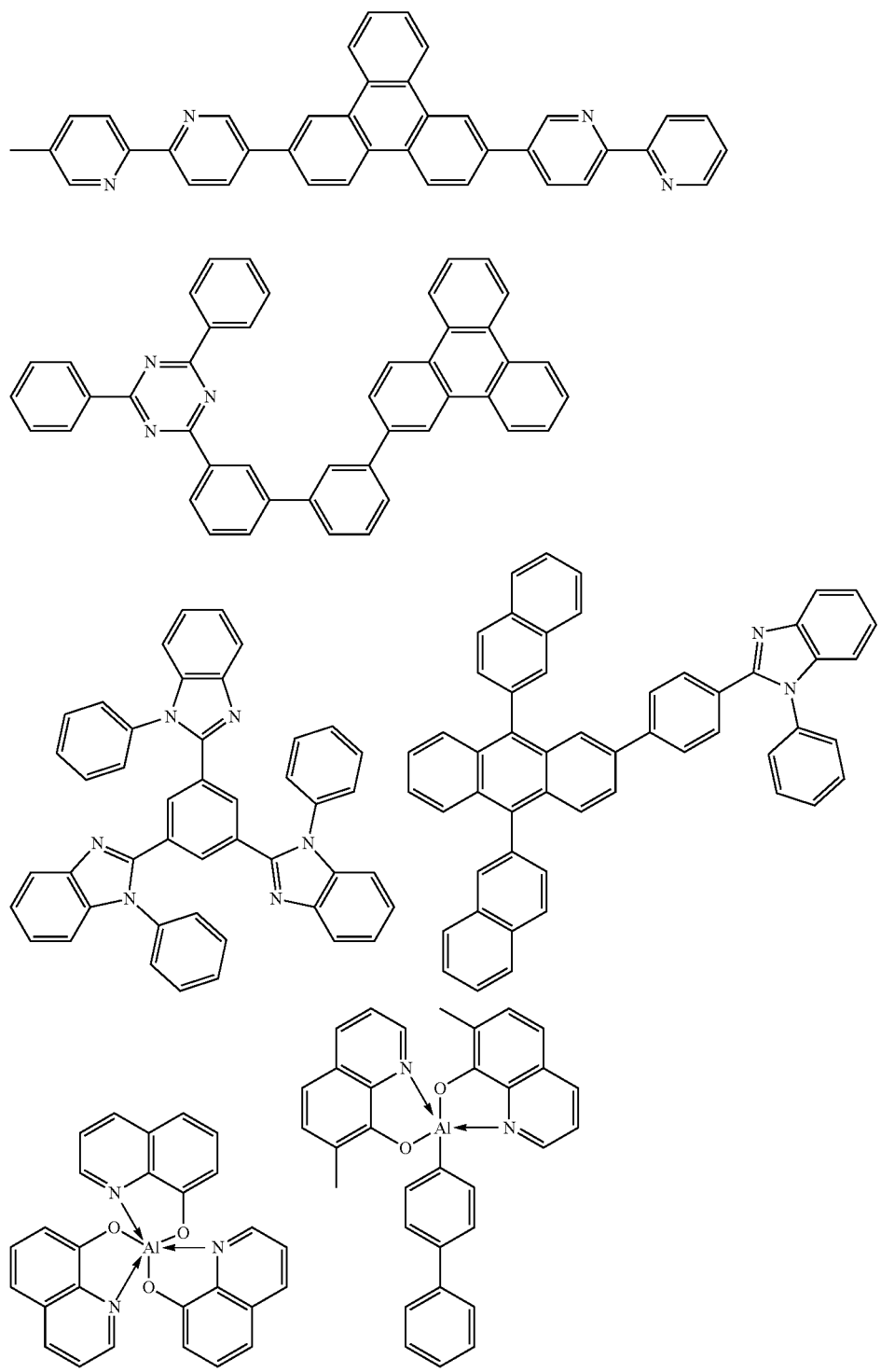

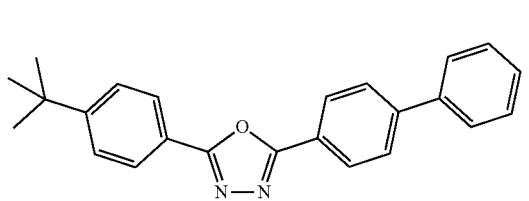
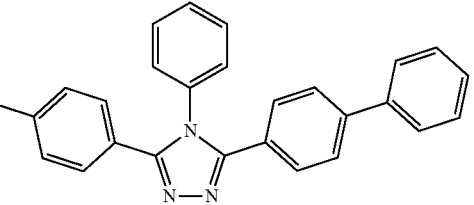

Hereinunder compound examples preferred as a material that can be added to the organic layers are shown. For example, these can be added as a stabilization material.

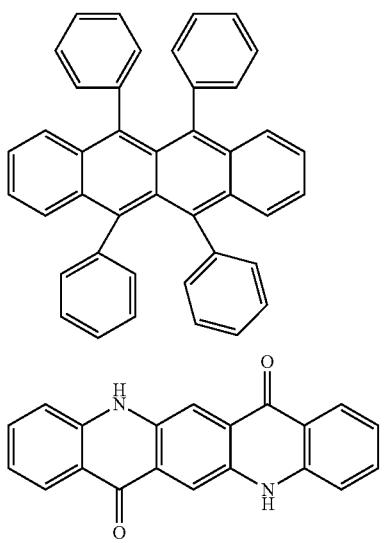

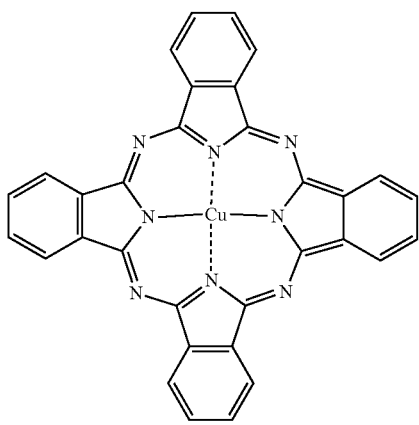

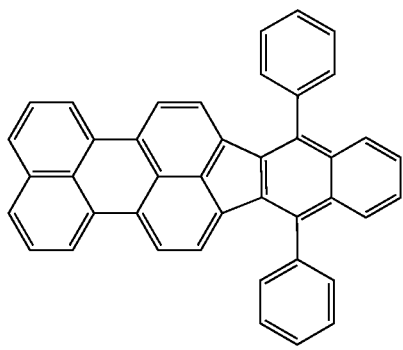

-continued

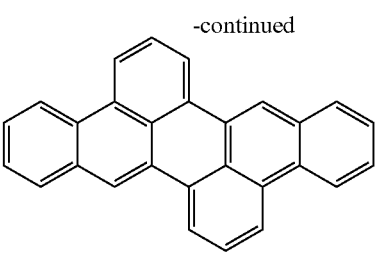

Preferred materials for use in the organic electroluminescent device are specifically shown. However, the materials usable in the invention should not be limitatively interpreted by the following exemplary compounds. Compounds that are exemplified as materials having a specific function can also be used as materials having any other function.

Devices

In some embodiments, an light emitting layer is incorporated into a device. For example, the device includes, but is not limited to an OLED bulb, an OLED lamp, a television screen, a computer monitor, a mobile phone, and a tablet.

In some embodiments, an electronic device comprises an OLED comprising an anode, a cathode, and at least one organic layer comprising a light emitting layer between the anode and the cathode.

In some embodiments, compositions described herein may be incorporated into various light-sensitive or light-activated devices, such as a OLEDs or photovoltaic devices. In some embodiments, the composition may be useful in facilitating charge transfer or energy transfer within a device and/or as a hole-transport material. The device may be, for example, an organic light-emitting diode (OLED), an organic integrated circuit (O-IC), an organic field-effect transistor (O-FET), an organic thin-film transistor (O-TFT), an organic light-emitting transistor (O-LET), an organic solar cell (O-SC), an organic optical detector, an organic photoreceptor, an organic field-quench device (O-FQD), a light-emitting electrochemical cell (LEC) or an organic laser diode (O-laser).

Bulbs or Lamps

In some embodiments, an electronic device comprises an OLED comprising an anode, a cathode, and at least one organic layer comprising a light emitting layer between the anode and the cathode.

In some embodiments, a device comprises OLEDs that differ in color. In some embodiments, a device comprises an array comprising a combination of OLEDs. In some embodiments, the combination of OLEDs is a combination of three colors (e.g., RGB). In some embodiments, the combination of OLEDs is a combination of colors that are not red, green, or blue (for example, orange and yellow green). In some embodiments, the combination of OLEDs is a combination of two, four, or more colors.

In some embodiments, a device is an OLED light comprising.
- a circuit board having a first side with a mounting surface and an opposing second side, and defining at least one aperture;
- at least one OLED on the mounting surface, the at least one OLED configured to emanate light, comprising:
  - an anode, a cathode, and at least one organic layer comprising a light emitting layer between the anode and the cathode;
- a housing for the circuit board; and
- at least one connector arranged at an end of the housing, the housing and the connector defining a package adapted for installation in a light fixture.

In some embodiments, the OLED light comprises a plurality of OLEDs mounted on a circuit board such that light emanates in a plurality of directions. In some embodiments, a portion of the light emanated in a first direction is deflected to emanate in a second direction. In some embodiments, a reflector is used to deflect the light emanated in a first direction.

Displays or Screens

In some embodiments, the compounds of the invention can be used in a screen or a display. In some embodiments, the compounds of the invention are deposited onto a substrate using a process including, but not limited to, vacuum evaporation, deposition, vapor deposition, or chemical vapor deposition (CVD). In some embodiments, the substrate is a photoplate structure useful in a two-sided etch provides a unique aspect ratio pixel. The screen (which may also be referred to as a mask) is used in a process in the manufacturing of OLED displays. The corresponding artwork pattern design facilitates a very steep and narrow tie-bar between the pixels in the vertical direction and a large, sweeping bevel opening in the horizontal direction. This allows the close patterning of pixels needed for high definition displays while optimizing the chemical deposition onto a TFT backplane.

The internal patterning of the pixel allows the construction of a 3-dimensional pixel opening with varying aspect ratios in the horizontal and vertical directions. Additionally, the use of imaged "stripes" or halftone circles within the pixel area inhibits etching in specific areas until these specific patterns are undercut and fall off the substrate. At that point the entire pixel area is subjected to a similar etch rate but the depths are varying depending on the halftone pattern. Varying the size and spacing of the halftone pattern allows etching to be inhibited at different rates within the pixel allowing for a localized deeper etch needed to create steep vertical bevels.

A preferred material for the deposition mask is invar. Invar is a metal alloy that is cold rolled into long thin sheet in a steel mill. Invar cannot be electrodeposited onto a rotating mandrel as the nickel mask. A preferred and more cost feasible method for forming the open areas in the mask used for deposition is through a wet chemical etching.

In some embodiments, a screen or display pattern is a pixel matrix on a substrate. In some embodiments, a screen or display pattern is fabricated using lithography (e.g., photolithography and e-beam lithography). In some embodiments, a screen or display pattern is fabricated using a wet chemical etch. In further embodiments, a screen or display pattern is fabricated using plasma etching.

Methods of Manufacturing Devices Using the Disclosed Compounds

An OLED display is generally manufactured by forming a large mother panel and then cutting the mother panel in units of cell panels. In general, each of the cell panels on the mother panel is formed by forming a thin film transistor (TFT) including an active layer and a source/drain electrode on a base substrate, applying a planarization film to the TFT, and sequentially forming a pixel electrode, a light-emitting layer, a counter electrode, and an encapsulation layer, and then is cut from the mother panel.

An OLED display is generally manufactured by forming a large mother panel and then cutting the mother panel in units of cell panels. In general, each of the cell panels on the mother panel is formed by forming a thin film transistor (TFT) including an active layer and a source/drain electrode on a base substrate, applying a planarization film to the TFT, and sequentially forming a pixel electrode, a light-emitting layer, a counter electrode, and an encapsulation layer, and then is cut from the mother panel.

In another aspect, provided herein is a method of manufacturing an organic light-emitting diode (OLED) display, the method comprising:
- forming a barrier layer on a base substrate of a mother panel;
- forming a plurality of display units in units of cell panels on the barrier layer;
- forming an encapsulation layer on each of the display units of the cell panels:
- applying an organic film to an interface portion between the cell panels.

In some embodiments, the barrier layer is an inorganic film formed of, for example, SiNx, and an edge portion of the barrier layer is covered with an organic film formed of polyimide or acryl. In some embodiments, the organic film helps the mother panel to be softly cut in units of the cell panel.

In some embodiments, the thin film transistor (TFT) layer includes a light-emitting layer, a gate electrode, and a source/drain electrode. Each of the plurality of display units may include a thin film transistor (TFT) layer, a planarization film formed on the TFT layer, and a light-emitting unit formed on the planarization film, wherein the organic film applied to the interface portion is formed of a same material as a material of the planarization film and is formed at a same time as the planarization film is formed. In some embodiments, a light-emitting unit is connected to the TFT layer with a passivation layer and a planarization film therebetween and an encapsulation layer that covers and protects the light-emitting unit. In some embodiments of the method of manufacturing, the organic film contacts neither the display units nor the encapsulation layer.

Each of the organic film and the planarization film may include any one of polyimide and acryl. In some embodiments, the barrier layer may be an inorganic film. In some embodiments, the base substrate may be formed of polyimide. The method may further include, before the forming of the barrier layer on one surface of the base substrate formed of polyimide, attaching a carrier substrate formed of a glass material to another surface of the base substrate, and before the cutting along the interface portion, separating the carrier substrate from the base substrate. In some embodiments, the OLED display is a flexible display.

In some embodiments, the passivation layer is an organic film disposed on the TFT layer to cover the TFT layer. In some embodiments, the planarization film is an organic film formed on the passivation layer. In some embodiments, the planarization film is formed of polyimide or acryl, like the organic film formed on the edge portion of the barrier layer. In some embodiments, the planarization film and the organic film are simultaneously formed when the OLED display is manufactured. In some embodiments, the organic film may be formed on the edge portion of the barrier layer such that a portion of the organic film directly contacts the base substrate and a remaining portion of the organic film contacts the barrier layer while surrounding the edge portion of the barrier layer.

In some embodiments, the light-emitting layer includes a pixel electrode, a counter electrode, and an organic light-emitting layer disposed between the pixel electrode and the counter electrode. In some embodiments, the pixel electrode is connected to the source/drain electrode of the TFT layer.

In some embodiments, when a voltage is applied to the pixel electrode through the TFT layer, an appropriate voltage is formed between the pixel electrode and the counter electrode, and thus the organic light-emitting layer emits light, thereby forming an image. Hereinafter, an image forming unit including the TFT layer and the light-emitting unit is referred to as a display unit.

In some embodiments, the encapsulation layer that covers the display unit and prevents penetration of external moisture may be formed to have a thin film encapsulation structure in which an organic film and an inorganic film are alternately stacked. In some embodiments, the encapsulation layer has a thin film encapsulation structure in which a plurality of thin films are stacked. In some embodiments, the organic film applied to the interface portion is spaced apart from each of the plurality of display units. In some embodiments, the organic film is formed such that a portion of the organic film directly contacts the base substrate and a remaining portion of the organic film contacts the barrier layer while surrounding an edge portion of the barrier layer.

In one embodiment, the OLED display is flexible and uses the soft base substrate formed of polyimide. In some embodiments, the base substrate is formed on a carrier substrate formed of a glass material, and then the carrier substrate is separated.

In some embodiments, the barrier layer is formed on a surface of the base substrate opposite to the carrier substrate. In one embodiment, the barrier layer is patterned according to a size of each of the cell panels. For example, while the base substrate is formed over the entire surface of a mother panel, the barrier layer is formed according to a size of each of the cell panels, and thus a groove is formed at an interface portion between the barrier layers of the cell panels. Each of the cell panels can be cut along the groove.

In some embodiments, the method of manufacture further comprises cutting along the interface portion, wherein a groove is formed in the barrier layer, wherein at least a portion of the organic film is formed in the groove, and wherein the groove does not penetrate into the base substrate. In some embodiments, the TFT layer of each of the cell panels is formed, and the passivation layer which is an inorganic film and the planarization film which is an organic film are disposed on the TFT layer to cover the TFT layer. At the same time as the planarization film formed of, for example, polyimide or acryl is formed, the groove at the interface portion is covered with the organic film formed of, for example, polyimide or acryl. This is to prevent cracks from occurring by allowing the organic film to absorb an impact generated when each of the cell panels is cut along the groove at the interface portion. That is, if the entire barrier layer is entirely exposed without the organic film, an impact generated when each of the cell panels is cut along the groove at the interface portion is transferred to the barrier layer, thereby increasing the risk of cracks. However, in one embodiment, since the groove at the interface portion between the barrier layers is covered with the organic film and the organic film absorbs an impact that would otherwise be transferred to the barrier layer, each of the cell panels may be softly cut and cracks may be prevented from occurring in the barrier layer. In one embodiment, the organic film covering the groove at the interface portion and the planarization film are spaced apart from each other. For example, if the organic film and the planarization film are connected to each other as one layer, since external moisture may penetrate into the display unit through the planarization film and a portion where the organic film remains, the organic film and the planarization film are spaced apart from each other such that the organic film is spaced apart from the display unit.

In some embodiments, the display unit is formed by forming the light-emitting unit, and the encapsulation layer is disposed on the display unit to cover the display unit. As such, once the mother panel is completely manufactured, the carrier substrate that supports the base substrate is separated from the base substrate. In some embodiments, when a laser beam is emitted toward the carrier substrate, the carrier substrate is separated from the base substrate due to a difference in a thermal expansion coefficient between the carrier substrate and the base substrate.

In some embodiments, the mother panel is cut in units of the cell panels. In some embodiments, the mother panel is cut along an interface portion between the cell panels by using a cutter. In some embodiments, since the groove at the interface portion along which the mother panel is cut is covered with the organic film, the organic film absorbs an impact during the cutting. In some embodiments, cracks may be prevented from occurring in the barrier layer during the cutting.

In some embodiments, the methods reduce a defect rate of a product and stabilize its quality.

Another aspect is an OLED display including: a barrier layer that is formed on a base substrate; a display unit that is formed on the barrier layer; an encapsulation layer that is formed on the display unit; and an organic film that is applied to an edge portion of the barrier layer.

EXAMPLES

The features of the present invention will be described more specifically with reference to Synthesis Examples, Test Examples and Examples given below. The materials, processes, procedures and the like shown below may be appropriately modified unless they deviate from the substance of the invention. Accordingly, the scope of the invention is not construed as being limited to the specific examples shown below. Hereinunder the light emission characteristics were evaluated using a source meter (available from Keithley Instruments Corporation: 2400 series), a semiconductor parameter analyzer (available from Agilent Corporation, E5273A), an optical power meter device (available from Newport Corporation, 1930C), an optical spectroscope (available from Ocean Optics Corporation, USB2000), a spectroradiometer (available from Topcon Corporation, SR-3), a streak camera (available from Hamamatsu Photonics K.K., Model C4334), and an extended absolute quantum yield measurement device (available from Hamamatsu Photonics K.K., Quantaurus-QY Plus C13534-01).

(Synthesis Example 1) Synthesis of Compound 1

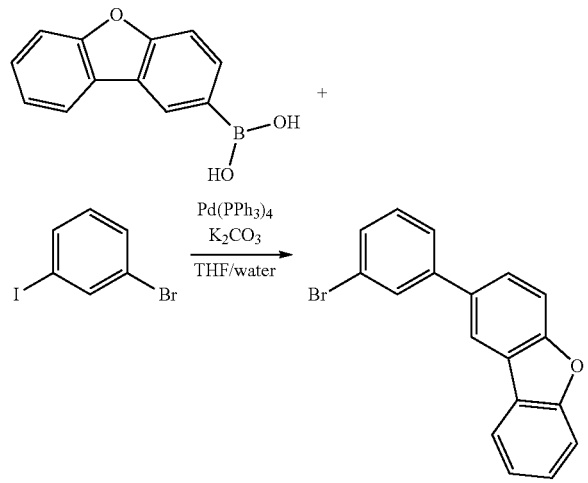

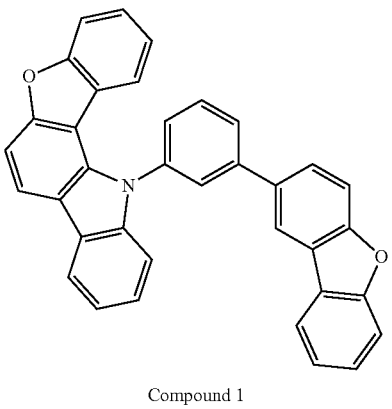

Compound 1

In a nitrogen atmosphere, dibenzo[b,d]furan-2-ylboronic acid (5 g, 23.58 mmol), 1-bromo-3-iodobenzene (8.01 g, 28.3 mmol), tetrakis(triphenylphosphine)palladium(0) (1.36 g, 1.18 mmol) and potassium carbonate (9.78 g, 70.74 mmol) were added to a mixed solution of tetrahydrofuran and pure water (60 ml/30 ml), and stirred at 75° C. for 16 hours. The reaction solution was cooled to room temperature, and chloroform was added thereto. The organic layer was washed twice with water, and dried with magnesium sulfate, and the solvent was removed. The resultant solid was purified through silica gel column chromatography (developing solvent: n-hexane) to give a white solid of 2-(3-bromophenyl)dibenzofuran (4.94 g, 65%).

$^1$H NMR (500 MHz, CDCl$_3$, δ): 8.11 (s, 1H), 8.00 (d, J=8 Hz, 1H), 7.82 (s, 1H), 7.63-7.59 (m, 4H), 7.49 (d, J=8 Hz, 2H), 7.39-7.33 (m, 2H).

MS (ASAP): 323.62 (M+H$^+$). Calcd for C$_{18}$H$_{11}$BrO: 322.00.

In a nitrogen atmosphere, 2-(3-bromophenyl)dibenzofuran (2.51 g, 7.77 mmol), 12H-benzofuro[3,2-a]carbazole (2.0 g, 7.77 mmol), tris(dibenzylideneacetone)dipalladium(0)(0.36 g, 0.39 mmol), tri-tert-butylphosphonium tetrafluoroborate (0.23 g, 0.78 mmol) and sodium tert-butoxide (1.49 g, 15.5 mmol) were added to 60 ml of toluene, and refluxed for 24 hours. The reaction solution was cooled to room temperature, and chloroform was added thereto. The resultant organic layer was washed twice with water, and dried with magnesium sulfate, and the solvent was removed. The resultant solid was purified through silica gel column chromatography (developing solvent: chloroform/n-hexane=⅕) and further recrystallized (toluene/methanol) to give a white solid of compound 1 (3.48 g, 90%).

$^1$H NMR (500 MHz, CDCl$_3$, δ): 8.28 (d, J=8 Hz, 1H), 8.21 (d, J=8 Hz, 1H), 8.06 (s, 1H), 7.97 (d, J=8 Hz, 1H), 7.88 (m, 2H), 7.79 (t, J=8 Hz, 1H), 7.70-7.65 (m, 8H), 7.46-7.26 (m, 4H), 6.90 (t, J=8 Hz, 1H), 5.93 (d, J=8 Hz, 1H).

MS (ASAP): 500.19 (M+H$^+$). Calcd for C$_{36}$H$_{21}$NO$_2$: 499.16.

(Synthesis Example 2) Synthesis of Compound 2

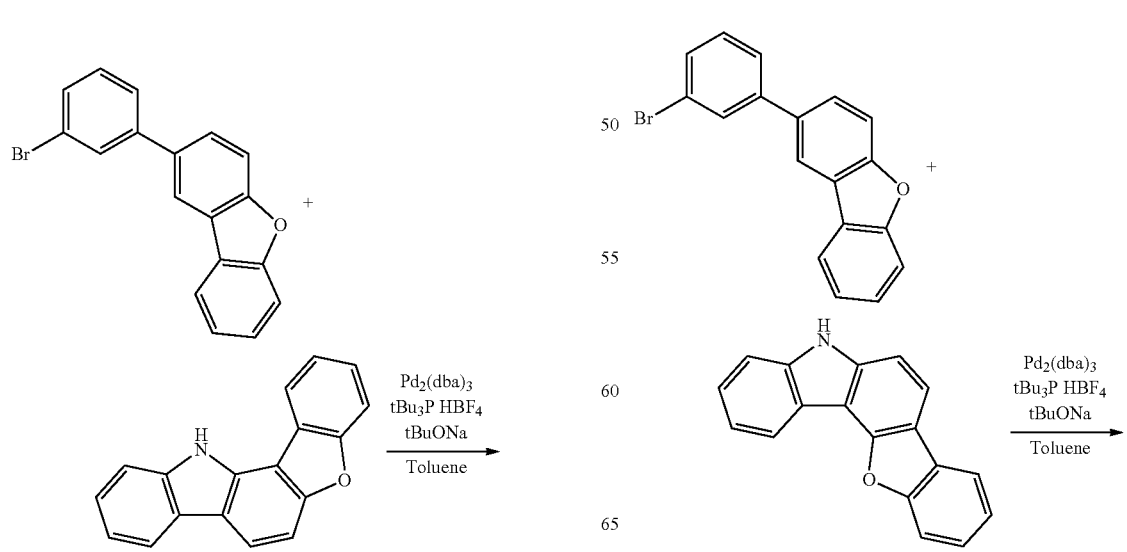

101
-continued

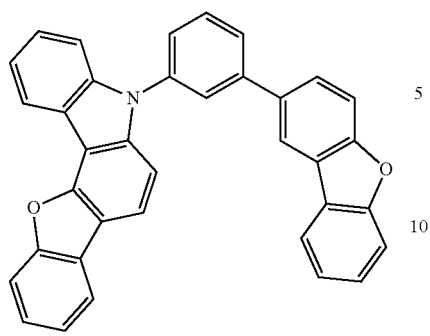

Compound 2

In a nitrogen atmosphere, 2-(3-bromophenyl)dibenzofuran (2.26 g, 7 mmol), 5H-benzofuro[3,2-c]carbazole (1.8 g, 7 mmol), tris(dibenzylideneacetone)dipalladium(0) (320 mg, 0.35 mmol), tri-tert-butylphosphonium tetrafluoroborate (205 mg, 0.7 mmol) and sodium tert-butoxide (1.35 g, 14 mmol) were added to 50 ml of toluene, and refluxed for 24 hours. The reaction solution was cooled to room temperature, and chloroform was added thereto. The resultant organic layer was washed twice with water, and dried with magnesium sulfate, and the solvent was removed. The resultant solid was purified through silica gel column chromatography (developing solvent: chloroform/n-hexane=⅑ to ¼). This was further recrystallized (toluene/hexane) to give a white solid of compound 2 (2.3 g, 66%).

$^1$H NMR (500 MHz, CDCl$_3$, δ): 8.61 (d, J=8 Hz, 1H), 8.23 (s, 1H), 8.00-7.94 (m, 4H), 7.84 (d, J=8 Hz, 1H), 7.76 (m, 3H), 7.67-7.34 (m, 11H).

MS (ASAP): 500.17 (M+H$^+$). Calcd for C$_{36}$H$_{21}$NO$_2$: 499.16.

(Synthesis Example 3) Synthesis of Compound 3

102
-continued

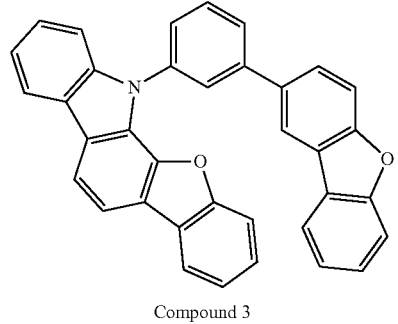

Compound 3

In a nitrogen atmosphere, 2-(3-bromophenyl)dibenzofuran (0.75 g, 2.33 mmol), 12H-benzofuro[2,3-a]carbazole (0.60 g, 2.33 mmol), tris(dibenzylideneacetone)dipalladium (0) (0.11 g, 0.12 mmol), tri-tert-butylphosphonium tetrafluoroborate (67 mg, 0.23 mmol) and sodium tert-butoxide (0.45 g, 4.66 mmol) were added to 20 ml of toluene, and refluxed for 24 hours. The reaction solution was cooled to room temperature, and chloroform was added thereto. The resultant organic layer was washed twice with water, and dried with magnesium sulfate, and the solvent was removed. The resultant solid was purified through silica gel column chromatography (developing solvent: chloroform/n-hexane=¼). This was further recrystallized (toluene/methanol) to give a white solid of compound 3 (0.521 g, 45%).

$^1$H NMR (400 MHz, CDCl$_3$, δ): 8.31 (s, 1H), 8.23 (d, 2H), 8.17 (d, J=8 Hz, 1H), 8.06 (d, J=8 Hz, 1H), 7.92-7.82 (m, 4H), 7.74 (m, 2H), 7.74 (d, J=9 Hz, 2H), 7.58 (d, J=8 Hz, 1H), 7.55-7.30 (m, 7H).

MS (ASAP): 500.38 (M+H$^{3o}$). Calcd for C$_{36}$H$_{21}$NO$_2$: 499.16.

(Synthesis Example 4) Synthesis of Compound 14

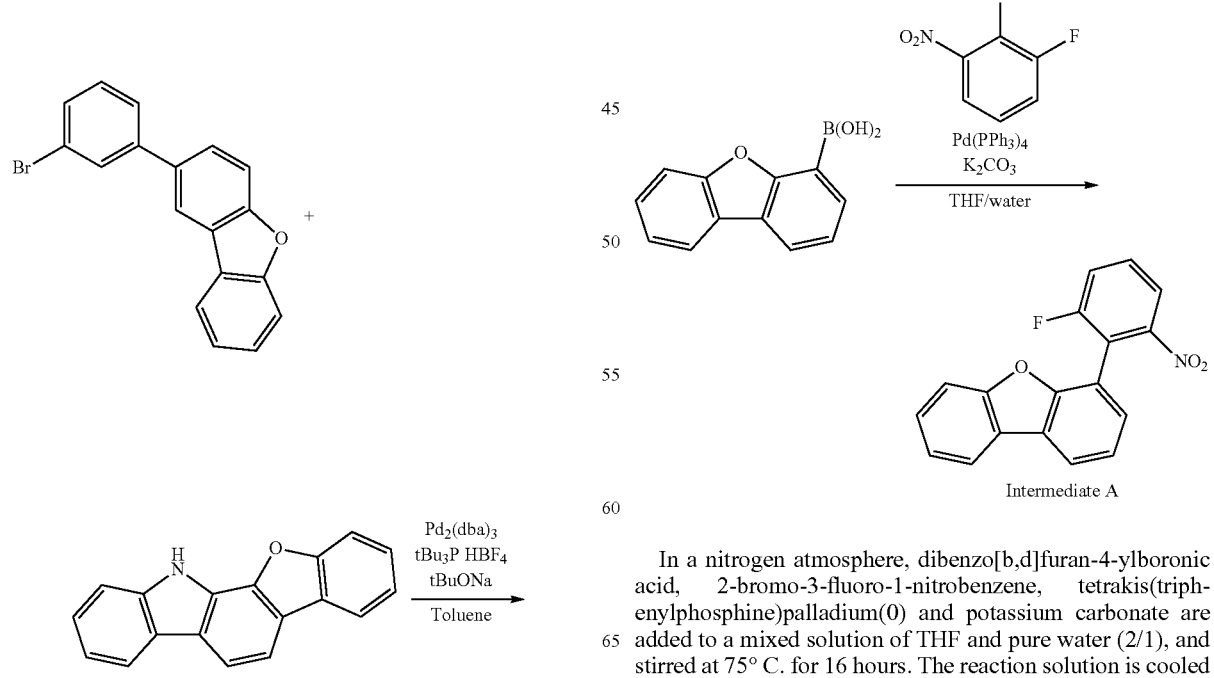

Intermediate A

In a nitrogen atmosphere, dibenzo[b,d]furan-4-ylboronic acid, 2-bromo-3-fluoro-1-nitrobenzene, tetrakis(triphenylphosphine)palladium(0) and potassium carbonate are added to a mixed solution of THF and pure water (2/1), and stirred at 75° C. for 16 hours. The reaction solution is cooled to room temperature, and chloroform is added thereto. The organic layer was washed twice with water, and dried with magnesium sulfate, and the solvent was removed. The resultant solid was purified through silica gel column chromatography (developing solvent: n-hexane/chloroform=6/4) to give an intermediate A as a white solid.

In a nitrogen atmosphere, the intermediate B. palladium acetate, tricyclohexyl phosphine, and cesium carbonate are added to toluene and refluxed for 24 hours. The reaction solution is cooled to room temperature, the organic layer is washed twice with water, dried with magnesium sulfate, and the solvent is removed. The resultant solid is purified through silica gel column chromatography (developing solvent: chloroform/n-hexane=1/1) to give an intermediate C as a white solid.

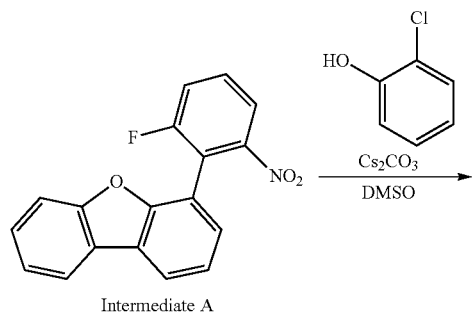

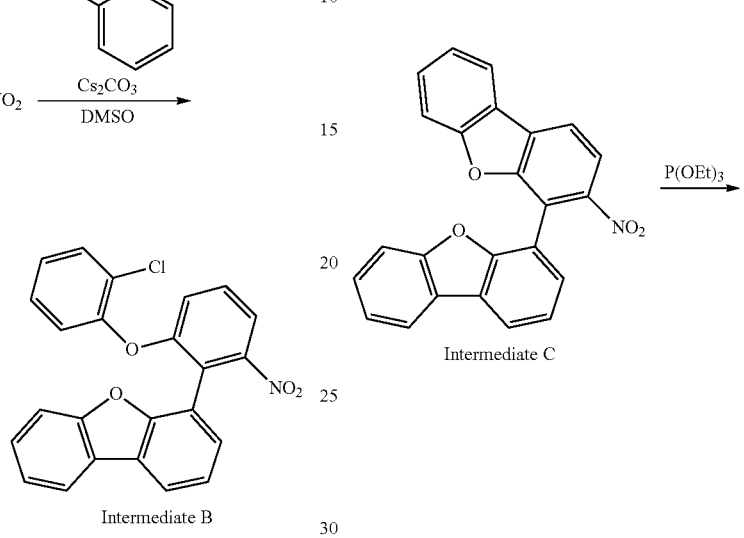

In a nitrogen atmosphere, the intermediate A, 2-chlorophenol and cesium carbonate was added to dimethyl sulfoxide (DMSO), and stirred at 150° C. for 16 hours. The reaction solution is cooled to room temperature, water is added thereto, and the precipitate is taken out through filtration. The resultant residue is washed with water. The resultant solid is purified through silica gel column chromatography (developing solvent: n-hexane/chloroform=6/4) to give an intermediate B as a white solid.

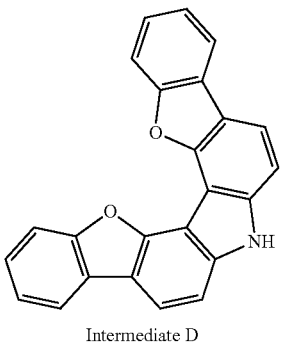

Intermediate D

In a nitrogen atmosphere, the intermediate C is added to triethyl phosphite, and stirred at 150° C. for 16 hours. Triethyl phosphite is removed, methanol is added, and the resultant solid is further washed with methanol. The solid is purified through silica gel column chromatography (developing solvent: n-hexane/chloroform=4/6) to give a white solid of an intermediate D.

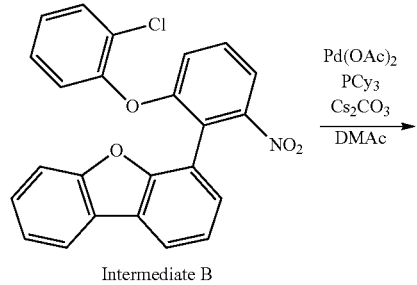

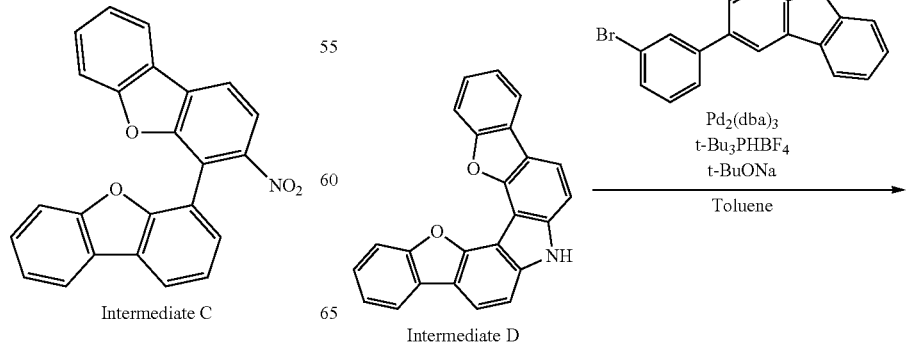

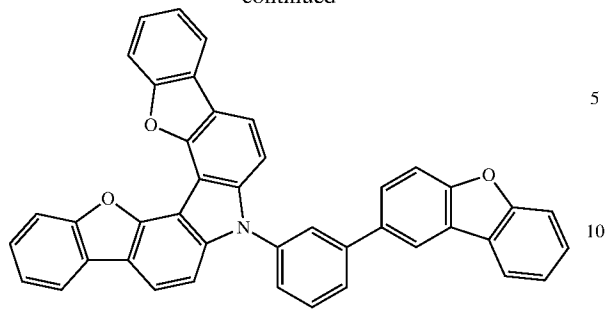

Compound 14

In a nitrogen atmosphere, the intermediate D, 2-(3-bromophenyl)dibenzofuran, tris(dibenzylideneacetone)dipalladium(0), tri-tert-butylphosphonium tetrafluoroborate and sodium tert-butoxide are added to toluene, and refluxed for 24 hours. The reaction solution is cooled to room temperature, and chloroform is added thereto. The resultant organic layer is washed twice with water, dried with magnesium sulfate, and the solvent is removed. The resultant solid is purified through silica gel column chromatography (developing solvent: chloroform/n-hexane=4/6). This is further recrystallized (toluene/methanol) to give a compound 14 as a white solid.

(Test Example) Measurement of Hole Mobility

On a glass substrate having, as formed thereon, an anode of indium tin oxide (ITO) having a thickness of 50 nm, HAT-CN was deposited at a thickness of 10 nm, then α-NPD was deposited at a thickness of 10 nm, the compound 1 was formed at a thickness of 100 nm, and then aluminum (Al) was deposited at a thickness of 100 nm to form a cathode, thereby preparing a hole mobility measurement device 1. The constituent thin films were laminated at a vacuum degree of $5.0 \times 10^{-5}$ Pa in a vacuum evaporation method.

In place of the compound 1, the compound 2, the compound 3 and a comparative compound A were used to prepare hole mobility measurement devices 2 to 4, respectively.

The current density and the voltage characteristics of the thus-prepared hole mobility measurement devices 1 to 4 were measured, and according to the following equation of space-charge limited current (SCLC), the hole mobility was calculated, and the results are shown in the following Table. The devices 1 to 3 using the compounds 1 to 3, respectively, represented by the general formula (1) attained a hole mobility greater by one order of magnitude or more than the device 4 using the comparative compound A. From this, it was confirmed that the compound represented by the general formula (1) has good hole transportation performance as a host material.

$$J_{SCLC} = \frac{9}{8}\varepsilon_r\varepsilon_0\mu_{(SCLC)}\frac{V^2}{d^3}$$

J: current
$\varepsilon_r$: relative permittivity
$\varepsilon_0$: vacuum permittivity
μ: hole mobility
d: film thickness
V: applied voltage

TABLE 1

| Hole Mobility Measurement Device | Host Material | Hole Mobility (cm$^2$/Vs) |
|---|---|---|
| Device 1 (the invention) | Compound 1 | $9.3 \times 10^{-6}$ |
| Device 2 (the invention) | Compound 2 | $4.4 \times 10^{-5}$ |
| Device 3 (the invention) | Compound 3 | $1.5 \times 10^{-5}$ |
| Device 4 (comparative example) | Comparative compound A | $2.1 \times 10^{-7}$ |

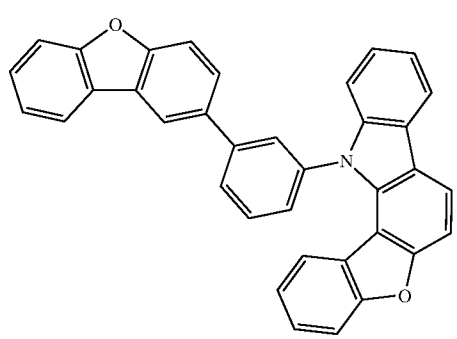

Compound 1

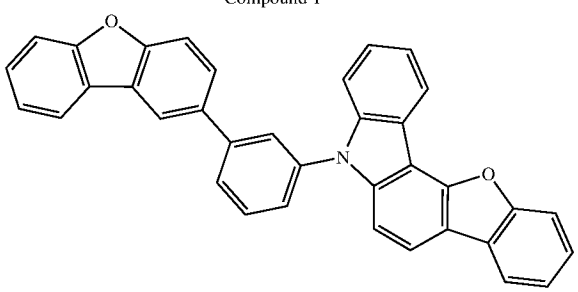

Compound 2

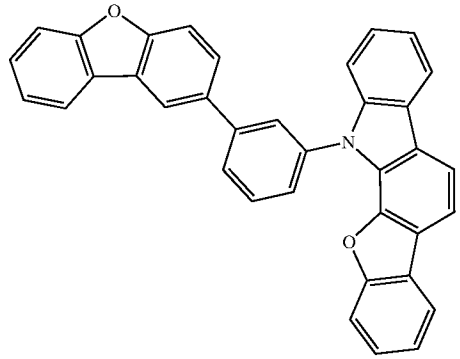

Compound 3

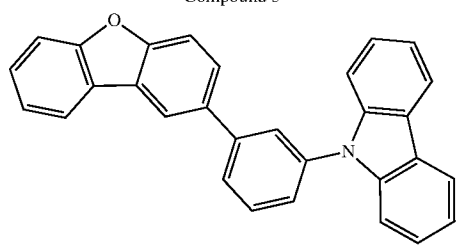

Comparative Compound A

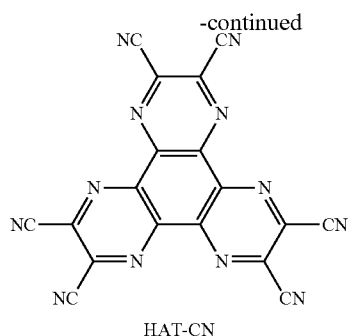

HAT-CN

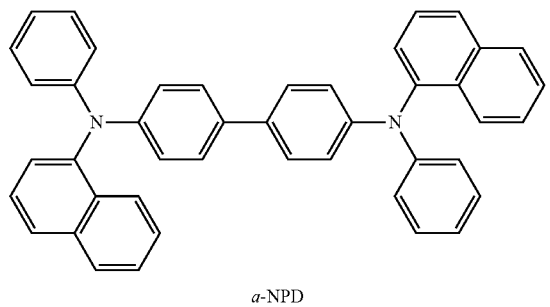 [SMILES: c1ccc(N(c2ccc(-c3ccc(N(c4ccccc4)c4cccc5ccccc45)cc3)cc2)c2cccc3ccccc23)cc1]

α-NPD (Example 1) Production and Evaluation of Organic Photoluminescent Device

According to a vacuum evaporation method, the compound 1 and TADF1 were vapor-deposited on a rotating substrate from different evaporation sources at a vacuum degree of $5.0\times10^{-5}$ Pa to form a thin-film having a thickness of 75 nm in which the concentration of TADF1 was 20% by mass, thereby producing an organic photoluminescent device. The device is referred to as FL device 1.

In place of the compound 1 and TADF1, materials shown in the following Table were used to produce FL devices 2 to 8.

The thus-produced FL devices 1 to 8 were analyzed to measure the photoluminescence quantum yield (PLQY) using 280-nm excitation light, and the results are shown in the following Table. The mixed film in which the host material of the compounds 1 to 3 of the general formula (1) was doped with a delayed fluorescent material attained a good photoluminescence quantum yield. On the other hand, the photoluminescence quantum yield of the mixed film in which the comparative compound B was used as a host material was extremely low. This suggests that the comparative compound not having a benzofurocarbazole group and a dibenzofurano group cannot function as a host material for a delayed fluorescent material.

TABLE 2

| Organic Photolaminescent Device | Host Material | Dopant Material | Photoluminescence Quantum Yield (%) |
| --- | --- | --- | --- |
| FL device 1 (the invention) | Compound 1 | TADF1 | 83.5 |
| FL device 2 (the invention) | Compound 2 | TADF1 | 67.1 |
| FL device 3 (the invention) | Compound 3 | TADF1 | 77.0 |
| FL device 4 (the invention) | Comparative Compound B | TADF1 | 2 7 |
| FL device 5 (the invention) | Compound 1 | TADF2 | 86.1 |
| FI, device 6 (the invention) | Compound 2 | TADF2 | 77.5 |

TABLE 2-continued

| Organic Photolaminescent Device | Host Material | Dopant Material | Photoluminescence Quantum Yield (%) |
| --- | --- | --- | --- |
| FL device 7 (the invention) | Compound 3 | TADF2 | 88.1 |
| FL device 8 (comparative example) | Comparative Compound B | TADF2 | 12.4 |

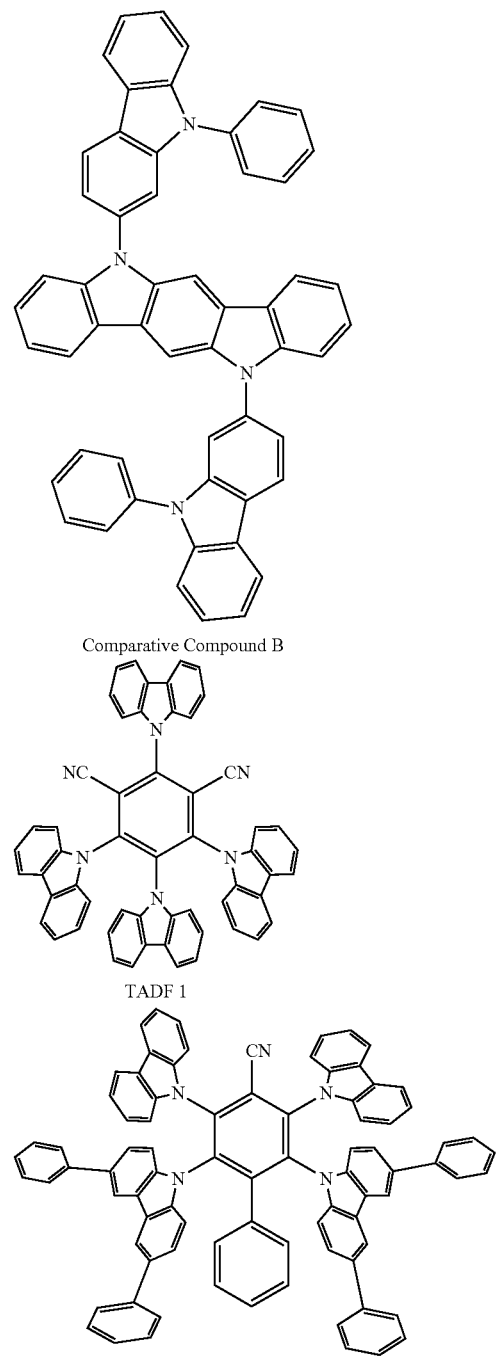

Comparative Compound B

TADF 1

TADF 2

(Example 2) Production and Evaluation of Organic Electroluminescent Device

On a glass substrate having, as formed thereon, an anode of indium tin oxide (ITO) having a thickness of 50 nm, the following thin films were laminated at a vacuum degree of $5.0 \times 10^{-5}$ Pa in a vacuum evaporation method to produce an organic electroluminescent device.

First, on the ITO, HAT-CN was deposited at a thickness of 10 nm, then α-NPD was deposited thereon at a thickness of 30 nm. Next, Tris-PCz was formed at a thickness of 10 nm, and PYD2Cz was formed thereon at a thickness of 5 nm. Next, a delayed fluorescent material (TADF3) and the compound 1 were co-evaporated from different evaporation sources to form a layer having a thickness of 30 nm to be a light-emitting layer. At that time, the content of the delayed fluorescent material was 45% by mass, and the content of the compound 1 was 55% by mass. Next, SF3-TRZ was formed at a thickness of 10 nm, and then Liq and SF3-TRZ were co-evaporated from different evaporation sources to form a layer having thickness of 30 nm. The content of Liq and SF3-TRZ in the layer was 30% by mass and 70% by mass, respectively. Further, Liq was formed at a thickness of 2 nm, and then aluminum (Al) was deposited at a thickness of 100 nm to form a cathode, thereby producing an organic electroluminescent device. The device is referred to as EL device 1.

The comparative compound A was used in place of the compound 1 to produce EL device 2.

The driving voltage at a current density 12.6 mA/cm$^2$ of each of the thus-produced organic electroluminescent devices was measured. The driving voltage of the EL device 1 (the invention) was lower by 0.4 eV than that of the EL device 2 (comparative example). From this, it was confirmed that the organic electroluminescent device using a compound represented by the general formula (1) as a host material for a delayed fluorescent material has good electroconductivity.

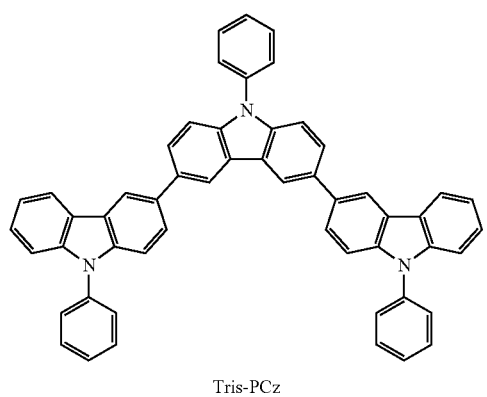

Tris-PCz

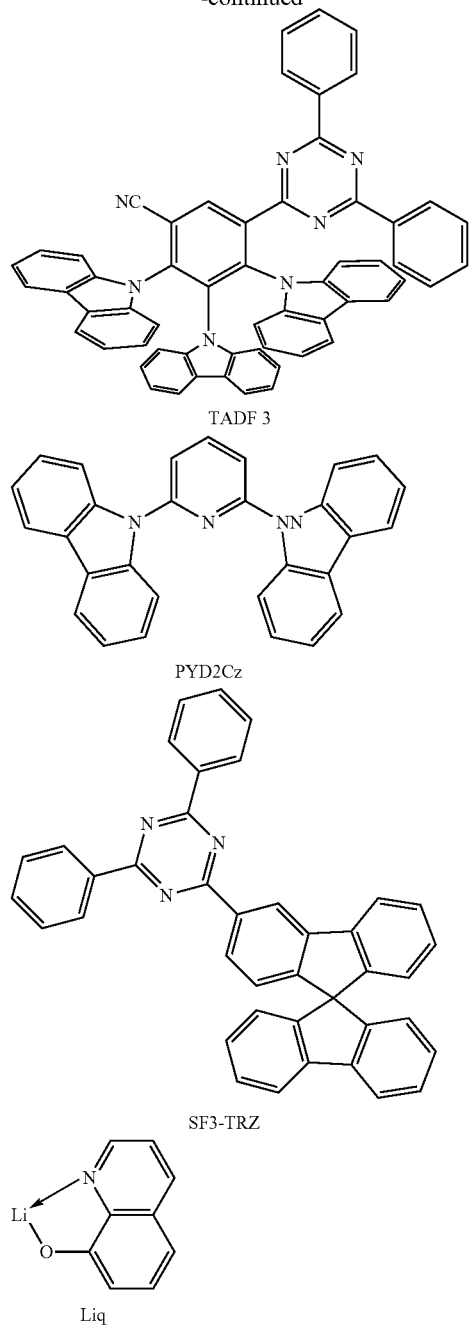

TADF 3

PYD2Cz

SF3-TRZ

Liq

(Example 3) Production and Evaluation of Another Organic Electroluminescent Device Each of the compound 2 and the compound 3 was used in place of the compound 1 in Example 2 to produce EL devices 3 and 4.

The driving voltage of each EL device was measured according to the same method as in Example 2. In the following Table, a difference of the driving voltage of each EL device, based on the driving voltage of the EL device 2, was measured, and the results are shown as "driving voltage". A smaller value means that the driving voltage is lower. In addition, the EL devices 2 to 4 were continuously driven at a current density 12.6 mA/cm$^2$, and the time taken until the emission luminance reduced to 95% of the initial luminescence was measured. Results of a ratio of the measured time of each EL device relative to the measured time of the EL device 2 are shown in the following table as "device lifetime". A larger value means that the device lifetime is longer.

It was observed that the EL devices 3 and 4 using the compounds 2 and 3, respectively, of the general formula (1) could drive at a lower voltage as compared with the EL device 2 using the comparative compound A. In addition, it was confirmed that the EL devices 3 and 4 using the compounds 2 and 3, respectively, of the general formula (1) could prevent luminance degradation as compared with the EL device 2 using the comparative compound A. From this, it was confirmed that the organic electroluminescent device using a compound represented by the general formula (1) as a host material for a delayed fluorescent material has good electroconductivity and device durability.

TABLE 3

| Organic Electroluminescent Device | Host Material | Driving Voltage (V) [difference from EL device 4] | Device Lifetime [ratio to EL device 4] |
|---|---|---|---|
| EL device 2 (comparative example) | Comparative compound A | 0 (reference) | 1 (reference) |
| EL device 3 (the invention) | Compound 2 | −0.2 | 1.67 |
| EL device 4 (the invention) | Compound 3 | −0.2 | 1.47 |

(Example 4) Production and Evaluation of Organic Electroluminescent Device Using Delayed Fluorescent Material as Assist Dopant Next, the light-emitting layer in Example 2 was changed to a light-emitting layer formed by co-evaporation of a delayed fluorescent material (TADF4), the compound 3 and D35 each from different evaporation sources, and the other was the same as in Example 2 to product EL device 5. At that time, in the light-emitting layer, the content of the delayed fluorescent material was 30% by mass, the content of the compound 3 was 69.5% by mass, and the content of D35 was 0.5% by mass. The lowest excited singlet energy of D35 was lower than that of the delayed fluorescent material (TADF4).

In addition, EL devices 6 and 7 were produced by changing the content of the delayed fluorescent material and the compound 3. Further, a comparative example of EL device 8 was produced by changing the compound 3 in the EL device 6 to the comparative compound A.

The driving voltage at a current density 50 mA/cm$^2$ and the device lifetime of the thus-produced organic electroluminescent devices were evaluated in the same manner as in Examples 2 and 3. The maximum component of light emission from the EL devices 5 to 8 was emission from D35.

Also it was observed that the EL devices 5 to 7 using a delayed fluorescent material as an assist dopant and using the compound 3 represented by the general formula (1) could drive at a lower voltage as compared with the EL device 8 using the comparative compound A. In addition, it was confirmed that the EL device 6 using the compound 3 of the general formula (1) could significantly reduce luminance degradation as compared with the EL device 8 having the same content of the host material but using the comparative compound A. From this, it was confirmed that the organic electroluminescent device using a compound of the general formula (1) as a host material for a delayed fluorescent material and a fluorescent material has good electroconductivity and device durability.

TABLE 4

| Organic Electroluminescent Device | Host Material | Content of Delayed Fluorescent Material (mass %) | Driving Voltage (V) [difference from EL device 8] | Device Lifetime [ratio to EL device 8] |
|---|---|---|---|---|
| EL device 5 (tire invention) | Compound 3 | 30 | −0.2 | — |
| EL device 6 (the invention) | Compound 3 | 40 | −0.2 | 1.41 |
| EL device 7 (the invention) | Compound 3 | 50 | −0.1 | — |
| EL device 8 (comparative example) | Comparative compound A | 40 | 0 (reference) | 1 (reference) |

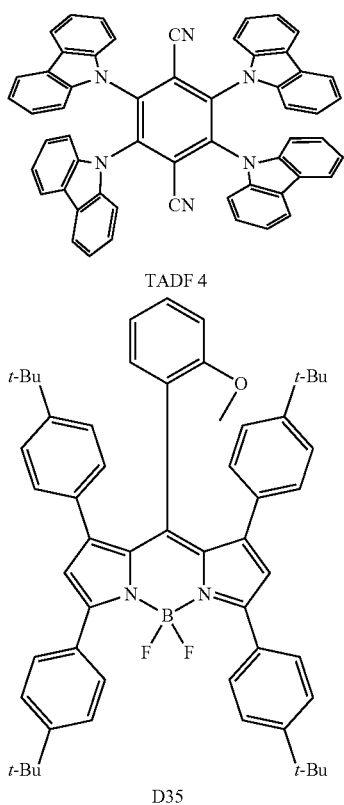

TADF 4

D35

REFERENCE SIGNS LIST

1 Substrate
2 Anode
3 Hole Injection Layer
4 Hole Transporting Layer
5 Light-Emitting Layer
6 Electron Transporting Layer
7 Cathode

The invention claimed is:

1. A host material for use along with a delayed fluorescent material, comprising a compound having a structure represented by the following formula (1):

General Formula (1)

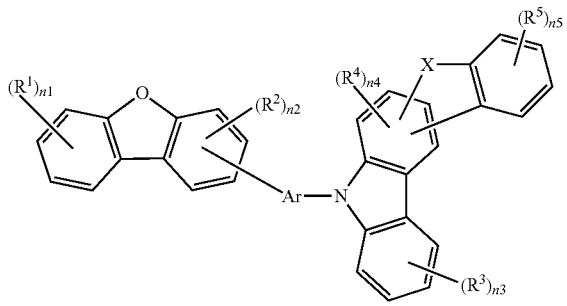

wherein $R^1$ to $R^5$ each independently represent a deuterium or a substituent having a Hammett's σp value that falls within a range of −0.3 to 0.3, $R^1$ to $R^5$ do not bond to the other $R^1$ to $R^5$ or Ar to form a cyclic structure, but neighboring $R^3$'s can bond to each other to form a benzofuro structure or a benzothieno structure; n1, n3 and n5 each independently represent an integer of any of 0 to 4, n2 represents an integer of any of 0 to 3, n4 represents an integer of any of 0 to 2; X represents an oxygen atom or a sulfur atom; Ar represents a monocyclic arylene group or a monocyclic heteroarylene group, and the monocyclic arylene group and the monocyclic heteroarylene group are unsubstituted or are substituted with at least one group consisting of deuterium or an alkyl group.

2. The host material according to claim 1, wherein the compound has a structure represented by the following general formula (2):

General Formula (2)

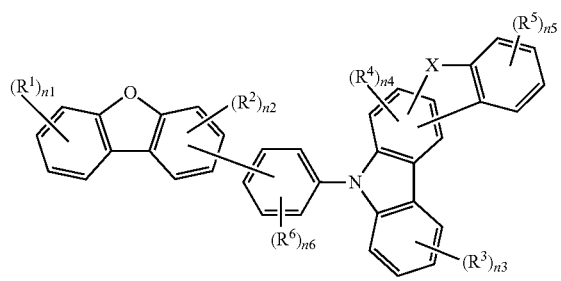

wherein $R^1$ to $R^5$ each independently represent a deuterium or a substituent having a Hammett's σp value that falls within a range of −0.3 to 0.3, $R^1$ to $R^5$ do not bond to the other $R^1$ to $R^6$ to form a cyclic structure, but neighboring $R^3$'s can bond to each other to form a benzofuro structure or a benzothieno structure; R6 represents deuterium or an alkyl group; n1, n3 and n5 each independently represent an integer of any of 0 to 4, n2 and n6 each independently represent an integer of any of 0 to 3, n4 represents an integer of any of 0 to 2; X represents an oxygen atom or a sulfur atom.

3. The host material according to claim 1, wherein the compound has a structure represented by the following general formula (3):

General Formula (3)

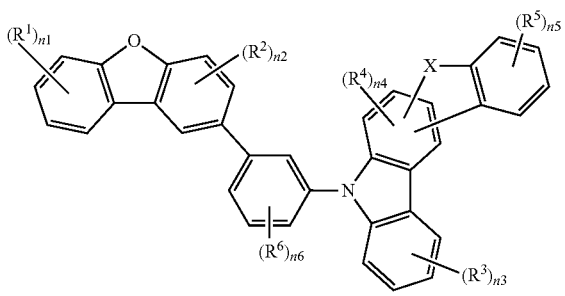

wherein $R^1$ to $R^5$ each independently represent a deuterium or a substituent having a Hammett's σp value that falls within a range of −0.3 to 0.3, $R^1$ to $R^5$ do not bond to the other $R^1$ to $R^6$ to form a cyclic structure, but neighboring $R^3$'s can bond to each other to form a benzofuro structure or a benzothieno structure; R6 represents deuterium or an alkyl group; n1, n3 and n5 each independently represent an integer of any of 0 to 4, n2 and n6 each independently represent an integer of any of 0 to 3, n4 represents an integer of any of 0 to 2; X represents an oxygen atom or a sulfur atom.

4. The host material according to claim 1, wherein:
$R^1$ to $R^5$ each independently represent one group or a combination of two or more groups selected from the group consisting of an alkyl group and an aryl group,
Ar represents a monocyclic arylene group optionally substituted with one group or a combination of two or more groups selected from the group consisting of an alkyl group and an aryl group, or a monocyclic heteroarylene group optionally substituted with one group or a combination of two or more groups selected from the group consisting of an alkyl group and an aryl group.

5. The host material according to claim 1, wherein Ar is a substituted or unsubstituted 1,3-phenylene group.

6. The host material according to claim 1, wherein X is an oxygen atom.

7. A composition comprising the host material of claim 1 doped with a delayed fluorescent material.

8. The composition according to claim 7, which is a film.

9. The composition according to claim 7, wherein the delayed fluorescent material is a compound having a cyanobenzene structure in which the number of the cyano group substituting on the benzene ring is one.

10. The composition according to claim 7, wherein the delayed fluorescent material is a compound having a dicyanobenzene structure in which the number of the cyano groups substituting on the benzene ring is two.

11. The composition according to claim 7, wherein the delayed fluorescent material is a compound having an azabenzene structure in which at least one ring skeleton-constituting carbon atom of the benzene ring is replaced with a nitrogen atom.

12. The composition according to claim 7 further containing a fluorescent compound whose lowest excited singlet energy is lower than that of the host material and the delayed fluorescent material.

13. An organic light-emitting device having a layer of the composition of claim 8.

14. The organic light-emitting device according to claim 13, wherein the layer is formed of atoms alone selected from the group consisting of a carbon atom, a hydrogen atom, a nitrogen atom, an oxygen atom, a sulfur atom, a boron atom, and a halogen atom.

15. The organic light-emitting device according to claim 13, wherein the layer is formed of atoms alone selected from the group consisting of a carbon atom, a hydrogen atom, a nitrogen atom, an oxygen atom, and a sulfur atom.

16. The organic light-emitting device according to claim 13, which is an organic electroluminescent device.

17. The organic light-emitting device according to claim 13, wherein the composition does not contain the fluorescent compound, and the maximum component for light emission from the device is light emission from the delayed fluorescent material.

18. The organic light-emitting device according to claim 13, wherein the composition contains the fluorescent compound, and the maximum component for light emission from the device is light emission from the fluorescent material.

* * * * *